US008372602B2

(12) United States Patent
Presnell et al.

(10) Patent No.: US 8,372,602 B2
(45) **Date of Patent: *Feb. 12, 2013**

(54) METHODS FOR PRODUCING CYTOKINE RECEPTOR ZALPHA11

(75) Inventors: Scott R. Presnell, Tacoma, WA (US); Darrell C. Conklin, Seattle, WA (US); Julia E. Novak, Balnbridge Island, WA (US); Angela K. Hammond, Issaquah, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/339,779

(22) Filed: Dec. 29, 2011

(65) Prior Publication Data

US 2012/0208236 A1 Aug. 16, 2012

Related U.S. Application Data

(60) Continuation of application No. 13/039,459, filed on Mar. 3, 2011, now Pat. No. 8,110,372, which is a division of application No. 12/623,651, filed on Nov. 23, 2009, now Pat. No. 7,923,212, which is a continuation of application No. 11/537,835, filed on Oct. 2, 2006, now Pat. No. 7,638,286, which is a division of application No. 10/715,998, filed on Nov. 18, 2003, now Pat. No. 7,411,056, which is a division of application No. 09/404,641, filed on Sep. 23, 1999, now Pat. No. 6,576,744.

(60) Provisional application No. 60/100,896, filed on Sep. 23, 1998, provisional application No. 60/123,546, filed on Mar. 9, 1999, provisional application No. 60/142,574, filed on Jul. 6, 1999.

(51) Int. Cl.

| | |
|---|---|
| ***C12P 21/06*** | (2006.01) |
| ***C12P 21/04*** | (2006.01) |
| ***C07H 21/04*** | (2006.01) |

(52) U.S. Cl. .................. 435/69.1; 435/69.7; 435/320.1; 536/23.4; 536/23.5; 536/24.1

(58) Field of Classification Search ........................ None
See application file for complete search history.

(56) References Cited

U.S. PATENT DOCUMENTS

| | | | | |
|---|---|---|---|---|
| 6,057,128 | A * | 5/2000 | Donaldson et al. | 435/69.1 |
| 6,307,024 | B1 | 10/2001 | Novak et al. | |
| 7,411,056 | B2 * | 8/2008 | Presnell et al. | 536/23.5 |

FOREIGN PATENT DOCUMENTS

| | | |
|---|---|---|
| EP | 1088831 | 4/2001 |
| WO | 95/33059 | 12/1995 |
| WO | 98/31811 | 7/1998 |
| WO | 99/47675 | 9/1999 |
| WO | 99/67290 | 12/1999 |
| WO | 00/08152 | 2/2000 |
| WO | 00/17235 | 3/2000 |

OTHER PUBLICATIONS

Parrish et al., *American Journal of Human Genetics 65:* A378. 49$^{th}$ Annual Meeting of the American Society of Human Genetics, Oct. 19-23, 1999.
Parrish-Novak et al., *Nature 408:* 57-63, 2000.
Ozaki et al., *Proc. Natl. Acad. Sci. USA 97:* 11439-11444, 2000.
Asao et al., *J. Immunology 167:*1-5, 2001.
Bazan, *Proc. Natl Acad Sci. USA.* 87:6934-6938, 1990.
Hudson, Whitehead Institute/MIT Center for Human Genome Research, 1995, EMBL database Accession No. G13225 (Dec. 22, 1995).
Adams et al., Institute for Genomic Research, Rockville, MD, 1997, EMBL database Accession No. AC002303 (Jun. 26, 1997).
Maslinki & Storm from WIPO Publication No. 9744058, 1997,. EMBL database Accession No. W39210 (May 22, 1998).
Incyte Pharmaceuticals, Inc, clone, 1995: INC478347.
Hillier et al., Wash-U-Merck EST Project, 1996, Public EST 196: EST768027.
TIGR Tentative Human Consensus 1997: THC_AA129802.
Incyte Pharmaceuticals, Inc. clone 1998: INC4298246.
Incyte Pharmaceuticals, Inc. clone 1998: INC4298636.
Adams et al., Institute for Genomic Research, Rockville, MD, 1998, Human chromosome 16 BAC clone CIT987-SKA-670BS (Aug. 25, 1997): Accession No. AC002303.
Adams et al., Institute for Genomic Research, Rockville, MD, 1998, Human chromosome 16 BAC clone CIT987SK-582J2 (Jun. 13, 1998): Accession No. AC004525.
Hudson, Whitehead Institute/MIT Center for Human Genome Research, 1995, Human STS WI-10673 (Dec. 20, 1995); Accession No. G13225.
Incyte Pharmaceuticals, Inc. library 1995: MMLR2DT01.
Incyte Pharmaceuticals, Inc. library 1998: SCOMDIT01.
Incyte Pharmaceuticals, Inc. library 1998: BRAIHCT02.
Incyte Pharmaceuticals, Inc. cline 1998: INC4718117.

* cited by examiner

*Primary Examiner* — Christine J Saoud
*Assistant Examiner* — Jegatheesan Seharaseyon
(74) *Attorney, Agent, or Firm* — Eve L. Frank

(57) ABSTRACT

Novel polypeptides, polynucleotides encoding the polypeptides, and related compositions and methods are disclosed for zalpha11, a novel cytokine receptor. The polypeptides may be used within methods for detecting ligands that stimulate the proliferation and/or development of hematopoietic, lymphoid and myeloid cells in vitro and in vivo. Ligand-binding receptor polypeptides can also be used to block ligand activity in vitro and in vivo. The polynucleotides encoding zalpha11, are located on chromosome 16, and can be used to identify a region of the genome associated with human disease states. The present invention also includes methods for producing the protein, uses therefor and antibodies thereto.

7 Claims, 9 Drawing Sheets

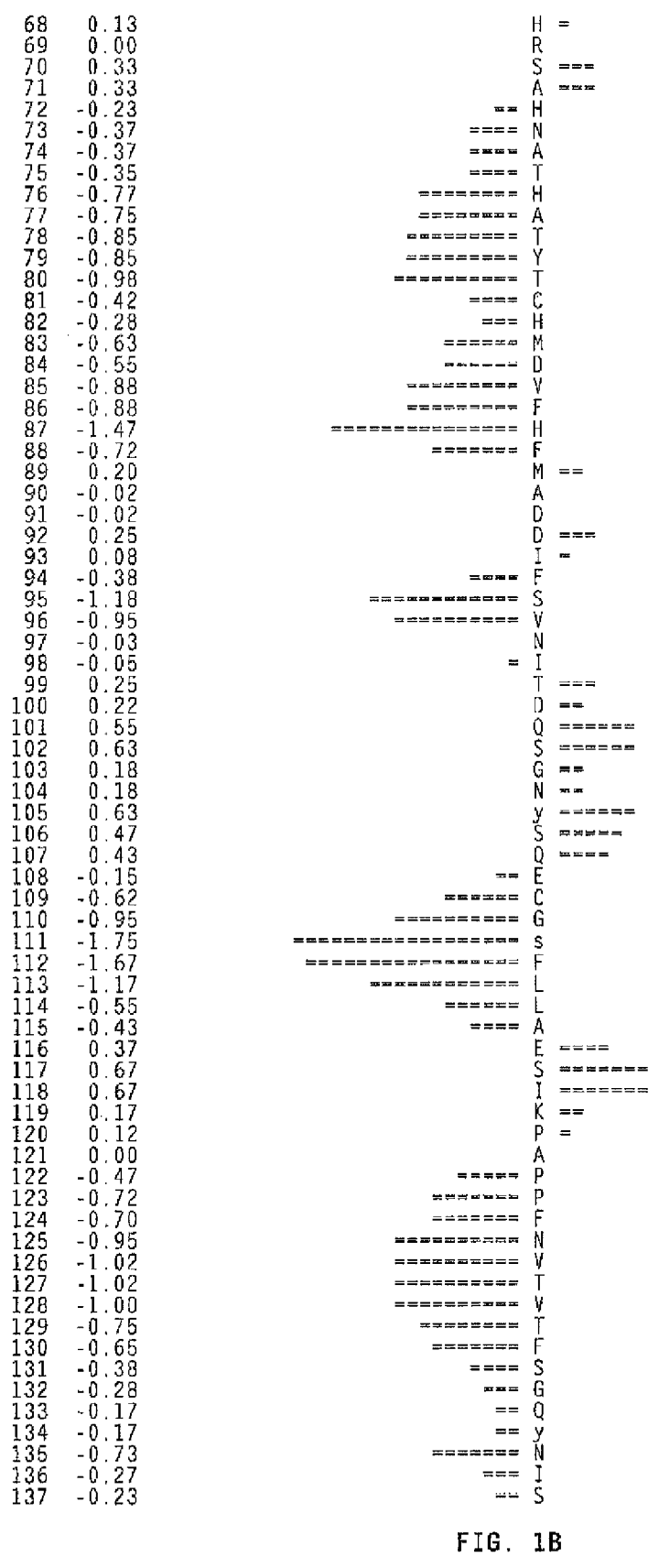

| | | |
|---|---|---|
| 68 | 0.13 | H |
| 69 | 0.00 | R |
| 70 | 0.33 | S |
| 71 | 0.33 | A |
| 72 | -0.23 | H |
| 73 | -0.37 | N |
| 74 | -0.37 | A |
| 75 | -0.35 | T |
| 76 | -0.77 | H |
| 77 | -0.75 | A |
| 78 | -0.85 | T |
| 79 | -0.85 | Y |
| 80 | -0.98 | T |
| 81 | -0.42 | C |
| 82 | -0.28 | H |
| 83 | -0.63 | M |
| 84 | -0.55 | D |
| 85 | -0.88 | V |
| 86 | -0.88 | F |
| 87 | -1.47 | H |
| 88 | -0.72 | F |
| 89 | 0.20 | M |
| 90 | -0.02 | A |
| 91 | -0.02 | D |
| 92 | 0.25 | D |
| 93 | 0.08 | I |
| 94 | -0.38 | F |
| 95 | -1.18 | S |
| 96 | -0.95 | V |
| 97 | -0.03 | N |
| 98 | -0.05 | I |
| 99 | 0.25 | T |
| 100 | 0.22 | D |
| 101 | 0.55 | Q |
| 102 | 0.63 | S |
| 103 | 0.18 | G |
| 104 | 0.18 | N |
| 105 | 0.63 | y |
| 106 | 0.47 | S |
| 107 | 0.43 | Q |
| 108 | -0.15 | E |
| 109 | -0.62 | C |
| 110 | -0.95 | G |
| 111 | -1.75 | s |
| 112 | -1.67 | F |
| 113 | -1.17 | L |
| 114 | -0.55 | L |
| 115 | -0.43 | A |
| 116 | 0.37 | E |
| 117 | 0.67 | S |
| 118 | 0.67 | I |
| 119 | 0.17 | K |
| 120 | 0.12 | P |
| 121 | 0.00 | A |
| 122 | -0.47 | P |
| 123 | -0.72 | P |
| 124 | -0.70 | F |
| 125 | -0.95 | N |
| 126 | -1.02 | V |
| 127 | -1.02 | T |
| 128 | -1.00 | V |
| 129 | -0.75 | T |
| 130 | -0.65 | F |
| 131 | -0.38 | S |
| 132 | -0.28 | G |
| 133 | -0.17 | Q |
| 134 | -0.17 | y |
| 135 | -0.73 | N |
| 136 | -0.27 | I |
| 137 | -0.23 | S |

FIG. 1B

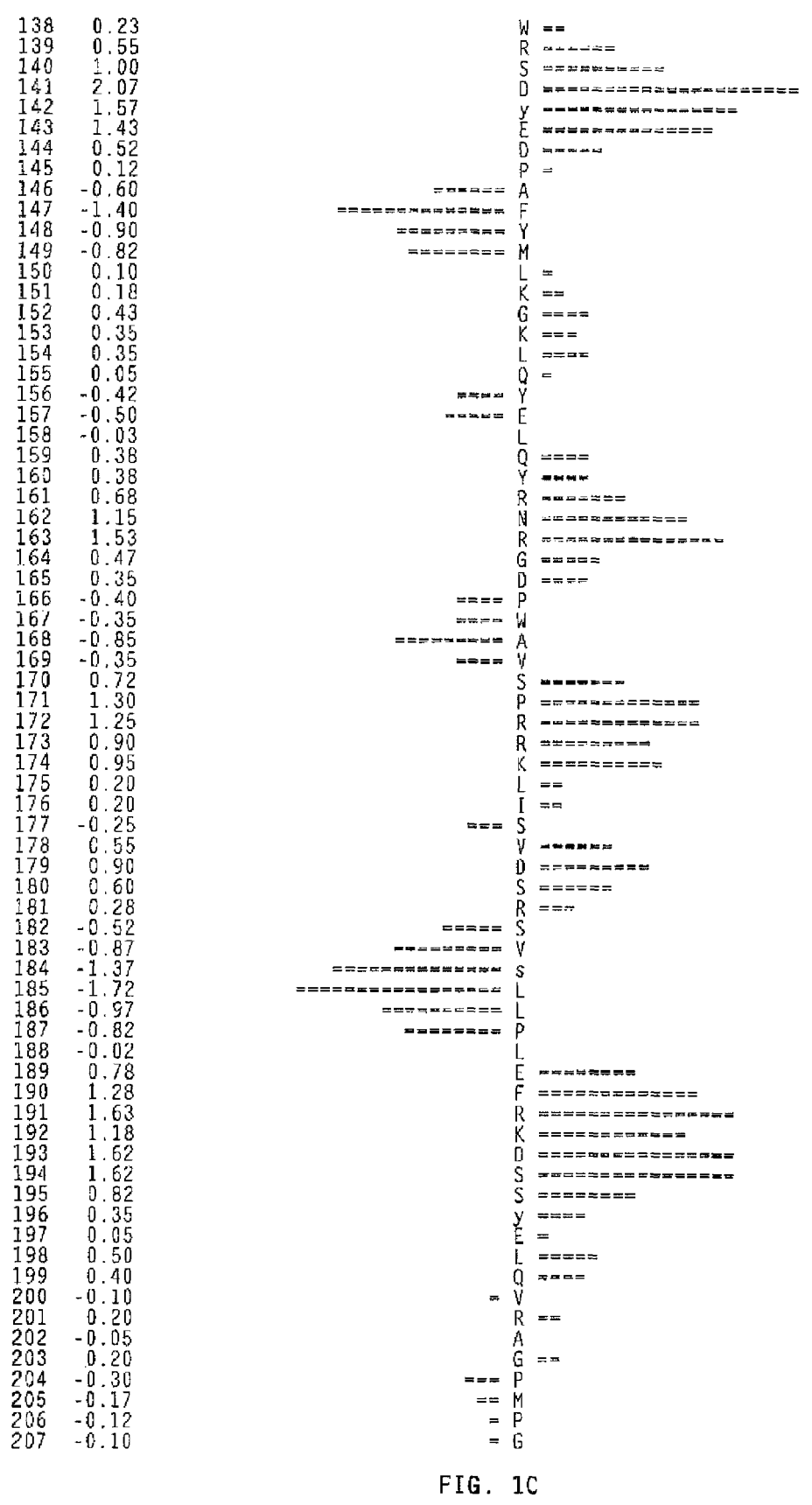

| Position | Value | Residue |
|---|---|---|
| 138 | 0.23 | W |
| 139 | 0.55 | R |
| 140 | 1.00 | S |
| 141 | 2.07 | D |
| 142 | 1.57 | y |
| 143 | 1.43 | E |
| 144 | 0.52 | D |
| 145 | 0.12 | P |
| 146 | -0.60 | A |
| 147 | -1.40 | F |
| 148 | -0.90 | Y |
| 149 | -0.82 | M |
| 150 | 0.10 | L |
| 151 | 0.18 | K |
| 152 | 0.43 | G |
| 153 | 0.35 | K |
| 154 | 0.35 | L |
| 155 | 0.05 | Q |
| 156 | -0.42 | Y |
| 157 | -0.50 | E |
| 158 | -0.03 | L |
| 159 | 0.38 | Q |
| 160 | 0.38 | Y |
| 161 | 0.68 | R |
| 162 | 1.15 | N |
| 163 | 1.53 | R |
| 164 | 0.47 | G |
| 165 | 0.35 | D |
| 166 | -0.40 | P |
| 167 | -0.35 | W |
| 168 | -0.85 | A |
| 169 | -0.35 | V |
| 170 | 0.72 | S |
| 171 | 1.30 | P |
| 172 | 1.25 | R |
| 173 | 0.90 | R |
| 174 | 0.95 | K |
| 175 | 0.20 | L |
| 176 | 0.20 | I |
| 177 | -0.25 | S |
| 178 | 0.55 | V |
| 179 | 0.90 | D |
| 180 | 0.60 | S |
| 181 | 0.28 | R |
| 182 | -0.52 | S |
| 183 | -0.87 | V |
| 184 | -1.37 | s |
| 185 | -1.72 | L |
| 186 | -0.97 | L |
| 187 | -0.82 | P |
| 188 | -0.02 | L |
| 189 | 0.78 | E |
| 190 | 1.28 | F |
| 191 | 1.63 | R |
| 192 | 1.18 | K |
| 193 | 1.62 | D |
| 194 | 1.62 | S |
| 195 | 0.82 | S |
| 196 | 0.35 | y |
| 197 | 0.05 | E |
| 198 | 0.50 | L |
| 199 | 0.40 | Q |
| 200 | -0.10 | V |
| 201 | 0.20 | R |
| 202 | -0.05 | A |
| 203 | 0.20 | G |
| 204 | -0.30 | P |
| 205 | -0.17 | M |
| 206 | -0.12 | P |
| 207 | -0.10 | G |

FIG. 1C

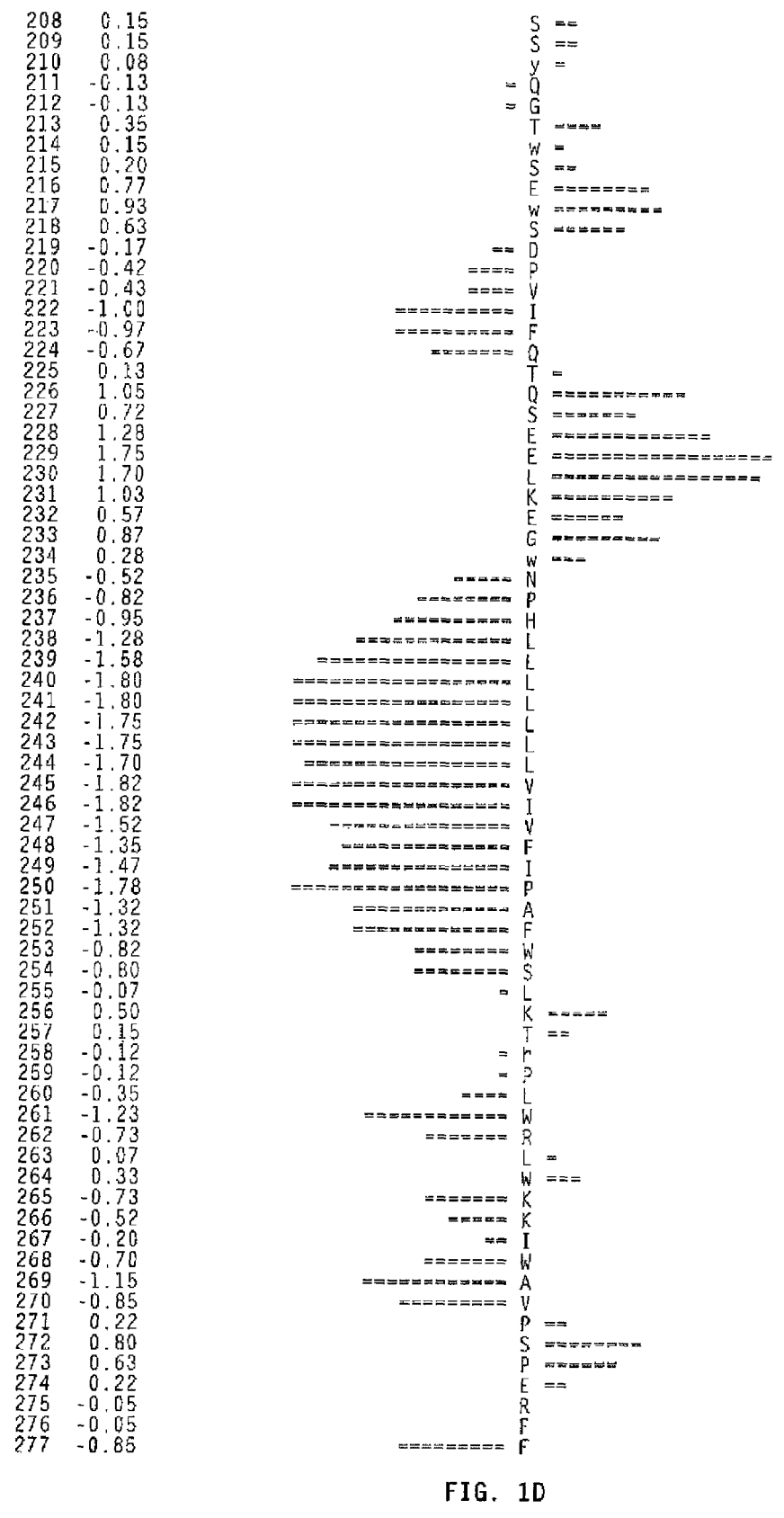

| | | |
|---|---|---|
| 208 | 0.15 | S |
| 209 | 0.15 | S |
| 210 | 0.08 | y |
| 211 | -0.13 | Q |
| 212 | -0.13 | G |
| 213 | 0.35 | T |
| 214 | 0.15 | W |
| 215 | 0.20 | S |
| 216 | 0.77 | E |
| 217 | 0.93 | w |
| 218 | 0.63 | S |
| 219 | -0.17 | D |
| 220 | -0.42 | P |
| 221 | -0.43 | V |
| 222 | -1.00 | I |
| 223 | -0.97 | F |
| 224 | -0.67 | Q |
| 225 | 0.13 | T |
| 226 | 1.05 | Q |
| 227 | 0.72 | S |
| 228 | 1.28 | E |
| 229 | 1.75 | E |
| 230 | 1.70 | L |
| 231 | 1.03 | K |
| 232 | 0.57 | E |
| 233 | 0.87 | G |
| 234 | 0.28 | w |
| 235 | -0.52 | N |
| 236 | -0.82 | P |
| 237 | -0.95 | H |
| 238 | -1.28 | L |
| 239 | -1.58 | L |
| 240 | -1.80 | L |
| 241 | -1.80 | L |
| 242 | -1.75 | L |
| 243 | -1.75 | L |
| 244 | -1.70 | L |
| 245 | -1.82 | V |
| 246 | -1.82 | I |
| 247 | -1.52 | V |
| 248 | -1.35 | F |
| 249 | -1.47 | I |
| 250 | -1.78 | P |
| 251 | -1.32 | A |
| 252 | -1.32 | F |
| 253 | -0.82 | W |
| 254 | -0.80 | S |
| 255 | -0.07 | L |
| 256 | 0.50 | K |
| 257 | 0.15 | T |
| 258 | -0.12 | r |
| 259 | -0.12 | P |
| 260 | -0.35 | L |
| 261 | -1.23 | W |
| 262 | -0.73 | R |
| 263 | 0.07 | L |
| 264 | 0.33 | W |
| 265 | -0.73 | K |
| 266 | -0.52 | K |
| 267 | -0.20 | I |
| 268 | -0.70 | W |
| 269 | -1.15 | A |
| 270 | -0.85 | V |
| 271 | 0.22 | P |
| 272 | 0.80 | S |
| 273 | 0.63 | P |
| 274 | 0.22 | E |
| 275 | -0.05 | R |
| 276 | -0.05 | F |
| 277 | -0.86 | F |

FIG. 1D

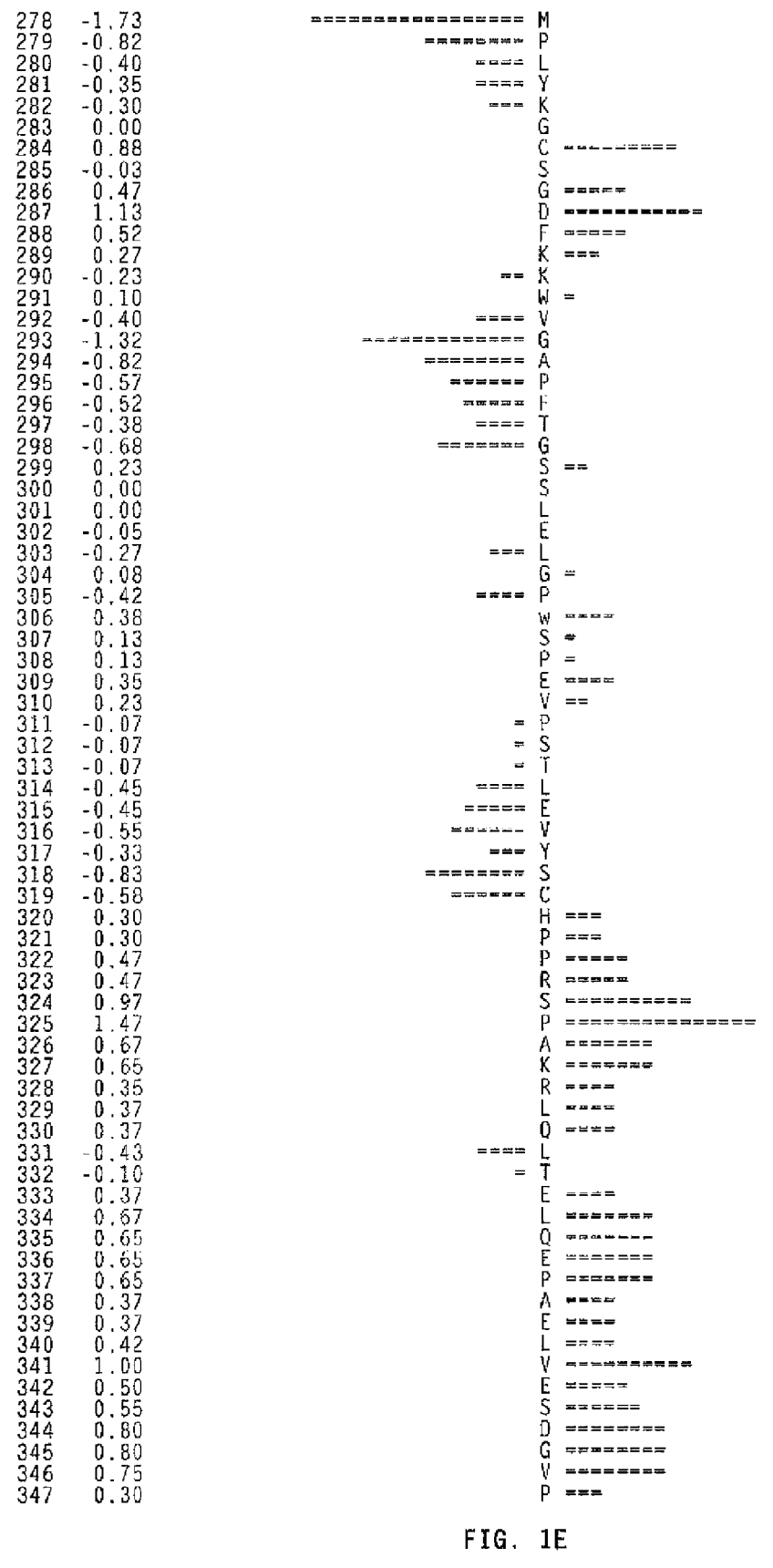

| | | |
|---|---|---|
| 278 | -1.73 | M |
| 279 | -0.82 | P |
| 280 | -0.40 | L |
| 281 | -0.35 | Y |
| 282 | -0.30 | K |
| 283 | 0.00 | G |
| 284 | 0.88 | C |
| 285 | -0.03 | S |
| 286 | 0.47 | G |
| 287 | 1.13 | D |
| 288 | 0.52 | F |
| 289 | 0.27 | K |
| 290 | -0.23 | K |
| 291 | 0.10 | W |
| 292 | -0.40 | V |
| 293 | -1.32 | G |
| 294 | -0.82 | A |
| 295 | -0.57 | P |
| 296 | -0.52 | F |
| 297 | -0.38 | T |
| 298 | -0.68 | G |
| 299 | 0.23 | S |
| 300 | 0.00 | S |
| 301 | 0.00 | L |
| 302 | -0.05 | E |
| 303 | -0.27 | L |
| 304 | 0.08 | G |
| 305 | -0.42 | P |
| 306 | 0.38 | W |
| 307 | 0.13 | S |
| 308 | 0.13 | P |
| 309 | 0.35 | E |
| 310 | 0.23 | V |
| 311 | -0.07 | P |
| 312 | -0.07 | S |
| 313 | -0.07 | T |
| 314 | -0.45 | L |
| 315 | -0.45 | E |
| 316 | -0.55 | V |
| 317 | -0.33 | Y |
| 318 | -0.83 | S |
| 319 | -0.58 | C |
| 320 | 0.30 | H |
| 321 | 0.30 | P |
| 322 | 0.47 | P |
| 323 | 0.47 | R |
| 324 | 0.97 | S |
| 325 | 1.47 | P |
| 326 | 0.67 | A |
| 327 | 0.65 | K |
| 328 | 0.35 | R |
| 329 | 0.37 | L |
| 330 | 0.37 | Q |
| 331 | -0.43 | L |
| 332 | -0.10 | T |
| 333 | 0.37 | E |
| 334 | 0.67 | L |
| 335 | 0.65 | Q |
| 336 | 0.65 | E |
| 337 | 0.65 | P |
| 338 | 0.37 | A |
| 339 | 0.37 | E |
| 340 | 0.42 | L |
| 341 | 1.00 | V |
| 342 | 0.50 | E |
| 343 | 0.55 | S |
| 344 | 0.80 | D |
| 345 | 0.80 | G |
| 346 | 0.75 | V |
| 347 | 0.30 | P |

FIG. 1E

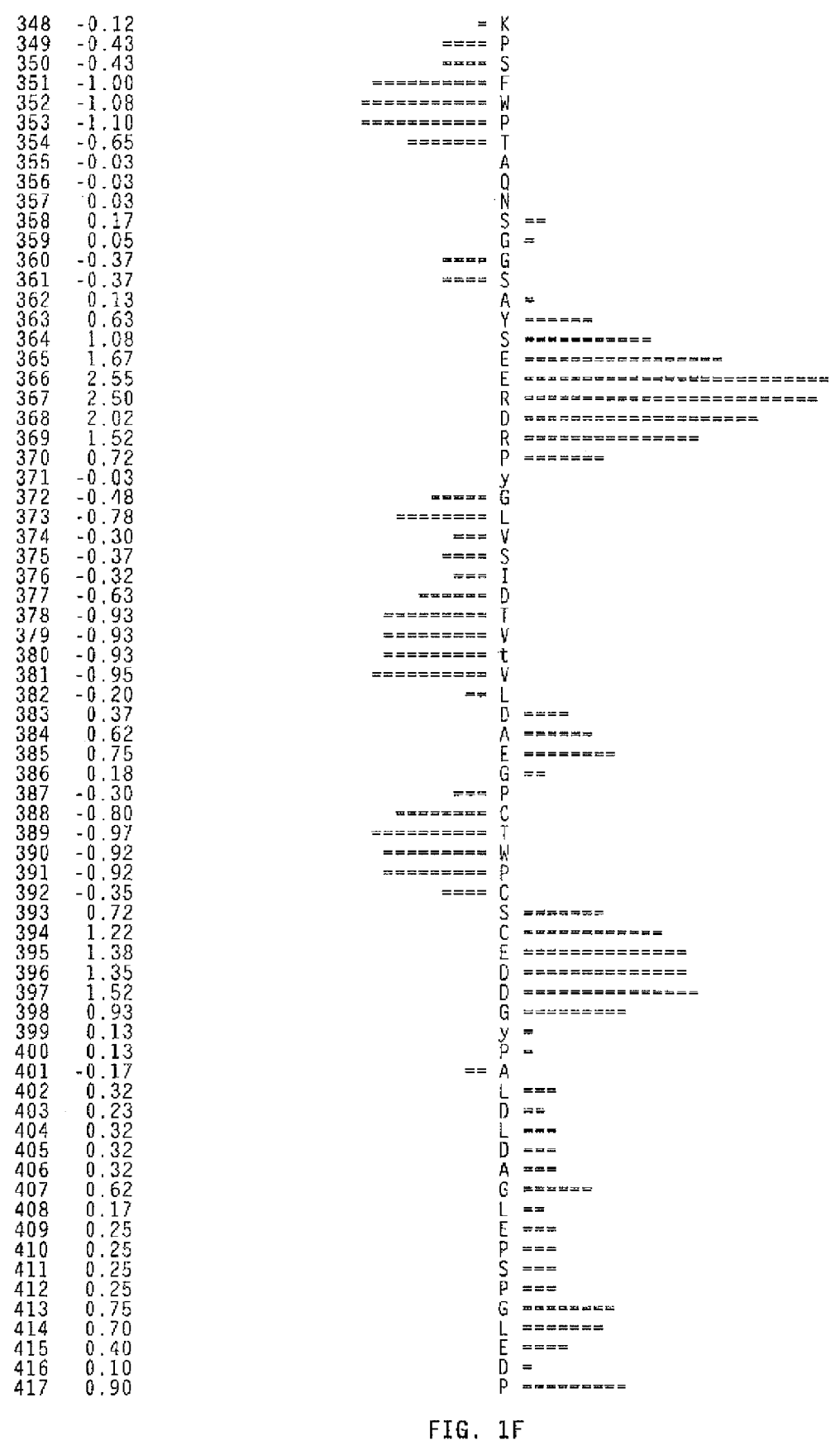

| | | |
|---|---|---|
| 348 | -0.12 | K |
| 349 | -0.43 | P |
| 350 | -0.43 | S |
| 351 | -1.00 | F |
| 352 | -1.08 | W |
| 353 | -1.10 | P |
| 354 | -0.65 | T |
| 355 | -0.03 | A |
| 356 | -0.03 | Q |
| 357 | 0.03 | N |
| 358 | 0.17 | S |
| 359 | 0.05 | G |
| 360 | -0.37 | G |
| 361 | -0.37 | S |
| 362 | 0.13 | A |
| 363 | 0.63 | Y |
| 364 | 1.08 | S |
| 365 | 1.67 | E |
| 366 | 2.55 | E |
| 367 | 2.50 | R |
| 368 | 2.02 | D |
| 369 | 1.52 | R |
| 370 | 0.72 | P |
| 371 | -0.03 | y |
| 372 | -0.48 | G |
| 373 | -0.78 | L |
| 374 | -0.30 | V |
| 375 | -0.37 | S |
| 376 | -0.32 | I |
| 377 | -0.63 | D |
| 378 | -0.93 | T |
| 379 | -0.93 | V |
| 380 | -0.93 | t |
| 381 | -0.95 | V |
| 382 | -0.20 | L |
| 383 | 0.37 | D |
| 384 | 0.62 | A |
| 385 | 0.75 | E |
| 386 | 0.18 | G |
| 387 | -0.30 | P |
| 388 | -0.80 | C |
| 389 | -0.97 | T |
| 390 | -0.92 | W |
| 391 | -0.92 | P |
| 392 | -0.35 | C |
| 393 | 0.72 | S |
| 394 | 1.22 | C |
| 395 | 1.38 | E |
| 396 | 1.35 | D |
| 397 | 1.52 | D |
| 398 | 0.93 | G |
| 399 | 0.13 | y |
| 400 | 0.13 | P |
| 401 | -0.17 | A |
| 402 | 0.32 | L |
| 403 | 0.23 | D |
| 404 | 0.32 | L |
| 405 | 0.32 | D |
| 406 | 0.32 | A |
| 407 | 0.62 | G |
| 408 | 0.17 | L |
| 409 | 0.25 | E |
| 410 | 0.25 | P |
| 411 | 0.25 | S |
| 412 | 0.25 | P |
| 413 | 0.75 | G |
| 414 | 0.70 | L |
| 415 | 0.40 | E |
| 416 | 0.10 | D |
| 417 | 0.90 | P |

FIG. 1F

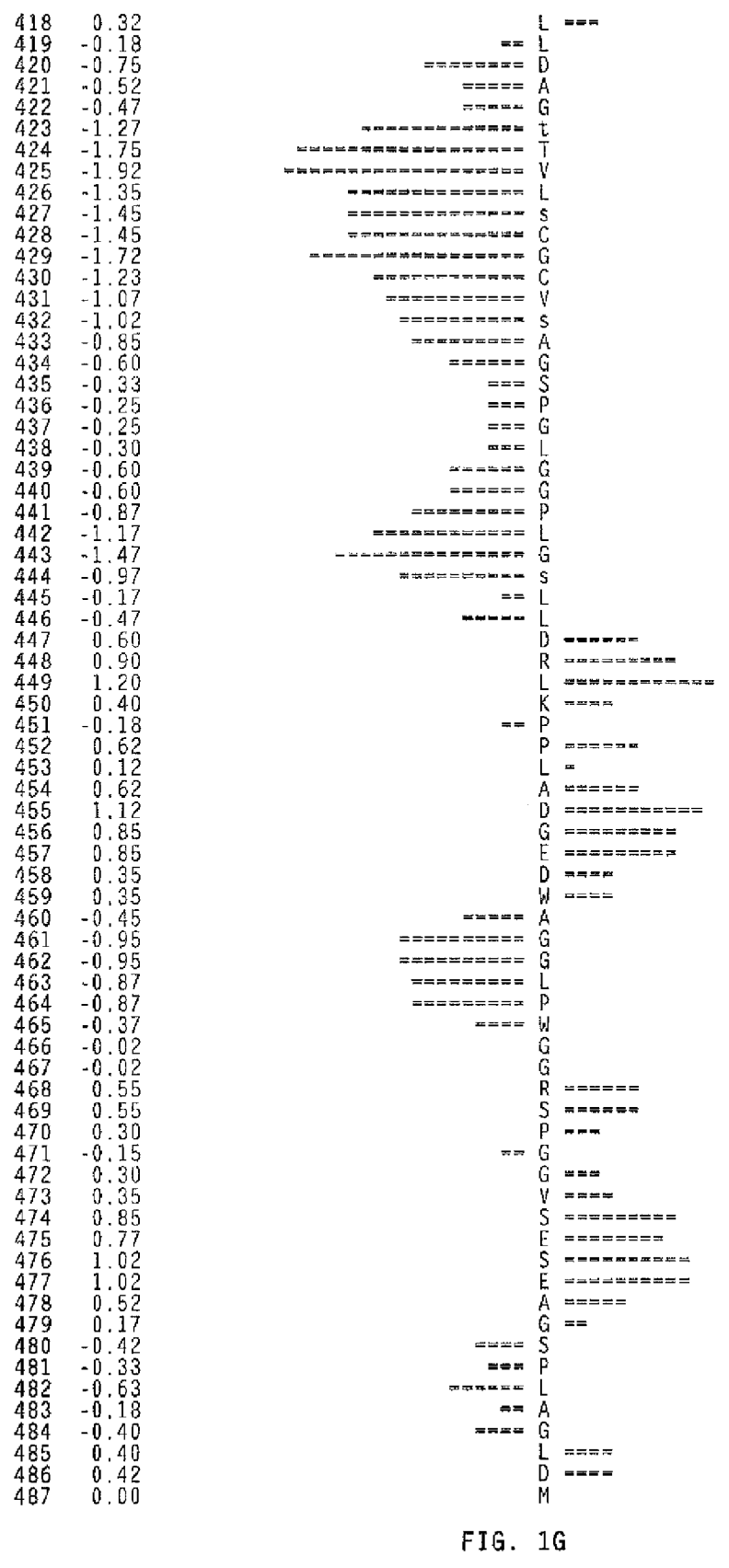

| | | |
|---|---|---|
| 418 | 0.32 | L |
| 419 | -0.18 | L |
| 420 | -0.75 | D |
| 421 | -0.52 | A |
| 422 | -0.47 | G |
| 423 | -1.27 | t |
| 424 | -1.75 | T |
| 425 | -1.92 | V |
| 426 | -1.35 | L |
| 427 | -1.45 | s |
| 428 | -1.45 | C |
| 429 | -1.72 | G |
| 430 | -1.23 | C |
| 431 | -1.07 | V |
| 432 | -1.02 | s |
| 433 | -0.85 | A |
| 434 | -0.60 | G |
| 435 | -0.33 | S |
| 436 | -0.25 | P |
| 437 | -0.25 | G |
| 438 | -0.30 | L |
| 439 | -0.60 | G |
| 440 | -0.60 | G |
| 441 | -0.87 | P |
| 442 | -1.17 | L |
| 443 | -1.47 | G |
| 444 | -0.97 | s |
| 445 | -0.17 | L |
| 446 | -0.47 | L |
| 447 | 0.60 | D |
| 448 | 0.90 | R |
| 449 | 1.20 | L |
| 450 | 0.40 | K |
| 451 | -0.18 | P |
| 452 | 0.62 | P |
| 453 | 0.12 | L |
| 454 | 0.62 | A |
| 455 | 1.12 | D |
| 456 | 0.85 | G |
| 457 | 0.85 | E |
| 458 | 0.35 | D |
| 459 | 0.35 | W |
| 460 | -0.45 | A |
| 461 | -0.95 | G |
| 462 | -0.95 | G |
| 463 | -0.87 | L |
| 464 | -0.87 | P |
| 465 | -0.37 | W |
| 466 | -0.02 | G |
| 467 | -0.02 | G |
| 468 | 0.55 | R |
| 469 | 0.55 | S |
| 470 | 0.30 | P |
| 471 | -0.15 | G |
| 472 | 0.30 | G |
| 473 | 0.35 | V |
| 474 | 0.85 | S |
| 475 | 0.77 | E |
| 476 | 1.02 | S |
| 477 | 1.02 | E |
| 478 | 0.52 | A |
| 479 | 0.17 | G |
| 480 | -0.42 | S |
| 481 | -0.33 | P |
| 482 | -0.63 | L |
| 483 | -0.18 | A |
| 484 | -0.40 | G |
| 485 | 0.40 | L |
| 486 | 0.42 | D |
| 487 | 0.00 | M |

FIG. 1G

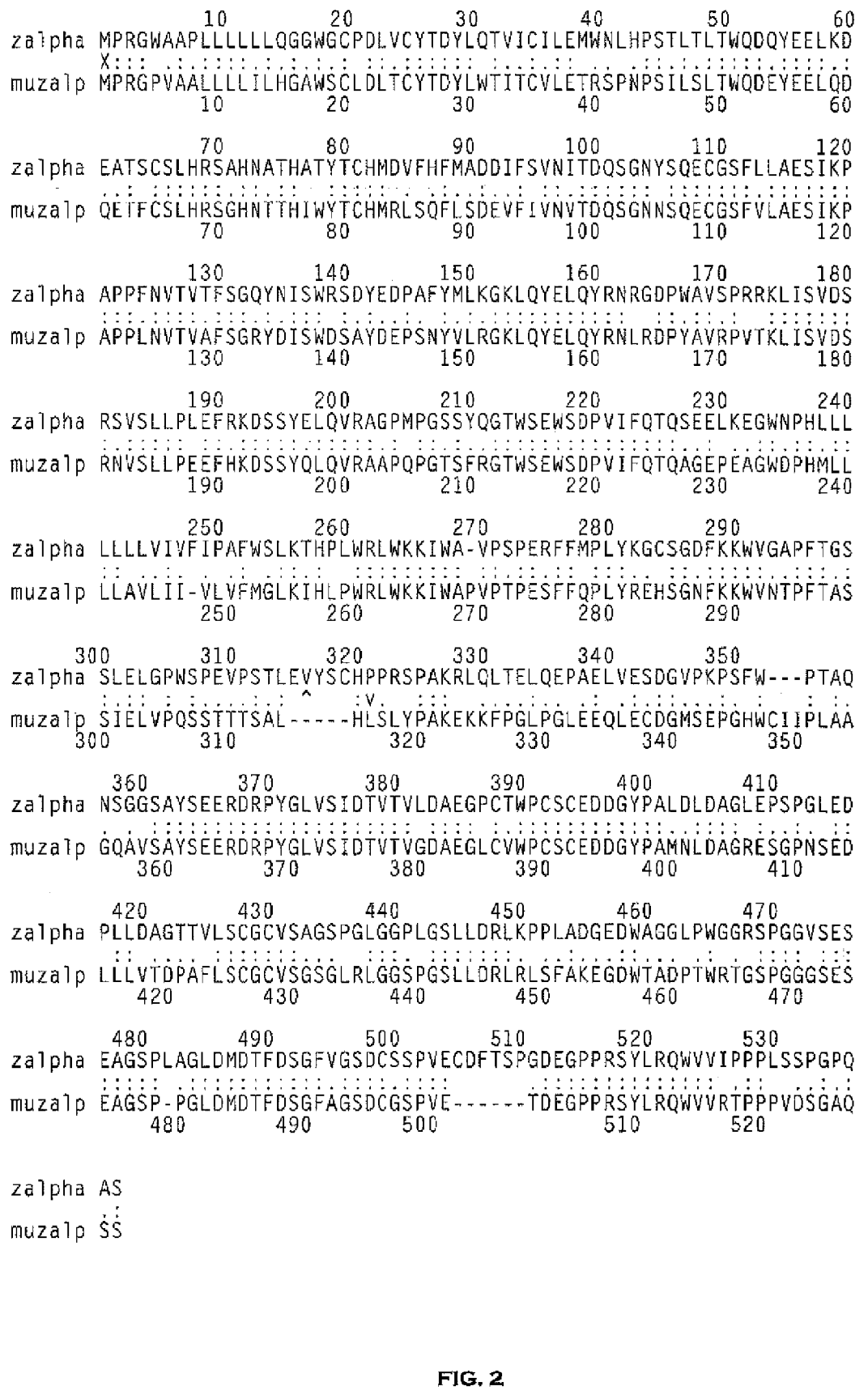

```
                 10        20        30        40        50        60
zalpha  MPRGWAAPLLLLLLQGGWGCPDLVCYTDYLQTVICILEMWNLHPSTLTLTWQDQYEELKD

muzalp  MPRGPVAALLLLILHGAWSCLDLTCYTDYLWTITCVLETRSPNPSILSLTWQDEYEELQD
                 10        20        30        40        50        60

                 70        80        90       100       110       120
zalpha  EATSCSLHRSAHNATHATYTCHMDVFHFMADDIFSVNITDQSGNYSQECGSFLLAESIKP

muzalp  QETFCSLHRSGHNTTHIWYTCHMRLSQFLSDEVFIVNVTDQSGNNSQECGSFVLAESIKP
                 70        80        90       100       110       120

                130       140       150       160       170       180
zalpha  APPFNVTVTFSGQYNISWRSDYEDPAFYMLKGKLQYELQYRNRGDPWAVSPRRKLISVDS

muzalp  APPLNVTVAFSGRYDISWDSAYDEPSNYVLRGKLQYELQYRNLRDPYAVRPVTKLISVDS
                130       140       150       160       170       180

                190       200       210       220       230       240
zalpha  RSVSLLPLEFRKDSSYELQVRAGPMPGSSYQGTWSEWSDPVIFQTQSEELKEGWNPHLLL

muzalp  RNVSLLPEEFHKDSSYQLQVRAAPQPGTSFRGTWSEWSDPVIFQTQAGEPEAGWDPHMLL
                190       200       210       220       230       240

                250       260       270       280       290
zalpha  LLLLVIVFIPAFWSLKTHPLWRLWKKIWA-VPSPERFFMPLYKGCSGDFKKWVGAPFTGS

muzalp  LLAVLII-VLVFMGLKIHLPWRLWKKIWAPVPTPESFFQPLYREHSGNFKKWVNTPFTAS
                 250       260       270       280       290

      300       310       320       330       340       350
zalpha  SLELGPNSPEVPSTLEVYSCHPPRSPAKRLQLTELQEPAELVESDGVPKPSFW---PTAQ
                         ^     :V.
muzalp  SIELVPQSSTTTSAL-----HLSLYPAKEKKFPGLPGLEEQLECDGMSEPGHWCIIPLAA
      300       310                 320       330       340       350

          360       370       380       390       400       410
zalpha  NSGGSAYSEERDRPYGLVSIDTVTVLDAEGPCTWPCSCEDDGYPALDLDAGLEPSPGLED

muzalp  GQAVSAYSEERDRPYGLVSIDTVTVGDAEGLCVWPCSCEDDGYPAMNLDAGRESGPNSED
              360       370       380       390       400       410

          420       430       440       450       460       470
zalpha  PLLDAGTTVLSCGCVSAGSPGLGGPLGSLLDRLKPPLADGEDWAGGLPWGGRSPGGVSES

muzalp  LLLVTDPAFLSCGCVSGSGLRLGGSPGSLLDRLRLSFAKEGDWTADPTWRTGSPGGGSES
              420       430       440       450       460       470

          480       490       500       510       520       530
zalpha  EAGSPLAGLDMDTFDSGFVGSDCSSPVECDFTSPGDEGPPRSYLRQWVVIPPPLSSPGPQ

muzalp  EAGSP-PGLDMDTFDSGFAGSDCGSPVE------TDEGPPRSYLRQWVVRTPPPVDSGAQ
               480       490       500                 510       520

zalpha  AS

muzalp  SS
```

FIG. 2

SEQUENCE LISTING

```
<160> NUMBER OF SEQ ID NOS: 91

<210> SEQ ID NO 1
<211> LENGTH: 2887
<212> TYPE: DNA
<213> ORGANISM: Homo sapiens
<220> FEATURE:
<221> NAME/KEY: CDS
<222> LOCATION: (69)...(1682)

<400> SEQUENCE: 1

gaagcagcag gtaccccctc cacatcccta gggctctgtg atgtaggcag aggcccgtgg     60

gagtcagc atg ccg cgt ggc tgg gcc gcc ccc ttg ctc ctg ctg ctg ctc     110
         Met Pro Arg Gly Trp Ala Ala Pro Leu Leu Leu Leu Leu Leu
          1               5                  10

cag gga ggc tgg ggc tgc ccc gac ctc gtc tgc tac acc gat tac ctc     158
Gln Gly Gly Trp Gly Cys Pro Asp Leu Val Cys Tyr Thr Asp Tyr Leu
 15                  20                  25                  30

cag acg gtc atc tgc atc ctg gaa atg tgg aac ctc cac ccc agc acg     206
Gln Thr Val Ile Cys Ile Leu Glu Met Trp Asn Leu His Pro Ser Thr
                 35                  40                  45

ctc acc ctt acc tgg caa gac cag tat gaa gag ctg aag gac gag gcc     254
Leu Thr Leu Thr Trp Gln Asp Gln Tyr Glu Glu Leu Lys Asp Glu Ala
             50                  55                  60

acc tcc tgc agc ctc cac agg tcg gcc cac aat gcc acg cat gcc acc     302
Thr Ser Cys Ser Leu His Arg Ser Ala His Asn Ala Thr His Ala Thr
         65                  70                  75

tac acc tgc cac atg gat gta ttc cac ttc atg gcc gac gac att ttc     350
Tyr Thr Cys His Met Asp Val Phe His Phe Met Ala Asp Asp Ile Phe
     80                  85                  90

agt gtc aac atc aca gac cag tct ggc aac tac tcc cag gag tgt ggc     398
Ser Val Asn Ile Thr Asp Gln Ser Gly Asn Tyr Ser Gln Glu Cys Gly
 95                 100                 105                 110

agc ttt ctc ctg gct gag agc atc aag ccg gct ccc cct ttc aac gtg     446
Ser Phe Leu Leu Ala Glu Ser Ile Lys Pro Ala Pro Pro Phe Asn Val
                115                 120                 125

act gtg acc ttc tca gga cag tat aat atc tcc tgg cgc tca gat tac     494
Thr Val Thr Phe Ser Gly Gln Tyr Asn Ile Ser Trp Arg Ser Asp Tyr
            130                 135                 140

gaa gac cct gcc ttc tac atg ctg aag ggc aag ctt cag tat gag ctg     542
Glu Asp Pro Ala Phe Tyr Met Leu Lys Gly Lys Leu Gln Tyr Glu Leu
        145                 150                 155

cag tac agg aac cgg gga gac ccc tgg gct gtg agt ccg agg aga aag     590
Gln Tyr Arg Asn Arg Gly Asp Pro Trp Ala Val Ser Pro Arg Arg Lys
    160                 165                 170

ctg atc tca gtg gac tca aga agt gtc tcc ctc ctc ccc ctg gag ttc     638
Leu Ile Ser Val Asp Ser Arg Ser Val Ser Leu Leu Pro Leu Glu Phe
175                 180                 185                 190

cgc aaa gac tcg agc tat gag ctg cag gtg cgg gca ggg ccc atg cct     686
Arg Lys Asp Ser Ser Tyr Glu Leu Gln Val Arg Ala Gly Pro Met Pro
                195                 200                 205

ggc tcc tcc tac cag ggg acc tgg agt gaa tgg agt gac ccg gtc atc     734
Gly Ser Ser Tyr Gln Gly Thr Trp Ser Glu Trp Ser Asp Pro Val Ile
            210                 215                 220

ttt cag acc cag tca gag gag tta aag gaa ggc tgg aac cct cac ctg     782
Phe Gln Thr Gln Ser Glu Glu Leu Lys Glu Gly Trp Asn Pro His Leu
        225                 230                 235

ctg ctt ctc ctc ctg ctt gtc ata gtc ttc att cct gcc ttc tgg agc     830
Leu Leu Leu Leu Leu Leu Val Ile Val Phe Ile Pro Ala Phe Trp Ser
    240                 245                 250
```

```
ctg aag acc cat cca ttg tgg agg cta tgg aag aag ata tgg gcc gtc      878
Leu Lys Thr His Pro Leu Trp Arg Leu Trp Lys Lys Ile Trp Ala Val
255                 260                 265                 270

ccc agc cct gag cgg ttc ttc atg ccc ctg tac aag ggc tgc agc gga      926
Pro Ser Pro Glu Arg Phe Phe Met Pro Leu Tyr Lys Gly Cys Ser Gly
                275                 280                 285

gac ttc aag aaa tgg gtg ggt gca ccc ttc act ggc tcc agc ctg gag      974
Asp Phe Lys Lys Trp Val Gly Ala Pro Phe Thr Gly Ser Ser Leu Glu
            290                 295                 300

ctg gga ccc tgg agc cca gag gtg ccc tcc acc ctg gag gtg tac agc     1022
Leu Gly Pro Trp Ser Pro Glu Val Pro Ser Thr Leu Glu Val Tyr Ser
        305                 310                 315

tgc cac cca cca cgg agc ccg gcc aag agg ctg cag ctc acg gag cta     1070
Cys His Pro Pro Arg Ser Pro Ala Lys Arg Leu Gln Leu Thr Glu Leu
    320                 325                 330

caa gaa cca gca gag ctg gtg gag tct gac ggt gtg ccc aag ccc agc     1118
Gln Glu Pro Ala Glu Leu Val Glu Ser Asp Gly Val Pro Lys Pro Ser
335                 340                 345                 350

ttc tgg ccg aca gcc cag aac tcg ggg ggc tca gct tac agt gag gag     1166
Phe Trp Pro Thr Ala Gln Asn Ser Gly Gly Ser Ala Tyr Ser Glu Glu
                355                 360                 365

agg gat cgg cca tac ggc ctg gtg tcc att gac aca gtg act gtg cta     1214
Arg Asp Arg Pro Tyr Gly Leu Val Ser Ile Asp Thr Val Thr Val Leu
            370                 375                 380

gat gca gag ggg cca tgc acc tgg ccc tgc agc tgt gag gat gac ggc     1262
Asp Ala Glu Gly Pro Cys Thr Trp Pro Cys Ser Cys Glu Asp Asp Gly
        385                 390                 395

tac cca gcc ctg gac ctg gat gct ggc ctg gag ccc agc cca ggc cta     1310
Tyr Pro Ala Leu Asp Leu Asp Ala Gly Leu Glu Pro Ser Pro Gly Leu
    400                 405                 410

gag gac cca ctc ttg gat gca ggg acc aca gtc ctg tcc tgt ggc tgt     1358
Glu Asp Pro Leu Leu Asp Ala Gly Thr Thr Val Leu Ser Cys Gly Cys
415                 420                 425                 430

gtc tca gct ggc agc cct ggg cta gga ggg ccc ctg gga agc ctc ctg     1406
Val Ser Ala Gly Ser Pro Gly Leu Gly Gly Pro Leu Gly Ser Leu Leu
                435                 440                 445

gac aga cta aag cca ccc ctt gca gat ggg gag gac tgg gct ggg gga     1454
Asp Arg Leu Lys Pro Pro Leu Ala Asp Gly Glu Asp Trp Ala Gly Gly
            450                 455                 460

ctg ccc tgg ggt ggc cgg tca cct gga ggg gtc tca gag agt gag gcg     1502
Leu Pro Trp Gly Gly Arg Ser Pro Gly Gly Val Ser Glu Ser Glu Ala
        465                 470                 475

ggc tca ccc ctg gcc ggc ctg gat atg gac acg ttt gac agt ggc ttt     1550
Gly Ser Pro Leu Ala Gly Leu Asp Met Asp Thr Phe Asp Ser Gly Phe
    480                 485                 490

gtg ggc tct gac tgc agc agc cct gtg gag tgt gac ttc acc agc ccc     1598
Val Gly Ser Asp Cys Ser Ser Pro Val Glu Cys Asp Phe Thr Ser Pro
495                 500                 505                 510

ggg gac gaa gga ccc ccc cgg agc tac ctc cgc cag tgg gtg gtc att     1646
Gly Asp Glu Gly Pro Pro Arg Ser Tyr Leu Arg Gln Trp Val Val Ile
                515                 520                 525

cct ccg cca ctt tcg agc cct gga ccc cag gcc agc taatgaggct          1692
Pro Pro Pro Leu Ser Ser Pro Gly Pro Gln Ala Ser
            530                 535

gactggatgt ccagagctgg ccaggccact gggccctgag ccagagacaa ggtcacctgg   1752

gctgtgatgt gaagacacct gcagcctttg gtctcctgga tgggcctttg agcctgatgt   1812

ttacagtgtc tgtgtgtgtg tgtgcatatg tgtgtgtgtg catatgcatg tgtgtgtgtg   1872

tgtgtgtctt aggtgcgcag tggcatgtcc acgtgtgtgt gtgattgcac gtgcctgtgg   1932
```

```
gcctgggata atgcccatgg tactccatgc attcacctgc cctgtgcatg tctggactca   1992

cggagctcac ccatgtgcac aagtgtgcac agtaaacgtg tttgtggtca acagatgaca   2052

acagccgtcc tccctcctag ggtcttgtgt tgcaagttgg tccacagcat ctccggggct   2112

ttgtgggatc agggcattgc ctgtgactga ggcggagccc agccctccag cgtctgcctc   2172

caggagctgc aagaagtcca tattgttcct tatcacctgc caacaggaag cgaaagggga   2232

tggagtgagc ccatggtgac ctcgggaatg gcaatttttt gggcggcccc tggacgaagg   2292

tctgaatccc gactctgata ccttctggct gtgctacctg agccaagtcg cctcccctct   2352

ctgggctaga gtttccttat ccagacagtg gggaaggcat gacacacctg ggggaaattg   2412

gcgatgtcac ccgtgtacgg tacgcagccc agagcagacc ctcaataaac gtcagcttcc   2472

ttccttctgc ggccagagcc gaggcgggcg ggggtgagaa catcaatcgt cagcgacagc   2532

ctgggcaccc gcggggccgt cccgcctgca gagggccact cggggggggtt tccaggctta   2592

aaatcagtcc gtttcgtctc ttggaaacag ctccccacca accaagattt ctttttctaa   2652

cttctgctac taagttttta aaaattccct ttatgcaccc aagagatatt tattaaacac   2712

caattacgta gcaggccatg gctcatggga cccacccccc gtggcactca tggagggggc   2772

tgcaggttgg aactatgcag tgtgctccgg ccacacatcc tgctgggccc cctaccctgc   2832

cccaattcaa tcctgccaat aaatcctgtc ttatttgttc atcctggaga attga        2887


<210> SEQ ID NO 2
<211> LENGTH: 538
<212> TYPE: PRT
<213> ORGANISM: Homo sapiens

<400> SEQUENCE: 2

Met Pro Arg Gly Trp Ala Ala Pro Leu Leu Leu Leu Leu Leu Gln Gly
 1               5                  10                  15

Gly Trp Gly Cys Pro Asp Leu Val Cys Tyr Thr Asp Tyr Leu Gln Thr
            20                  25                  30

Val Ile Cys Ile Leu Glu Met Trp Asn Leu His Pro Ser Thr Leu Thr
        35                  40                  45

Leu Thr Trp Gln Asp Gln Tyr Glu Glu Leu Lys Asp Glu Ala Thr Ser
    50                  55                  60

Cys Ser Leu His Arg Ser Ala His Asn Ala Thr His Ala Thr Tyr Thr
65                  70                  75                  80

Cys His Met Asp Val Phe His Phe Met Ala Asp Asp Ile Phe Ser Val
                85                  90                  95

Asn Ile Thr Asp Gln Ser Gly Asn Tyr Ser Gln Glu Cys Gly Ser Phe
            100                 105                 110

Leu Leu Ala Glu Ser Ile Lys Pro Ala Pro Pro Phe Asn Val Thr Val
        115                 120                 125

Thr Phe Ser Gly Gln Tyr Asn Ile Ser Trp Arg Ser Asp Tyr Glu Asp
    130                 135                 140

Pro Ala Phe Tyr Met Leu Lys Gly Lys Leu Gln Tyr Glu Leu Gln Tyr
145                 150                 155                 160

Arg Asn Arg Gly Asp Pro Trp Ala Val Ser Pro Arg Arg Lys Leu Ile
                165                 170                 175

Ser Val Asp Ser Arg Ser Val Ser Leu Leu Pro Leu Glu Phe Arg Lys
            180                 185                 190

Asp Ser Ser Tyr Glu Leu Gln Val Arg Ala Gly Pro Met Pro Gly Ser
        195                 200                 205
```

```
Ser Tyr Gln Gly Thr Trp Ser Glu Trp Ser Asp Pro Val Ile Phe Gln
    210                 215                 220

Thr Gln Ser Glu Glu Leu Lys Glu Gly Trp Asn Pro His Leu Leu Leu
225                 230                 235                 240

Leu Leu Leu Leu Val Ile Val Phe Ile Pro Ala Phe Trp Ser Leu Lys
                245                 250                 255

Thr His Pro Leu Trp Arg Leu Trp Lys Lys Ile Trp Ala Val Pro Ser
            260                 265                 270

Pro Glu Arg Phe Phe Met Pro Leu Tyr Lys Gly Cys Ser Gly Asp Phe
        275                 280                 285

Lys Lys Trp Val Gly Ala Pro Phe Thr Gly Ser Ser Leu Glu Leu Gly
    290                 295                 300

Pro Trp Ser Pro Glu Val Pro Ser Thr Leu Glu Val Tyr Ser Cys His
305                 310                 315                 320

Pro Pro Arg Ser Pro Ala Lys Arg Leu Gln Leu Thr Glu Leu Gln Glu
                325                 330                 335

Pro Ala Glu Leu Val Glu Ser Asp Gly Val Pro Lys Pro Ser Phe Trp
            340                 345                 350

Pro Thr Ala Gln Asn Ser Gly Gly Ser Ala Tyr Ser Glu Glu Arg Asp
        355                 360                 365

Arg Pro Tyr Gly Leu Val Ser Ile Asp Thr Val Thr Val Leu Asp Ala
    370                 375                 380

Glu Gly Pro Cys Thr Trp Pro Cys Ser Cys Glu Asp Asp Gly Tyr Pro
385                 390                 395                 400

Ala Leu Asp Leu Asp Ala Gly Leu Glu Pro Ser Pro Gly Leu Glu Asp
                405                 410                 415

Pro Leu Leu Asp Ala Gly Thr Thr Val Leu Ser Cys Gly Cys Val Ser
            420                 425                 430

Ala Gly Ser Pro Gly Leu Gly Gly Pro Leu Gly Ser Leu Leu Asp Arg
        435                 440                 445

Leu Lys Pro Pro Leu Ala Asp Gly Glu Asp Trp Ala Gly Gly Leu Pro
    450                 455                 460

Trp Gly Gly Arg Ser Pro Gly Gly Val Ser Glu Ser Glu Ala Gly Ser
465                 470                 475                 480

Pro Leu Ala Gly Leu Asp Met Asp Thr Phe Asp Ser Gly Phe Val Gly
                485                 490                 495

Ser Asp Cys Ser Ser Pro Val Glu Cys Asp Phe Thr Ser Pro Gly Asp
            500                 505                 510

Glu Gly Pro Pro Arg Ser Tyr Leu Arg Gln Trp Val Val Ile Pro Pro
        515                 520                 525

Pro Leu Ser Ser Pro Gly Pro Gln Ala Ser
    530                 535
```

```
<210> SEQ ID NO 3
<211> LENGTH: 5
<212> TYPE: PRT
<213> ORGANISM: Artificial Sequence
<220> FEATURE:
<223> OTHER INFORMATION: consensus amino acid motif
<220> FEATURE:
<221> NAME/KEY: VARIANT
<222> LOCATION: (1)...(5)
<223> OTHER INFORMATION: Xaa = Any Amino Acid
<220> FEATURE:
<221> NAME/KEY: VARIANT
<222> LOCATION: (1)...(5)
<223> OTHER INFORMATION: Xaa = Any Amino Acid

<400> SEQUENCE: 3
```

```
Trp Ser Xaa Trp Ser
 1               5


<210> SEQ ID NO 4
<211> LENGTH: 1614
<212> TYPE: DNA
<213> ORGANISM: Artificial Sequence
<220> FEATURE:
<223> OTHER INFORMATION: degenerate nucleotide sequence of zalpha11
<220> FEATURE:
<221> NAME/KEY: misc_feature
<222> LOCATION: (1)...(1614)
<223> OTHER INFORMATION: n = A,T,C or G
<220> FEATURE:
<221> NAME/KEY: misc_feature
<222> LOCATION: (1)...(1614)
<223> OTHER INFORMATION: n = A,T,C or G

<400> SEQUENCE: 4

atgccnmgng gntgggcngc nccnytnytn ytnytnytny tncarggngg ntggggntgy     60

ccngayytng tntgytayac ngaytayytn caracngtna thtgyathyt ngaratgtgg    120

aayytncayc cnwsnacnyt nacnytnacn tggcargayc artaygarga rytnaargay    180

gargcnacnw sntgywsnyt ncaymgnwsn gcncayaayg cnacncaygc nacntayacn    240

tgycayatgg aygtnttyca yttyatggcn gaygayatht tywsngtnaa yathacngay    300

carwsnggna aytaywsnca rgartgyggn wsnttyytny tngcngarws nathaarccn    360

gcnccnccnt tyaaygtnac ngtnacntty wsnggncart ayaayathws ntggmgnwsn    420

gaytaygarg ayccngcntt ytayatgytn aarggnaary tncartayga rytncartay    480

mgnaaymgng gngayccntg ggcngtnwsn ccnmgnmgna arytnathws ngtngaywsn    540

mgnwsngtnw snytnytncc nytngartty mgnaargayw snwsntayga rytncargtn    600

mgngcnggnc cnatgccngg nwsnwsntay carggnacnt ggwsngartg gwsngayccn    660

gtnathttyc aracncarws ngargarytn aargarggnt ggaayccnca yytnytnytn    720

ytnytnytny tngtnathgt nttyathccn gcnttytggw snytnaarac ncayccnytn    780

tggmgnytnt ggaaraarat htgggcngtn ccnwsnccng armgnttytt yatgccnytn    840

tayaarggnt gywsnggnga yttyaaraar tgggtnggng cnccnttyac nggnwsnwsn    900

ytngarytng gnccntggws nccngargtn ccnwsnacny tngargtnta ywsntgycay    960

ccnccnmgnw snccngcnaa rmgnytncar ytnacngary tncargarcc ngcngarytn   1020

gtngarwsng ayggngtncc naarccnwsn ttytggccna cngcncaraa ywsnggnggn   1080

wsngcntayw sngargarmg ngaymgnccn tayggnytng tnwsnathga yacngtnacn   1140

gtnytngayg cngarggncc ntgyacntgg ccntgywsnt gygargayga yggntayccn   1200

gcnytngayy tngaygcngg nytngarccn wsnccnggny tngargaycc nytnytngay   1260

gcnggnacna cngtnytnws ntgyggntgy gtnwsngcng gnwsnccngg nytnggnggn   1320

ccnytnggnw snytnytnga ymgnytnaar ccnccnytng cngayggnga rgaytgggcn   1380

ggnggnytnc cntggggngg nmgnwsnccn ggnggngtnw sngarwsnga rgcnggnwsn   1440

ccnytngcng gnytngayat ggayacntty gaywsnggnt tygtnggnws ngaytgywsn   1500

wsnccngtng artgygaytt yacnwsnccn ggngaygarg gnccnccnmg nwsntayytn   1560

mgncartggg tngtnathcc nccnccnytn wsnwsnccng gnccncargc nwsn         1614


<210> SEQ ID NO 5
<211> LENGTH: 17
<212> TYPE: DNA
```

<213> ORGANISM: Artificial Sequence
<220> FEATURE:
<223> OTHER INFORMATION: Oligonucleotide primer ZC447

<400> SEQUENCE: 5
taacaatttc acacagg 17

<210> SEQ ID NO 6
<211> LENGTH: 18
<212> TYPE: DNA
<213> ORGANISM: Artificial Sequence
<220> FEATURE:
<223> OTHER INFORMATION: Oligonucleotide primer ZC976

<400> SEQUENCE: 6
cgttgtaaaa cgacggcc 18

<210> SEQ ID NO 7
<211> LENGTH: 21
<212> TYPE: DNA
<213> ORGANISM: Artificial Sequence
<220> FEATURE:
<223> OTHER INFORMATION: Oligonucleotide primer ZC19345

<400> SEQUENCE: 7
gaccagtctg gcaactactc c 21

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide primer ZC19346

<400> SEQUENCE: 8
gctctcagcc aggagaaagc 20

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide primer ZC19349

<400> SEQUENCE: 9
ggttggtggg gagctgtttc 20

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide primer ZC19350

<400> SEQUENCE: 10
gggtgagaac atcaatcgtc 20

<210> SEQ ID NO 11
<211> LENGTH: 21
<212> TYPE: DNA
<213> ORGANISM: Artificial Sequence
<220> FEATURE:
<223> OTHER INFORMATION: Oligonucleotide primer ZC19458

<400> SEQUENCE: 11
catatcttct tccatagcct c 21

<210> SEQ ID NO 12
<211> LENGTH: 21
<212> TYPE: DNA
<213> ORGANISM: Artificial Sequence
<220> FEATURE:
<223> OTHER INFORMATION: Oligonucleotide primer ZC19459

<400> SEQUENCE: 12
ctcctcctgc ttgtcatagt c 21

<210> SEQ ID NO 13
<211> LENGTH: 21
<212> TYPE: DNA
<213> ORGANISM: Artificial Sequence
<220> FEATURE:
<223> OTHER INFORMATION: Oligonucleotide primer ZC19460

<400> SEQUENCE: 13
gtaaacgtgt ttgtggtcaa c 21

<210> SEQ ID NO 14
<211> LENGTH: 20
<212> TYPE: DNA
<213> ORGANISM: Artificial Sequence
<220> FEATURE:
<223> OTHER INFORMATION: Oligonucleotide primer ZC19461

<400> SEQUENCE: 14
tgccctgatc ccacaaagcc 20

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide primer ZC19572

<400> SEQUENCE: 15
gtcctgtggc tgtgtctcag 20

<210> SEQ ID NO 16
<211> LENGTH: 20
<212> TYPE: DNA
<213> ORGANISM: Artificial Sequence
<220> FEATURE:
<223> OTHER INFORMATION: Oligonucleotide primer ZC19573

<400> SEQUENCE: 16
cagtcagagc ccacaaagcc 20

<210> SEQ ID NO 17
<211> LENGTH: 20
<212> TYPE: DNA
<213> ORGANISM: Artificial Sequence
<220> FEATURE:
<223> OTHER INFORMATION: Oligonucleotide primer ZC19657

<400> SEQUENCE: 17
ctgagacaca gccacaggac 20

<210> SEQ ID NO 18
<211> LENGTH: 24
<212> TYPE: DNA
<213> ORGANISM: Artificial Sequence
<220> FEATURE:
<223> OTHER INFORMATION: Oligonucleotide primer ZC19181

```
<400> SEQUENCE: 18

tccacatccc tagggctctg tgat                                          24


<210> SEQ ID NO 19
<211> LENGTH: 25
<212> TYPE: DNA
<213> ORGANISM: Artificial Sequence
<220> FEATURE:
<223> OTHER INFORMATION: Oligonucleotide primer ZC19182

<400> SEQUENCE: 19

gaggttccac atttccagga tgcag                                         25


<210> SEQ ID NO 20
<211> LENGTH: 24
<212> TYPE: DNA
<213> ORGANISM: Artificial Sequence
<220> FEATURE:
<223> OTHER INFORMATION: Oligonucleotide primer ZC19907

<400> SEQUENCE: 20

atggatgtat tccacttcat ggcc                                          24


<210> SEQ ID NO 21
<211> LENGTH: 24
<212> TYPE: DNA
<213> ORGANISM: Artificial Sequence
<220> FEATURE:
<223> OTHER INFORMATION: Oligonucleotide primer ZC19908

<400> SEQUENCE: 21

actgtcaaac gtgtccatat ccag                                          24


<210> SEQ ID NO 22
<211> LENGTH: 18
<212> TYPE: DNA
<213> ORGANISM: Artificial Sequence
<220> FEATURE:
<223> OTHER INFORMATION: Oligonucleotide primer ZC19954

<400> SEQUENCE: 22

actgggctgg gggactgc                                                 18


<210> SEQ ID NO 23
<211> LENGTH: 18
<212> TYPE: DNA
<213> ORGANISM: Artificial Sequence
<220> FEATURE:
<223> OTHER INFORMATION: Oligonucleotide primer ZC19955

<400> SEQUENCE: 23

ccccggggct ggtgaagt                                                 18


<210> SEQ ID NO 24
<211> LENGTH: 33
<212> TYPE: DNA
<213> ORGANISM: Artificial Sequence
<220> FEATURE:
<223> OTHER INFORMATION: Oligonucleotide primer ZC17212

<400> SEQUENCE: 24

ggggaattcg aagccatgcc ctcttgggcc ctc                                33


<210> SEQ ID NO 25
<211> LENGTH: 30
<212> TYPE: DNA
```

<213> ORGANISM: Artificial Sequence
<220> FEATURE:
<223> OTHER INFORMATION: Oligonucleotide primer ZC19914

<400> SEQUENCE: 25
caatggatgg gtctttagca gcagtaggcc 30

<210> SEQ ID NO 26
<211> LENGTH: 30
<212> TYPE: DNA
<213> ORGANISM: Artificial Sequence
<220> FEATURE:
<223> OTHER INFORMATION: Oligonucleotide primer ZC19913

<400> SEQUENCE: 26
ggcctactgc tgctaaagac ccatccattg 30

<210> SEQ ID NO 27
<211> LENGTH: 33
<212> TYPE: DNA
<213> ORGANISM: Artificial Sequence
<220> FEATURE:
<223> OTHER INFORMATION: Oligonucleotide primer ZC20097

<400> SEQUENCE: 27
acatctagat tagctggcct ggggtccagg cgt 33

<210> SEQ ID NO 28
<211> LENGTH: 21
<212> TYPE: DNA
<213> ORGANISM: Artificial Sequence
<220> FEATURE:
<223> OTHER INFORMATION: Oligonucleotide primer ZC12700

<400> SEQUENCE: 28
ggaggtctat ataagcagag c 21

<210> SEQ ID NO 29
<211> LENGTH: 21
<212> TYPE: DNA
<213> ORGANISM: Artificial Sequence
<220> FEATURE:
<223> OTHER INFORMATION: Oligonucleotide primer ZC5020

<400> SEQUENCE: 29
cactggagtg gcaacttcca g 21

<210> SEQ ID NO 30
<211> LENGTH: 20
<212> TYPE: DNA
<213> ORGANISM: Artificial Sequence
<220> FEATURE:
<223> OTHER INFORMATION: Oligonucleotide primer ZC6675

<400> SEQUENCE: 30
gtggatgccg aacccagtcc 20

<210> SEQ ID NO 31
<211> LENGTH: 21
<212> TYPE: DNA
<213> ORGANISM: Artificial Sequence
<220> FEATURE:
<223> OTHER INFORMATION: Oligonucleotide primer ZC7727

<400> SEQUENCE: 31
tgttcacagc tacctgggct c 21

<210> SEQ ID NO 32
<211> LENGTH: 26
<212> TYPE: DNA
<213> ORGANISM: Artificial Sequence
<220> FEATURE:
<223> OTHER INFORMATION: Oligonucleotide primer ZC8290

<400> SEQUENCE: 32
ccaccgagac tgcttggatc accttg 26

<210> SEQ ID NO 33
<211> LENGTH: 21
<212> TYPE: DNA
<213> ORGANISM: Artificial Sequence
<220> FEATURE:
<223> OTHER INFORMATION: Oligonucleotide primer ZC6622

<400> SEQUENCE: 33
ctgggctgga aactggcaca c 21

<210> SEQ ID NO 34
<211> LENGTH: 18
<212> TYPE: DNA
<213> ORGANISM: Artificial Sequence
<220> FEATURE:
<223> OTHER INFORMATION: Oligonucleotide primer ZC7736

<400> SEQUENCE: 34
cactgtcaga aatggagc 18

<210> SEQ ID NO 35
<211> LENGTH: 24
<212> TYPE: DNA
<213> ORGANISM: Artificial Sequence
<220> FEATURE:
<223> OTHER INFORMATION: Oligonucleotide primer ZC9273

<400> SEQUENCE: 35
ggtccctccc cgggcaccga gaga 24

<210> SEQ ID NO 36
<211> LENGTH: 36
<212> TYPE: DNA
<213> ORGANISM: Artificial Sequence
<220> FEATURE:
<223> OTHER INFORMATION: Oligonucleotide primer ZC19905

<400> SEQUENCE: 36
acaggatccg tcagcatgcc gcgtggctgg gccgcc 36

<210> SEQ ID NO 37
<211> LENGTH: 33
<212> TYPE: DNA
<213> ORGANISM: Artificial Sequence
<220> FEATURE:
<223> OTHER INFORMATION: Oligonucleotide primer ZC19906

<400> SEQUENCE: 37
acagaattct tagctggcct ggggtccagg cgt 33

<210> SEQ ID NO 38
<211> LENGTH: 22
<212> TYPE: DNA
<213> ORGANISM: Artificial Sequence
<220> FEATURE:
<223> OTHER INFORMATION: Oligonucleotide primer ZC20114

<400> SEQUENCE: 38
cctgccttct acatgctgaa gg 22

<210> SEQ ID NO 39
<211> LENGTH: 18
<212> TYPE: DNA
<213> ORGANISM: Artificial Sequence
<220> FEATURE:
<223> OTHER INFORMATION: Oligonucleotide primer ZC19954

<400> SEQUENCE: 39
actgggctgg gggactgc 18

<210> SEQ ID NO 40
<211> LENGTH: 22
<212> TYPE: DNA
<213> ORGANISM: Artificial Sequence
<220> FEATURE:
<223> OTHER INFORMATION: Oligonucleotide primer ZC20116

<400> SEQUENCE: 40
agcacagtca ctgtgtcaat gg 22

<210> SEQ ID NO 41
<211> LENGTH: 6
<212> TYPE: PRT
<213> ORGANISM: Artificial Sequence
<220> FEATURE:
<223> OTHER INFORMATION: Glu-Glu (CEE) tag amino acid sequence

<400> SEQUENCE: 41

Glu Tyr Met Pro Met Glu
1 5

<210> SEQ ID NO 42
<211> LENGTH: 36
<212> TYPE: DNA
<213> ORGANISM: Artificial Sequence
<220> FEATURE:
<223> OTHER INFORMATION: Oligonucleotide promer ZC19931

<400> SEQUENCE: 42
ggttggtacc gcaagatgcc gcgtggctgg gccgcc 36

<210> SEQ ID NO 43
<211> LENGTH: 29
<212> TYPE: DNA
<213> ORGANISM: Artificial Sequence
<220> FEATURE:
<223> OTHER INFORMATION: Oligonucleotide primer ZC19932

<400> SEQUENCE: 43
cggaggatcc gtgagggttc cagccttcc 29

<210> SEQ ID NO 44
<211> LENGTH: 66
<212> TYPE: DNA
<213> ORGANISM: Artificial Sequence
<220> FEATURE:
<223> OTHER INFORMATION: Oligonucleotide primer spanning vector flanking region and the 5' end of the zalpha11

<400> SEQUENCE: 44
tccactttgc ctttctctcc acaggtgtcc agggaattca tcgataatgc cgcgtggctg 60
ggccgc 66

<210> SEQ ID NO 45
<211> LENGTH: 699
<212> TYPE: DNA
<213> ORGANISM: Homo sapiens

<400> SEQUENCE: 45

```
gagcccagat cttcagacaa aactcacaca tgcccaccgt gcccagcacc tgaagccgag     60

ggggcaccgt cagtcttcct cttcccccca aaacccaagg acaccctcat gatctcccgg    120

acccctgagg tcacatgcgt ggtggtggac gtgagccacg aagaccctga ggtcaagttc    180

aactggtacg tggacggcgt ggaggtgcat aatgccaaga caaagccgcg ggaggagcag    240

tacaacagca cgtaccgtgt ggtcagcgtc ctcaccgtcc tgcaccagga ctggctgaat    300

ggcaaggagt acaagtgcaa ggtctccaac aaagccctcc catcctccat cgagaaaacc    360

atctccaaag ccaaagggca gccccgagaa ccacaggtgt acaccctgcc cccatcccgg    420

gatgagctga ccaagaacca ggtcagcctg acctgcctgg tcaaaggctt ctatcccagc    480

gacatcgccg tggagtggga gagcaatggg cagccggaga acaactacaa gaccacgcct    540

cccgtgctgg actccgacgg ctccttcttc ctctacagca agctcaccgt ggacaagagc    600

aggtggcagc aggggaacgt cttctcatgc tccgtgatgc atgaggctct gcacaaccac    660

tacacgcaga agagcctctc cctgtctccg ggtaaataa                           699
```

<210> SEQ ID NO 46
<211> LENGTH: 62
<212> TYPE: DNA
<213> ORGANISM: Artificial Sequence
<220> FEATURE:
<223> OTHER INFORMATION: First Oligonucleotide primer spanning 3' end of the zalpha11 extracellular domain and the 5' end of Fc4

<400> SEQUENCE: 46

```
gcacggtggg catgtgtgag ttttgtctga agatctgggc tcgtgagggt tccagccttc     60

ct                                                                    62
```

<210> SEQ ID NO 47
<211> LENGTH: 61
<212> TYPE: DNA
<213> ORGANISM: Artificial Sequence
<220> FEATURE:
<223> OTHER INFORMATION: Second Oligonucleotide primer spanning 3' end of the zalpha11 extracellular domain and the 5' end of Fc4

<400> SEQUENCE: 47

```
agacccagtc agaggagtta aaggaaggct ggaaccctca cgagcccaga tcttcagaca     60

a                                                                     61
```

<210> SEQ ID NO 48
<211> LENGTH: 67
<212> TYPE: DNA
<213> ORGANISM: Artificial Sequence
<220> FEATURE:
<223> OTHER INFORMATION: Oligonucleotide primer spanning the 3' end of Fc4 and the vector flanking region

<400> SEQUENCE: 48

```
gtgggcctct ggggtgggta caaccccaga gctgttttaa tctagattat ttacccggag     60

acaggga                                                               67
```

```
<210> SEQ ID NO 49
<211> LENGTH: 8
<212> TYPE: PRT
<213> ORGANISM: Artificial Sequence
<220> FEATURE:
<223> OTHER INFORMATION: FLAG tag amino acid sequence

<400> SEQUENCE: 49

Asp Tyr Lys Asp Asp Asp Asp Lys
 1              5


<210> SEQ ID NO 50
<211> LENGTH: 1821
<212> TYPE: DNA
<213> ORGANISM: Artificial Sequence
<220> FEATURE:
<223> OTHER INFORMATION: Polynucleotide encoding MBP-zalpha11 soluble
      receptor fusion
<220> FEATURE:
<221> NAME/KEY: CDS
<222> LOCATION: (1)...(1821)

<400> SEQUENCE: 50

atg aaa atc gaa gaa ggt aaa ctg gta atc tgg att aac ggc gat aaa       48
Met Lys Ile Glu Glu Gly Lys Leu Val Ile Trp Ile Asn Gly Asp Lys
 1               5                  10                  15

ggc tat aac ggt ctc gct gaa gtc ggt aag aaa ttc gag aaa gat acc       96
Gly Tyr Asn Gly Leu Ala Glu Val Gly Lys Lys Phe Glu Lys Asp Thr
             20                  25                  30

gga att aaa gtc acc gtt gag cat ccg gat aaa ctg gaa gag aaa ttc      144
Gly Ile Lys Val Thr Val Glu His Pro Asp Lys Leu Glu Glu Lys Phe
         35                  40                  45

cca cag gtt gcg gca act ggc gat ggc cct gac att atc ttc tgg gca      192
Pro Gln Val Ala Ala Thr Gly Asp Gly Pro Asp Ile Ile Phe Trp Ala
     50                  55                  60

cac gac cgc ttt ggt ggc tac gct caa tct ggc ctg ttg gct gaa atc      240
His Asp Arg Phe Gly Gly Tyr Ala Gln Ser Gly Leu Leu Ala Glu Ile
 65                  70                  75                  80

acc ccg gac aaa gcg ttc cag gac aag ctg tat ccg ttt acc tgg gat      288
Thr Pro Asp Lys Ala Phe Gln Asp Lys Leu Tyr Pro Phe Thr Trp Asp
                 85                  90                  95

gcc gta cgt tac aac ggc aag ctg att gct tac ccg atc gct gtt gaa      336
Ala Val Arg Tyr Asn Gly Lys Leu Ile Ala Tyr Pro Ile Ala Val Glu
            100                 105                 110

gcg tta tcg ctg att tat aac aaa gat ctg ctg ccg aac ccg cca aaa      384
Ala Leu Ser Leu Ile Tyr Asn Lys Asp Leu Leu Pro Asn Pro Pro Lys
        115                 120                 125

acc tgg gaa gag atc ccg gcg ctg gat aaa gaa ctg aaa gcg aaa ggt      432
Thr Trp Glu Glu Ile Pro Ala Leu Asp Lys Glu Leu Lys Ala Lys Gly
    130                 135                 140

aag agc gcg ctg atg ttc aac ctg caa gaa ccg tac ttc acc tgg ccg      480
Lys Ser Ala Leu Met Phe Asn Leu Gln Glu Pro Tyr Phe Thr Trp Pro
145                 150                 155                 160

ctg att gct gct gac ggg ggt tat gcg ttc aag tat gaa aac ggc aag      528
Leu Ile Ala Ala Asp Gly Gly Tyr Ala Phe Lys Tyr Glu Asn Gly Lys
                165                 170                 175

tac gac att aaa gac gtg ggc gtg gat aac gct ggc gcg aaa gcg ggt      576
Tyr Asp Ile Lys Asp Val Gly Val Asp Asn Ala Gly Ala Lys Ala Gly
            180                 185                 190

ctg acc ttc ctg gtt gac ctg att aaa aac aaa cac atg aat gca gac      624
Leu Thr Phe Leu Val Asp Leu Ile Lys Asn Lys His Met Asn Ala Asp
        195                 200                 205

acc gat tac tcc atc gca gaa gct gcc ttt aat aaa ggc gaa aca gcg      672
Thr Asp Tyr Ser Ile Ala Glu Ala Ala Phe Asn Lys Gly Glu Thr Ala
```

-continued

```
    210                 215                 220

atg acc atc aac ggc ccg tgg gca tgg tcc aac atc gac acc agc aaa      720
Met Thr Ile Asn Gly Pro Trp Ala Trp Ser Asn Ile Asp Thr Ser Lys
225                 230                 235                 240

gtg aat tat ggt gta acg gta ctg ccg acc ttc aag ggt caa cca tcc      768
Val Asn Tyr Gly Val Thr Val Leu Pro Thr Phe Lys Gly Gln Pro Ser
                245                 250                 255

aaa ccg ttc gtt ggc gtg ctg agc gca ggt att aac gcc gcc agt ccg      816
Lys Pro Phe Val Gly Val Leu Ser Ala Gly Ile Asn Ala Ala Ser Pro
            260                 265                 270

aac aaa gag ctg gca aaa gag ttc ctc gaa aac tat ctg ctg act gat      864
Asn Lys Glu Leu Ala Lys Glu Phe Leu Glu Asn Tyr Leu Leu Thr Asp
        275                 280                 285

gaa ggt ctg gaa gcg gtt aat aaa gac aaa ccg ctg ggt gcc gta gcg      912
Glu Gly Leu Glu Ala Val Asn Lys Asp Lys Pro Leu Gly Ala Val Ala
    290                 295                 300

ctg aag tct tac gag gaa gag ttg gcg aaa gat cca cgt att gcc gcc      960
Leu Lys Ser Tyr Glu Glu Glu Leu Ala Lys Asp Pro Arg Ile Ala Ala
305                 310                 315                 320

acc atg gaa aac gcc cag aaa ggt gaa atc atg ccg aac atc ccg cag     1008
Thr Met Glu Asn Ala Gln Lys Gly Glu Ile Met Pro Asn Ile Pro Gln
                325                 330                 335

atg tcc gct ttc tgg tat gcc gtg cgt act gcg gtg atc aac gcc gcc     1056
Met Ser Ala Phe Trp Tyr Ala Val Arg Thr Ala Val Ile Asn Ala Ala
            340                 345                 350

agc ggt cgt cag act gtc gat gaa gcc ctg aaa gac gcg cag act aat     1104
Ser Gly Arg Gln Thr Val Asp Glu Ala Leu Lys Asp Ala Gln Thr Asn
        355                 360                 365

tcg agc tcc cac cat cac cat cac cac gcg aat tcg gta ccg ctg gtt     1152
Ser Ser Ser His His His His His His Ala Asn Ser Val Pro Leu Val
    370                 375                 380

ccg cgt gga tcc tgc ccc gac ctc gtc tgc tac acc gat tac ctc cag     1200
Pro Arg Gly Ser Cys Pro Asp Leu Val Cys Tyr Thr Asp Tyr Leu Gln
385                 390                 395                 400

acg gtc atc tgc atc ctg gaa atg tgg aac ctc cac ccc agc acg ctc     1248
Thr Val Ile Cys Ile Leu Glu Met Trp Asn Leu His Pro Ser Thr Leu
                405                 410                 415

acc ctt acc tgg caa gac cag tat gaa gag ctg aag gac gag gcc acc     1296
Thr Leu Thr Trp Gln Asp Gln Tyr Glu Glu Leu Lys Asp Glu Ala Thr
            420                 425                 430

tcc tgc agc ctc cac agg tcg gcc cac aat gcc acg cat gcc acc tac     1344
Ser Cys Ser Leu His Arg Ser Ala His Asn Ala Thr His Ala Thr Tyr
        435                 440                 445

acc tgc cac atg gat gta ttc cac ttc atg gcc gac gac att ttc agt     1392
Thr Cys His Met Asp Val Phe His Phe Met Ala Asp Asp Ile Phe Ser
    450                 455                 460

gtc aac atc aca gac cag tct ggc aac tac tcc cag gag tgt ggc agc     1440
Val Asn Ile Thr Asp Gln Ser Gly Asn Tyr Ser Gln Glu Cys Gly Ser
465                 470                 475                 480

ttt ctc ctg gct gag agc atc aag ccg gct ccc cct ttc aac gtg act     1488
Phe Leu Leu Ala Glu Ser Ile Lys Pro Ala Pro Pro Phe Asn Val Thr
                485                 490                 495

gtg acc ttc tca gga cag tat aat atc tcc tgg cgc tca gat tac gaa     1536
Val Thr Phe Ser Gly Gln Tyr Asn Ile Ser Trp Arg Ser Asp Tyr Glu
            500                 505                 510

gac cct gcc ttc tac atg ctg aag ggc aag ctt cag tat gag ctg cag     1584
Asp Pro Ala Phe Tyr Met Leu Lys Gly Lys Leu Gln Tyr Glu Leu Gln
        515                 520                 525

tac agg aac cgg gga gac ccc tgg gct gtg agt ccg agg aga aag ctg     1632
Tyr Arg Asn Arg Gly Asp Pro Trp Ala Val Ser Pro Arg Arg Lys Leu
```

```
    530                 535                 540

atc tca gtg gac tca aga agt gtc tcc ctc ctc ccc ctg gag ttc cgc      1680
Ile Ser Val Asp Ser Arg Ser Val Ser Leu Leu Pro Leu Glu Phe Arg
545                 550                 555                 560

aaa gac tcg agc tat gag ctg cag gtg cgg gca ggg ccc atg cct ggc      1728
Lys Asp Ser Ser Tyr Glu Leu Gln Val Arg Ala Gly Pro Met Pro Gly
                565                 570                 575

tcc tcc tac cag ggg acc tgg agt gaa tgg agt gac ccg gtc atc ttt      1776
Ser Ser Tyr Gln Gly Thr Trp Ser Glu Trp Ser Asp Pro Val Ile Phe
            580                 585                 590

cag acc cag tca gag gag tta aag gaa ggc tgg aac cct cac tag          1821
Gln Thr Gln Ser Glu Glu Leu Lys Glu Gly Trp Asn Pro His  *
        595                 600                 605


<210> SEQ ID NO 51
<211> LENGTH: 606
<212> TYPE: PRT
<213> ORGANISM: Artificial Sequence
<220> FEATURE:
<223> OTHER INFORMATION: Polynucleotide encoding MBP-zalpha11 soluble
      receptor fusion

<400> SEQUENCE: 51

Met Lys Ile Glu Glu Gly Lys Leu Val Ile Trp Ile Asn Gly Asp Lys
 1               5                  10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270
```

```
Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser His His His His His His Ala Asn Ser Val Pro Leu Val
    370                 375                 380

Pro Arg Gly Ser Cys Pro Asp Leu Val Cys Tyr Thr Asp Tyr Leu Gln
385                 390                 395                 400

Thr Val Ile Cys Ile Leu Glu Met Trp Asn Leu His Pro Ser Thr Leu
                405                 410                 415

Thr Leu Thr Trp Gln Asp Gln Tyr Glu Glu Leu Lys Asp Glu Ala Thr
            420                 425                 430

Ser Cys Ser Leu His Arg Ser Ala His Asn Ala Thr His Ala Thr Tyr
        435                 440                 445

Thr Cys His Met Asp Val Phe His Phe Met Ala Asp Asp Ile Phe Ser
    450                 455                 460

Val Asn Ile Thr Asp Gln Ser Gly Asn Tyr Ser Gln Glu Cys Gly Ser
465                 470                 475                 480

Phe Leu Leu Ala Glu Ser Ile Lys Pro Ala Pro Pro Phe Asn Val Thr
                485                 490                 495

Val Thr Phe Ser Gly Gln Tyr Asn Ile Ser Trp Arg Ser Asp Tyr Glu
            500                 505                 510

Asp Pro Ala Phe Tyr Met Leu Lys Gly Lys Leu Gln Tyr Glu Leu Gln
        515                 520                 525

Tyr Arg Asn Arg Gly Asp Pro Trp Ala Val Ser Pro Arg Arg Lys Leu
    530                 535                 540

Ile Ser Val Asp Ser Arg Ser Val Ser Leu Leu Pro Leu Glu Phe Arg
545                 550                 555                 560

Lys Asp Ser Ser Tyr Glu Leu Gln Val Arg Ala Gly Pro Met Pro Gly
                565                 570                 575

Ser Ser Tyr Gln Gly Thr Trp Ser Glu Trp Ser Asp Pro Val Ile Phe
            580                 585                 590

Gln Thr Gln Ser Glu Glu Leu Lys Glu Gly Trp Asn Pro His
        595                 600                 605
```

<210> SEQ ID NO 52
<211> LENGTH: 657
<212> TYPE: DNA
<213> ORGANISM: Homo sapiens

<400> SEQUENCE: 52

```
tgccccgacc tcgtctgcta caccgattac ctccagacgg tcatctgcat cctggaaatg     60

tggaacctcc accccagcac gctcaccctt acctggcaag accagtatga agagctgaag    120

gacgaggcca cctcctgcag cctccacagg tcggcccaca atgccacgca tgccacctac    180

acctgccaca tggatgtatt ccacttcatg gccgacgaca ttttcagtgt caacatcaca    240

gaccagtctg gcaactactc ccaggagtgt ggcagctttc tcctggctga gagcatcaag    300
```

ccggctcccc ctttcaacgt gactgtgacc ttctcaggac agtataatat ctcctggcgc 360
tcagattacg aagaccctgc cttctacatg ctgaagggca agcttcagta tgagctgcag 420
tacaggaacc ggggagaccc ctgggctgtg agtccgagga gaaagctgat ctcagtggac 480
tcaagaagtg tctccctcct ccccctggag ttccgcaaag actcgagcta tgagctgcag 540
gtgcgggcag ggcccatgcc tggctcctcc taccagggga cctggagtga atggagtgac 600
ccggtcatct ttcagaccca gtcagaggag ttaaaggaag gctggaaccc tcactag 657

<210> SEQ ID NO 53
<211> LENGTH: 65
<212> TYPE: DNA
<213> ORGANISM: Artificial Sequence
<220> FEATURE:
<223> OTHER INFORMATION: Oligonucleotide primer ZC20187

<400> SEQUENCE: 53
tcaccacgcg aattcggtac cgctggttcc gcgtggatcc tgccccgacc tcgtctgcta 60
caccg 65

<210> SEQ ID NO 54
<211> LENGTH: 68
<212> TYPE: DNA
<213> ORGANISM: Artificial Sequence
<220> FEATURE:
<223> OTHER INFORMATION: Oligonucleotide primer ZC20185

<400> SEQUENCE: 54
tctgtatcag gctgaaaatc ttatctcatc cgccaaaaca ctagtgaggg ttccagcctt 60
cctttaac 68

<210> SEQ ID NO 55
<211> LENGTH: 40
<212> TYPE: DNA
<213> ORGANISM: Artificial Sequence
<220> FEATURE:
<223> OTHER INFORMATION: Oligonucleotide primer ZC19372

<400> SEQUENCE: 55
tgtcgatgaa gccctgaaag acgcgcagac taattcgagc 40

<210> SEQ ID NO 56
<211> LENGTH: 60
<212> TYPE: DNA
<213> ORGANISM: Artificial Sequence
<220> FEATURE:
<223> OTHER INFORMATION: Oligonucleotide primer ZC19351

<400> SEQUENCE: 56
acgcgcagac taattcgagc tcccaccatc accatcacca cgcgaattcg gtaccgctgg 60

<210> SEQ ID NO 57
<211> LENGTH: 60
<212> TYPE: DNA
<213> ORGANISM: Artificial Sequence
<220> FEATURE:
<223> OTHER INFORMATION: Oligonucleotide primer ZC19352

<400> SEQUENCE: 57
actcactata gggcgaattg cccgggggat ccacgcggaa ccagcggtac cgaattcgcg 60

<210> SEQ ID NO 58
<211> LENGTH: 42

```
<212> TYPE: DNA
<213> ORGANISM: Artificial Sequence
<220> FEATURE:
<223> OTHER INFORMATION: Oligonucleotide primer ZC19371

<400> SEQUENCE: 58

acggccagtg aattgtaata cgactcacta tagggcgaat tg                         42


<210> SEQ ID NO 59
<211> LENGTH: 20
<212> TYPE: DNA
<213> ORGANISM: Artificial Sequence
<220> FEATURE:
<223> OTHER INFORMATION: Oligonucleotide primer ZC22277

<400> SEQUENCE: 59

ccaggagtgt ggcagctttc                                                  20


<210> SEQ ID NO 60
<211> LENGTH: 21
<212> TYPE: DNA
<213> ORGANISM: Artificial Sequence
<220> FEATURE:
<223> OTHER INFORMATION: Oligonucleotide primer ZC22276

<400> SEQUENCE: 60

gcttgccctt cagcatgtag a                                                21


<210> SEQ ID NO 61
<211> LENGTH: 23
<212> TYPE: DNA
<213> ORGANISM: Artificial Sequence
<220> FEATURE:
<223> OTHER INFORMATION: zalpha11 TaqMan probe, ZG31

<400> SEQUENCE: 61

cggctccccc tttcaacgtg act                                              23


<210> SEQ ID NO 62
<211> LENGTH: 20
<212> TYPE: DNA
<213> ORGANISM: Artificial Sequence
<220> FEATURE:
<223> OTHER INFORMATION: Oligonucleotide primer ZC23684

<400> SEQUENCE: 62

tcacccttac ctggcaagac                                                  20


<210> SEQ ID NO 63
<211> LENGTH: 41
<212> TYPE: DNA
<213> ORGANISM: Artificial Sequence
<220> FEATURE:
<223> OTHER INFORMATION: Oligonucleotide primer ZC23656

<400> SEQUENCE: 63

taatacgact cactataggg agggggagac acttcttgag t                          41


<210> SEQ ID NO 64
<211> LENGTH: 20
<212> TYPE: DNA
<213> ORGANISM: Artificial Sequence
<220> FEATURE:
<223> OTHER INFORMATION: Oligonucleotide primer ZC23685

<400> SEQUENCE: 64

aggtctgaat cccgactctg                                                  20
```

<210> SEQ ID NO 65
<211> LENGTH: 41
<212> TYPE: DNA
<213> ORGANISM: Artificial Sequence
<220> FEATURE:
<223> OTHER INFORMATION: Oligonucleotide primer ZC23657

<400> SEQUENCE: 65
taatacgact cactataggg aggacgtaat tggtgtttaa t 41

<210> SEQ ID NO 66
<211> LENGTH: 20
<212> TYPE: DNA
<213> ORGANISM: Artificial Sequence
<220> FEATURE:
<223> OTHER INFORMATION: Oligonucleotide primer, rRNA forward primer

<400> SEQUENCE: 66
cggctaccac atccaaggaa 20

<210> SEQ ID NO 67
<211> LENGTH: 18
<212> TYPE: DNA
<213> ORGANISM: Artificial Sequence
<220> FEATURE:
<223> OTHER INFORMATION: Oligonucleotide primer, rRNA reverse primer

<400> SEQUENCE: 67
gctggaatta ccgcggct 18

<210> SEQ ID NO 68
<211> LENGTH: 22
<212> TYPE: DNA
<213> ORGANISM: Artificial Sequence
<220> FEATURE:
<223> OTHER INFORMATION: rRNA TaqMan probe

<400> SEQUENCE: 68
tgctggcacc agacttgccc tc 22

<210> SEQ ID NO 69
<211> LENGTH: 1298
<212> TYPE: DNA
<213> ORGANISM: Mus musculus
<220> FEATURE:
<221> NAME/KEY: CDS
<222> LOCATION: (543)...(1262)

<400> SEQUENCE: 69
aggcctttca acacggcttt ttagtaattc attccatcta taaacattta tggtacacct 60
actgtgtgcc aggtactgag gacacagttg tgatcagggc tagtgtagac acacaagcaa 120
aactagagac atccggaagt gtcaggagac ggagtagagg ctgggccact tagacctcag 180
gctctccctg cacacgtcct caagacctta ggacttagga acctggtccc agcacccagc 240
tgttccttgg ctggggcact ggtaactagc gtggatatga gacagaggac agtcagtcct 300
tactaaaggt gggaacacgg gctctgagaa cggacagtat tgggaaccca ctgggcaggg 360
ggttcacaga cagacatcat ggcgcgctct ctctctctct ctctctcctg ttttcttgtt 420
cttctgcttt ccccgtctct ggcttgtccc tgtactcccc cccccacccc catctttggc 480
tctctctgtt cacacccgac cttgttgtcc ccagctcatg actgtgtgtt tctttctcat 540 ag aaa tgg gtt aat acc cct ttc acg gcc tcc agc ata gag ttg gtg 587
Lys Trp Val Asn Thr Pro Phe Thr Ala Ser Ser Ile Glu Leu Val

```
 1               5                  10                 15

cca cag agt tcc aca aca aca tca gcc tta cat ctg tca ttg tat cca      635
Pro Gln Ser Ser Thr Thr Thr Ser Ala Leu His Leu Ser Leu Tyr Pro
                20                  25                  30

gcc aag gag aag aag ttc ccg ggg ctg ccg ggt ctg gaa gag caa ctg      683
Ala Lys Glu Lys Lys Phe Pro Gly Leu Pro Gly Leu Glu Glu Gln Leu
            35                  40                  45

gag tgt gat gga atg tct gag cct ggt cac tgg tgc ata atc ccc ttg      731
Glu Cys Asp Gly Met Ser Glu Pro Gly His Trp Cys Ile Ile Pro Leu
        50                  55                  60

gca gct ggc caa gcg gtc tca gcc tac agt gag gag aga gac cgg cca      779
Ala Ala Gly Gln Ala Val Ser Ala Tyr Ser Glu Glu Arg Asp Arg Pro
    65                  70                  75

tat ggt ctg gtg tcc att gac aca gtg act gtg gga gat gca gag ggc      827
Tyr Gly Leu Val Ser Ile Asp Thr Val Thr Val Gly Asp Ala Glu Gly
 80                  85                  90                  95

ctg tgt gtc tgg ccc tgt agc tgt gag gat gat ggc tat cca gcc atg      875
Leu Cys Val Trp Pro Cys Ser Cys Glu Asp Asp Gly Tyr Pro Ala Met
                100                 105                 110

aac ctg gat gct ggc cga gag tct ggc cct aat tca gag gat ctg ctc      923
Asn Leu Asp Ala Gly Arg Glu Ser Gly Pro Asn Ser Glu Asp Leu Leu
            115                 120                 125

ttg gtc aca gac cct gct ttt ctg tct tgc ggc tgt gtc tca ggt agt      971
Leu Val Thr Asp Pro Ala Phe Leu Ser Cys Gly Cys Val Ser Gly Ser
        130                 135                 140

ggt ctc agg ctt gga ggc tcc cca ggc agc cta ctg gac agg ttg agg     1019
Gly Leu Arg Leu Gly Gly Ser Pro Gly Ser Leu Leu Asp Arg Leu Arg
    145                 150                 155

ctg tca ttt gca aag gaa ggg gac tgg aca gca gac cca acc tgg aga     1067
Leu Ser Phe Ala Lys Glu Gly Asp Trp Thr Ala Asp Pro Thr Trp Arg
160                 165                 170                 175

act ggg tcc cca gga ggg ggc tct gag agt gaa gca ggt tcc ccc cct     1115
Thr Gly Ser Pro Gly Gly Gly Ser Glu Ser Glu Ala Gly Ser Pro Pro
                180                 185                 190

ggt ctg gac atg gac aca ttt gac agt ggc ttt gca ggt tca gac tgt     1163
Gly Leu Asp Met Asp Thr Phe Asp Ser Gly Phe Ala Gly Ser Asp Cys
            195                 200                 205

ggc agc ccc gtg gag act gat gaa gga ccc cct cga agc tat ctc cgc     1211
Gly Ser Pro Val Glu Thr Asp Glu Gly Pro Pro Arg Ser Tyr Leu Arg
        210                 215                 220

cag tgg gtg gtc agg acc cct cca cct gtg gac agt gga gcc cag agc     1259
Gln Trp Val Val Arg Thr Pro Pro Pro Val Asp Ser Gly Ala Gln Ser
    225                 230                 235

agc tagcatataa taaccagcta tagtgagaag aggcct                         1298
Ser
240


<210> SEQ ID NO 70
<211> LENGTH: 240
<212> TYPE: PRT
<213> ORGANISM: Mus musculus

<400> SEQUENCE: 70

Lys Trp Val Asn Thr Pro Phe Thr Ala Ser Ser Ile Glu Leu Val Pro
 1               5                  10                  15

Gln Ser Ser Thr Thr Thr Ser Ala Leu His Leu Ser Leu Tyr Pro Ala
            20                  25                  30

Lys Glu Lys Lys Phe Pro Gly Leu Pro Gly Leu Glu Glu Gln Leu Glu
        35                  40                  45

Cys Asp Gly Met Ser Glu Pro Gly His Trp Cys Ile Ile Pro Leu Ala
```

```
    50                  55                  60

Ala Gly Gln Ala Val Ser Ala Tyr Ser Glu Glu Arg Asp Arg Pro Tyr
65                  70                  75                  80

Gly Leu Val Ser Ile Asp Thr Val Thr Val Gly Asp Ala Glu Gly Leu
                85                  90                  95

Cys Val Trp Pro Cys Ser Cys Glu Asp Asp Gly Tyr Pro Ala Met Asn
            100                 105                 110

Leu Asp Ala Gly Arg Glu Ser Gly Pro Asn Ser Glu Asp Leu Leu Leu
        115                 120                 125

Val Thr Asp Pro Ala Phe Leu Ser Cys Gly Cys Val Ser Gly Ser Gly
    130                 135                 140

Leu Arg Leu Gly Gly Ser Pro Gly Ser Leu Leu Asp Arg Leu Arg Leu
145                 150                 155                 160

Ser Phe Ala Lys Glu Gly Asp Trp Thr Ala Asp Pro Thr Trp Arg Thr
                165                 170                 175

Gly Ser Pro Gly Gly Gly Ser Glu Ser Glu Ala Gly Ser Pro Pro Gly
            180                 185                 190

Leu Asp Met Asp Thr Phe Asp Ser Gly Phe Ala Gly Ser Asp Cys Gly
        195                 200                 205

Ser Pro Val Glu Thr Asp Glu Gly Pro Pro Arg Ser Tyr Leu Arg Gln
    210                 215                 220

Trp Val Val Arg Thr Pro Pro Pro Val Asp Ser Gly Ala Gln Ser Ser
225                 230                 235                 240


<210> SEQ ID NO 71
<211> LENGTH: 23
<212> TYPE: DNA
<213> ORGANISM: Artificial Sequence
<220> FEATURE:
<223> OTHER INFORMATION: Oligonucleotide primer ZC24432

<400> SEQUENCE: 71

atgtctgagc ctggtcactg gtg                                              23


<210> SEQ ID NO 72
<211> LENGTH: 23
<212> TYPE: DNA
<213> ORGANISM: Artificial Sequence
<220> FEATURE:
<223> OTHER INFORMATION: Oligonucleotide primer ZC24433

<400> SEQUENCE: 72

tctgaacctg caaagccact gtc                                              23


<210> SEQ ID NO 73
<211> LENGTH: 27
<212> TYPE: DNA
<213> ORGANISM: Artificial Sequence
<220> FEATURE:
<223> OTHER INFORMATION: Oligonucleotide primer ZC9739

<400> SEQUENCE: 73

ccatcctaat acgactcact atagggc                                          27


<210> SEQ ID NO 74
<211> LENGTH: 22
<212> TYPE: DNA
<213> ORGANISM: Artificial Sequence
<220> FEATURE:
<223> OTHER INFORMATION: Oligonucleotide primer ZC24434

<400> SEQUENCE: 74
```

```
caccagtgac caggctcaga ca                                             22


<210> SEQ ID NO 75
<211> LENGTH: 23
<212> TYPE: DNA
<213> ORGANISM: Artificial Sequence
<220> FEATURE:
<223> OTHER INFORMATION: Oligonucleotide primer ZC24431

<400> SEQUENCE: 75

ccatcacact ccagttgctc ttc                                            23


<210> SEQ ID NO 76
<211> LENGTH: 23
<212> TYPE: DNA
<213> ORGANISM: Artificial Sequence
<220> FEATURE:
<223> OTHER INFORMATION: Oligonucleotide primer ZC9719

<400> SEQUENCE: 76

actcactata gggctcgagc ggc                                            23


<210> SEQ ID NO 77
<211> LENGTH: 23
<212> TYPE: DNA
<213> ORGANISM: Artificial Sequence
<220> FEATURE:
<223> OTHER INFORMATION: Oligonucleotide primer ZC24511

<400> SEQUENCE: 77

tccagcatag agttggtgcc aca                                            23


<210> SEQ ID NO 78
<211> LENGTH: 592
<212> TYPE: DNA
<213> ORGANISM: Mus musculus
<220> FEATURE:
<221> NAME/KEY: CDS
<222> LOCATION: (436)...(592)

<400> SEQUENCE: 78

cgcccgggca ggtctccgct ggtggccctg tgtttcagtc gcgcacagct gtctgcccac     60

ttctcctgtg gtgtgcctca cggtcacttg cttgtctgac cgcaagtctg cccatccctg    120

gggcagccaa ctggcctcag cccgtgcccc aggcgtgccc tgtctctgtc tggctgcccc    180

agccctactg tcttcctctg tgtaggctct gcccagatgc ccggctggtc ctcagcctca    240

ggactatctc agcagtgact cccctgattc tggacttgca cctgactgaa ctcctgccca    300

cctcaaacct tcacctccca ccaccaccac tccgagtccc gctgtgactc ccacgcccag    360

gagaccaccc aagtgcccca gcctaaagaa tggctttctg aggaagatcc tgaaggagta    420

ggtctgggac acagc atg ccc cgg ggc cca gtg gct gcc tta ctc ctg ctg     471
                 Met Pro Arg Gly Pro Val Ala Ala Leu Leu Leu Leu
                  1               5                  10

att ctc cat gga gct tgg agc tgc ctg grc ctc act tgc tac act gac      519
Ile Leu His Gly Ala Trp Ser Cys Leu Xaa Leu Thr Cys Tyr Thr Asp
         15                  20                  25

tac ctc tgg acc atc acc tgt gtc ctg gag aca cgg agc ccc aac ccc      567
Tyr Leu Trp Thr Ile Thr Cys Val Leu Glu Thr Arg Ser Pro Asn Pro
     30                  35                  40

agc ata ctc agt ctc acc tgg caa g                                    592
Ser Ile Leu Ser Leu Thr Trp Gln
 45                  50
```

```
<210> SEQ ID NO 79
<211> LENGTH: 52
<212> TYPE: PRT
<213> ORGANISM: Mus musculus
<220> FEATURE:
<221> NAME/KEY: VARIANT
<222> LOCATION: (1)...(51)
<223> OTHER INFORMATION: Xaa = Any Amino Acid

<400> SEQUENCE: 79

Met Pro Arg Gly Pro Val Ala Ala Leu Leu Leu Leu Ile Leu His Gly
 1               5                  10                  15

Ala Trp Ser Cys Leu Xaa Leu Thr Cys Tyr Thr Asp Tyr Leu Trp Thr
            20                  25                  30

Ile Thr Cys Val Leu Glu Thr Arg Ser Pro Asn Pro Ser Ile Leu Ser
        35                  40                  45

Leu Thr Trp Gln
    50


<210> SEQ ID NO 80
<211> LENGTH: 1229
<212> TYPE: DNA
<213> ORGANISM: Mus musculus
<220> FEATURE:
<221> NAME/KEY: CDS
<222> LOCATION: (3)...(1196)

<400> SEQUENCE: 80

ga cgc tat gat atc tcc tgg gac tca gct tat gac gaa ccc tcc aac        47
   Arg Tyr Asp Ile Ser Trp Asp Ser Ala Tyr Asp Glu Pro Ser Asn
    1               5                  10                  15

tac gtg ctg aga ggc aag cta caa tat gag ctg cag tat cgg aac ctc        95
Tyr Val Leu Arg Gly Lys Leu Gln Tyr Glu Leu Gln Tyr Arg Asn Leu
                20                  25                  30

aga gac ccc tat gct gtg agg ccg gtg acc aag ctg atc tca gtg gac       143
Arg Asp Pro Tyr Ala Val Arg Pro Val Thr Lys Leu Ile Ser Val Asp
            35                  40                  45

tca aga aac gtc tct ctt ctc cct gaa gag ttc cac aaa gat tct agc       191
Ser Arg Asn Val Ser Leu Leu Pro Glu Glu Phe His Lys Asp Ser Ser
        50                  55                  60

tac cag ctg cag atg cgg gca gcg cct cag cca ggc act tca ttc agg       239
Tyr Gln Leu Gln Met Arg Ala Ala Pro Gln Pro Gly Thr Ser Phe Arg
     65                  70                  75

ggg acc tgg agt gag tgg agt gac ccc gtc atc ttt cgg acc cag gct       287
Gly Thr Trp Ser Glu Trp Ser Asp Pro Val Ile Phe Arg Thr Gln Ala
 80                  85                  90                  95

ggg gag ccc gag gca ggc tgg gac cct cac atg ctg ctg ctc ctg gct       335
Gly Glu Pro Glu Ala Gly Trp Asp Pro His Met Leu Leu Leu Leu Ala
                100                 105                 110

gtc ttg atc att gtc ctg gtt ttc atg ggt ctg aag atc cac ctg cct       383
Val Leu Ile Ile Val Leu Val Phe Met Gly Leu Lys Ile His Leu Pro
            115                 120                 125

tgg agg cta tgg aaa aag ata tgg gca cca gtg ccc acc cct gag agt       431
Trp Arg Leu Trp Lys Lys Ile Trp Ala Pro Val Pro Thr Pro Glu Ser
        130                 135                 140

ttc ttc cag ccc ctg tgc agg gag cac agc ggg aac ttc aag aaa tgg       479
Phe Phe Gln Pro Leu Cys Arg Glu His Ser Gly Asn Phe Lys Lys Trp
    145                 150                 155

gtt aat acc cct ttc acg gcc tcc agc ata gag ttg gtg cca cag agt       527
Val Asn Thr Pro Phe Thr Ala Ser Ser Ile Glu Leu Val Pro Gln Ser
160                 165                 170                 175

tcc aca aca aca tca gcc tta cat ctg tca ttg tat cca gcc aag gag       575
```

```
Ser Thr Thr Thr Ser Ala Leu His Leu Ser Leu Tyr Pro Ala Lys Glu
                180                 185                 190

aag aag ttc ccg ggg ctg ccg ggt ctg gaa gag caa ctg gag tgt gat      623
Lys Lys Phe Pro Gly Leu Pro Gly Leu Glu Glu Gln Leu Glu Cys Asp
            195                 200                 205

gga atg tct gag cct ggt cac tgg tgc ata atc ccc ttg gca gct ggc      671
Gly Met Ser Glu Pro Gly His Trp Cys Ile Ile Pro Leu Ala Ala Gly
        210                 215                 220

caa gcg gtc tca gcc tac agt gag gag aga gac cgg cca tat ggt ctg      719
Gln Ala Val Ser Ala Tyr Ser Glu Glu Arg Asp Arg Pro Tyr Gly Leu
    225                 230                 235

gtg tcc att gac aca gtg act gtg gga gat gca gag ggc ctg tgt gtc      767
Val Ser Ile Asp Thr Val Thr Val Gly Asp Ala Glu Gly Leu Cys Val
240                 245                 250                 255

tgg ccc tgt agc tgt gag gat gat ggc tat cca gcc atg aac ctg gat      815
Trp Pro Cys Ser Cys Glu Asp Asp Gly Tyr Pro Ala Met Asn Leu Asp
                260                 265                 270

gct ggc cga gag tct ggc cct aat tca gag gat ctg ctc ttg gtc aca      863
Ala Gly Arg Glu Ser Gly Pro Asn Ser Glu Asp Leu Leu Leu Val Thr
            275                 280                 285

gac cct gct ttt ctg tct tgc ggc tgt gtc tca ggt agt ggt ctc agg      911
Asp Pro Ala Phe Leu Ser Cys Gly Cys Val Ser Gly Ser Gly Leu Arg
        290                 295                 300

ctt gga ggc tcc cca ggc agc cta ctg gac agg ttg agg ctg tca ttt      959
Leu Gly Gly Ser Pro Gly Ser Leu Leu Asp Arg Leu Arg Leu Ser Phe
    305                 310                 315

gca aag gaa ggg gac tgg aca gca gac cca acc tgg aga act ggg tcc     1007
Ala Lys Glu Gly Asp Trp Thr Ala Asp Pro Thr Trp Arg Thr Gly Ser
320                 325                 330                 335

cca gga ggg ggc tct gag agt gaa gca ggt tcc ccc cct ggt ctg gac     1055
Pro Gly Gly Gly Ser Glu Ser Glu Ala Gly Ser Pro Pro Gly Leu Asp
                340                 345                 350

atg gac aca ttt gac agt ggc ttt gca ggt tca gac tgt ggc agc ccc     1103
Met Asp Thr Phe Asp Ser Gly Phe Ala Gly Ser Asp Cys Gly Ser Pro
            355                 360                 365

gtg gag act gat gaa gga ccc cct cga agc tat ctc cgc cag tgg gtg     1151
Val Glu Thr Asp Glu Gly Pro Pro Arg Ser Tyr Leu Arg Gln Trp Val
        370                 375                 380

gtc agg acc cct cca cct gtg gac agt gga gcc cag agc agc tag         1196
Val Arg Thr Pro Pro Pro Val Asp Ser Gly Ala Gln Ser Ser  *
    385                 390                 395

catataataa ccagctatag tgagaagagg cct                                1229


<210> SEQ ID NO 81
<211> LENGTH: 397
<212> TYPE: PRT
<213> ORGANISM: Mus musculus

<400> SEQUENCE: 81

Arg Tyr Asp Ile Ser Trp Asp Ser Ala Tyr Asp Glu Pro Ser Asn Tyr
 1               5                  10                  15

Val Leu Arg Gly Lys Leu Gln Tyr Glu Leu Gln Tyr Arg Asn Leu Arg
            20                  25                  30

Asp Pro Tyr Ala Val Arg Pro Val Thr Lys Leu Ile Ser Val Asp Ser
        35                  40                  45

Arg Asn Val Ser Leu Leu Pro Glu Glu Phe His Lys Asp Ser Ser Tyr
    50                  55                  60

Gln Leu Gln Met Arg Ala Ala Pro Gln Pro Gly Thr Ser Phe Arg Gly
65                  70                  75                  80
```

```
Thr Trp Ser Glu Trp Ser Asp Pro Val Ile Phe Arg Thr Gln Ala Gly
                85                  90                  95

Glu Pro Glu Ala Gly Trp Asp Pro His Met Leu Leu Leu Leu Ala Val
            100                 105                 110

Leu Ile Ile Val Leu Val Phe Met Gly Leu Lys Ile His Leu Pro Trp
        115                 120                 125

Arg Leu Trp Lys Lys Ile Trp Ala Pro Val Pro Thr Pro Glu Ser Phe
    130                 135                 140

Phe Gln Pro Leu Cys Arg Glu His Ser Gly Asn Phe Lys Lys Trp Val
145                 150                 155                 160

Asn Thr Pro Phe Thr Ala Ser Ser Ile Glu Leu Val Pro Gln Ser Ser
                165                 170                 175

Thr Thr Thr Ser Ala Leu His Leu Ser Leu Tyr Pro Ala Lys Glu Lys
            180                 185                 190

Lys Phe Pro Gly Leu Pro Gly Leu Glu Glu Gln Leu Glu Cys Asp Gly
        195                 200                 205

Met Ser Glu Pro Gly His Trp Cys Ile Ile Pro Leu Ala Ala Gly Gln
    210                 215                 220

Ala Val Ser Ala Tyr Ser Glu Glu Arg Asp Arg Pro Tyr Gly Leu Val
225                 230                 235                 240

Ser Ile Asp Thr Val Thr Val Gly Asp Ala Glu Gly Leu Cys Val Trp
                245                 250                 255

Pro Cys Ser Cys Glu Asp Asp Gly Tyr Pro Ala Met Asn Leu Asp Ala
            260                 265                 270

Gly Arg Glu Ser Gly Pro Asn Ser Glu Asp Leu Leu Leu Val Thr Asp
        275                 280                 285

Pro Ala Phe Leu Ser Cys Gly Cys Val Ser Gly Ser Gly Leu Arg Leu
    290                 295                 300

Gly Gly Ser Pro Gly Ser Leu Leu Asp Arg Leu Arg Leu Ser Phe Ala
305                 310                 315                 320

Lys Glu Gly Asp Trp Thr Ala Asp Pro Thr Trp Arg Thr Gly Ser Pro
                325                 330                 335

Gly Gly Gly Ser Glu Ser Glu Ala Gly Ser Pro Pro Gly Leu Asp Met
            340                 345                 350

Asp Thr Phe Asp Ser Gly Phe Ala Gly Ser Asp Cys Gly Ser Pro Val
        355                 360                 365

Glu Thr Asp Glu Gly Pro Pro Arg Ser Tyr Leu Arg Gln Trp Val Val
    370                 375                 380

Arg Thr Pro Pro Pro Val Asp Ser Gly Ala Gln Ser Ser
385                 390                 395
```

<210> SEQ ID NO 82
<211> LENGTH: 23
<212> TYPE: DNA
<213> ORGANISM: Artificial Sequence
<220> FEATURE:
<223> OTHER INFORMATION: Oligonucleotide primer ZC24616

<400> SEQUENCE: 82
ctgcccacct caaaccttca cct 23

<210> SEQ ID NO 83
<211> LENGTH: 24
<212> TYPE: DNA
<213> ORGANISM: Artificial Sequence
<220> FEATURE:
<223> OTHER INFORMATION: Oligonucleotide primer ZC24615

<400> SEQUENCE: 83

```
atgctagctg ctctgggctc cact                                             24


<210> SEQ ID NO 84
<211> LENGTH: 1735
<212> TYPE: DNA
<213> ORGANISM: Mus musculus
<220> FEATURE:
<221> NAME/KEY: CDS
<222> LOCATION: (143)...(1729)

<400> SEQUENCE: 84

ctgcccacct caaaccttca cctcccacca ccaccactcc gagtcccgct gtgactccca     60

cgcccaggag accacccaag tgccccagcc taaagaatgg ctttctgaga aagaccctga    120

aggagtaggt ctgggacaca gc atg ccc cgg ggc cca gtg gct gcc tta ctc     172
                         Met Pro Arg Gly Pro Val Ala Ala Leu Leu
                          1               5                  10

ctg ctg att ctc cat gga gct tgg agc tgc ctg gac ctc act tgc tac      220
Leu Leu Ile Leu His Gly Ala Trp Ser Cys Leu Asp Leu Thr Cys Tyr
                15                  20                  25

act gac tac ctc tgg acc atc acc tgt gtc ctg gag aca cgg agc ccc      268
Thr Asp Tyr Leu Trp Thr Ile Thr Cys Val Leu Glu Thr Arg Ser Pro
            30                  35                  40

aac ccc agc ata ctc agt ctc acc tgg caa gat gaa tat gag gaa ctt      316
Asn Pro Ser Ile Leu Ser Leu Thr Trp Gln Asp Glu Tyr Glu Glu Leu
        45                  50                  55

cag gac caa gag acc ttc tgc agc cta cac agg tct ggc cac aac acc      364
Gln Asp Gln Glu Thr Phe Cys Ser Leu His Arg Ser Gly His Asn Thr
    60                  65                  70

aca cat ata tgg tac acg tgc cat atg cgc ttg tct caa ttc ctg tcc      412
Thr His Ile Trp Tyr Thr Cys His Met Arg Leu Ser Gln Phe Leu Ser
 75                  80                  85                  90

gat gaa gtt ttc att gtc aat gtg acg gac cag tct ggc aac aac tcc      460
Asp Glu Val Phe Ile Val Asn Val Thr Asp Gln Ser Gly Asn Asn Ser
                95                 100                 105

caa gag tgt ggc agc ttt gtc ctg gct gag agc atc aaa cca gct ccc      508
Gln Glu Cys Gly Ser Phe Val Leu Ala Glu Ser Ile Lys Pro Ala Pro
            110                 115                 120

ccc ttg aac gtg act gtg gcc ttc tca gga cgc tat gat atc tcc tgg      556
Pro Leu Asn Val Thr Val Ala Phe Ser Gly Arg Tyr Asp Ile Ser Trp
        125                 130                 135

gac tca gct tat gac gaa ccc tcc aac tac gtg ctg agg ggc aag cta      604
Asp Ser Ala Tyr Asp Glu Pro Ser Asn Tyr Val Leu Arg Gly Lys Leu
    140                 145                 150

caa tat gag ctg cag tat cgg aac ctc aga gac ccc tat gct gtg agg      652
Gln Tyr Glu Leu Gln Tyr Arg Asn Leu Arg Asp Pro Tyr Ala Val Arg
155                 160                 165                 170

ccg gtg acc aag ctg atc tca gtg gac tca aga aac gtc tct ctt ctc      700
Pro Val Thr Lys Leu Ile Ser Val Asp Ser Arg Asn Val Ser Leu Leu
                175                 180                 185

cct gaa gag ttc cac aaa gat tct agc tac cag ctg cag gtg cgg gca      748
Pro Glu Glu Phe His Lys Asp Ser Ser Tyr Gln Leu Gln Val Arg Ala
            190                 195                 200

gcg cct cag cca ggc act tca ttc agg ggg acc tgg agt gag tgg agt      796
Ala Pro Gln Pro Gly Thr Ser Phe Arg Gly Thr Trp Ser Glu Trp Ser
        205                 210                 215

gac ccc gtc atc ttt cag acc cag gct ggg gag ccc gag gca ggc tgg      844
Asp Pro Val Ile Phe Gln Thr Gln Ala Gly Glu Pro Glu Ala Gly Trp
    220                 225                 230

gac cct cac atg ctg ctg ctc ctg gct gtc ttg atc att gtc ctg gtt      892
```

```
Asp Pro His Met Leu Leu Leu Leu Ala Val Leu Ile Ile Val Leu Val
235                 240                 245                 250

ttc atg ggt ctg aag atc cac ctg cct tgg agg cta tgg aaa aag ata      940
Phe Met Gly Leu Lys Ile His Leu Pro Trp Arg Leu Trp Lys Lys Ile
                255                 260                 265

tgg gca cca gtg ccc acc cct gag agt ttc ttc cag ccc ctg tac agg      988
Trp Ala Pro Val Pro Thr Pro Glu Ser Phe Phe Gln Pro Leu Tyr Arg
            270                 275                 280

gag cac agc ggg aac ttc aag aaa tgg gtt aat acc cct ttc acg gcc     1036
Glu His Ser Gly Asn Phe Lys Lys Trp Val Asn Thr Pro Phe Thr Ala
        285                 290                 295

tcc agc ata gag ttg gtg cca cag agt tcc aca aca aca tca gcc tta     1084
Ser Ser Ile Glu Leu Val Pro Gln Ser Ser Thr Thr Thr Ser Ala Leu
    300                 305                 310

cat ctg tca ttg tat cca gcc aag gag aag aag ttc ccg ggg ctg ccg     1132
His Leu Ser Leu Tyr Pro Ala Lys Glu Lys Lys Phe Pro Gly Leu Pro
315                 320                 325                 330

ggt ctg gaa gag caa ctg gag tgt gat gga atg tct gag cct ggt cac     1180
Gly Leu Glu Glu Gln Leu Glu Cys Asp Gly Met Ser Glu Pro Gly His
                335                 340                 345

tgg tgc ata atc ccc ttg gca gct ggc caa gcg gtc tca gcc tac agt     1228
Trp Cys Ile Ile Pro Leu Ala Ala Gly Gln Ala Val Ser Ala Tyr Ser
            350                 355                 360

gag gag aga gac cgg cca tat ggt ctg gtg tcc att gac aca gtg act     1276
Glu Glu Arg Asp Arg Pro Tyr Gly Leu Val Ser Ile Asp Thr Val Thr
        365                 370                 375

gtg gga gat gca gag ggc ctg tgt gtc tgg ccc tgt agc tgt gag gat     1324
Val Gly Asp Ala Glu Gly Leu Cys Val Trp Pro Cys Ser Cys Glu Asp
    380                 385                 390

gat ggc tat cca gcc atg aac ctg gat gct ggc cga gag tct ggc cct     1372
Asp Gly Tyr Pro Ala Met Asn Leu Asp Ala Gly Arg Glu Ser Gly Pro
395                 400                 405                 410

aat tca gag gat ctg ctc ttg gtc aca gac cct gct ttt ctg tct tgc     1420
Asn Ser Glu Asp Leu Leu Leu Val Thr Asp Pro Ala Phe Leu Ser Cys
                415                 420                 425

ggc tgt gtc tca ggt agt ggt ctc agg ctt gga ggc tcc cca ggc agc     1468
Gly Cys Val Ser Gly Ser Gly Leu Arg Leu Gly Gly Ser Pro Gly Ser
            430                 435                 440

cta ctg gac agg ttg agg ctg tca ttt gca aag gaa ggg gac tgg aca     1516
Leu Leu Asp Arg Leu Arg Leu Ser Phe Ala Lys Glu Gly Asp Trp Thr
        445                 450                 455

gca gac cca acc tgg aga act ggg tcc cca gga ggg ggc tct gag agt     1564
Ala Asp Pro Thr Trp Arg Thr Gly Ser Pro Gly Gly Gly Ser Glu Ser
    460                 465                 470

gaa gca ggt tcc ccc cct ggt ctg gac atg gac aca ttt gac agt ggc     1612
Glu Ala Gly Ser Pro Pro Gly Leu Asp Met Asp Thr Phe Asp Ser Gly
475                 480                 485                 490

ttt gca ggt tca gac tgt ggc agc ccc gtg gag act gat gaa gga ccc     1660
Phe Ala Gly Ser Asp Cys Gly Ser Pro Val Glu Thr Asp Glu Gly Pro
                495                 500                 505

cct cga agc tat ctc cgc cag tgg gtg gtc agg acc cct cca cct gtg     1708
Pro Arg Ser Tyr Leu Arg Gln Trp Val Val Arg Thr Pro Pro Pro Val
            510                 515                 520

gac agt gga gcc cag agc agc tagcat                                  1735
Asp Ser Gly Ala Gln Ser Ser
        525


<210> SEQ ID NO 85
<211> LENGTH: 529
<212> TYPE: PRT
<213> ORGANISM: Mus musculus
```

<400> SEQUENCE: 85

```
Met Pro Arg Gly Pro Val Ala Ala Leu Leu Leu Leu Ile Leu His Gly
 1               5                  10                  15

Ala Trp Ser Cys Leu Asp Leu Thr Cys Tyr Thr Asp Tyr Leu Trp Thr
            20                  25                  30

Ile Thr Cys Val Leu Glu Thr Arg Ser Pro Asn Pro Ser Ile Leu Ser
        35                  40                  45

Leu Thr Trp Gln Asp Glu Tyr Glu Glu Leu Gln Asp Gln Glu Thr Phe
    50                  55                  60

Cys Ser Leu His Arg Ser Gly His Asn Thr Thr His Ile Trp Tyr Thr
65                  70                  75                  80

Cys His Met Arg Leu Ser Gln Phe Leu Ser Asp Glu Val Phe Ile Val
                85                  90                  95

Asn Val Thr Asp Gln Ser Gly Asn Asn Ser Gln Glu Cys Gly Ser Phe
            100                 105                 110

Val Leu Ala Glu Ser Ile Lys Pro Ala Pro Pro Leu Asn Val Thr Val
        115                 120                 125

Ala Phe Ser Gly Arg Tyr Asp Ile Ser Trp Asp Ser Ala Tyr Asp Glu
    130                 135                 140

Pro Ser Asn Tyr Val Leu Arg Gly Lys Leu Gln Tyr Glu Leu Gln Tyr
145                 150                 155                 160

Arg Asn Leu Arg Asp Pro Tyr Ala Val Arg Pro Val Thr Lys Leu Ile
                165                 170                 175

Ser Val Asp Ser Arg Asn Val Ser Leu Leu Pro Glu Glu Phe His Lys
            180                 185                 190

Asp Ser Ser Tyr Gln Leu Gln Val Arg Ala Ala Pro Gln Pro Gly Thr
        195                 200                 205

Ser Phe Arg Gly Thr Trp Ser Glu Trp Ser Asp Pro Val Ile Phe Gln
    210                 215                 220

Thr Gln Ala Gly Glu Pro Glu Ala Gly Trp Asp Pro His Met Leu Leu
225                 230                 235                 240

Leu Leu Ala Val Leu Ile Ile Val Leu Val Phe Met Gly Leu Lys Ile
                245                 250                 255

His Leu Pro Trp Arg Leu Trp Lys Lys Ile Trp Ala Pro Val Pro Thr
            260                 265                 270

Pro Glu Ser Phe Phe Gln Pro Leu Tyr Arg Glu His Ser Gly Asn Phe
        275                 280                 285

Lys Lys Trp Val Asn Thr Pro Phe Thr Ala Ser Ser Ile Glu Leu Val
    290                 295                 300

Pro Gln Ser Ser Thr Thr Thr Ser Ala Leu His Leu Ser Leu Tyr Pro
305                 310                 315                 320

Ala Lys Glu Lys Lys Phe Pro Gly Leu Pro Gly Leu Glu Glu Gln Leu
                325                 330                 335

Glu Cys Asp Gly Met Ser Glu Pro Gly His Trp Cys Ile Ile Pro Leu
            340                 345                 350

Ala Ala Gly Gln Ala Val Ser Ala Tyr Ser Glu Glu Arg Asp Arg Pro
        355                 360                 365

Tyr Gly Leu Val Ser Ile Asp Thr Val Thr Val Gly Asp Ala Glu Gly
    370                 375                 380

Leu Cys Val Trp Pro Cys Ser Cys Glu Asp Asp Gly Tyr Pro Ala Met
385                 390                 395                 400

Asn Leu Asp Ala Gly Arg Glu Ser Gly Pro Asn Ser Glu Asp Leu Leu
                405                 410                 415
```

```
Leu Val Thr Asp Pro Ala Phe Leu Ser Cys Gly Cys Val Ser Gly Ser
            420                 425                 430

Gly Leu Arg Leu Gly Gly Ser Pro Gly Ser Leu Leu Asp Arg Leu Arg
        435                 440                 445

Leu Ser Phe Ala Lys Glu Gly Asp Trp Thr Ala Asp Pro Thr Trp Arg
    450                 455                 460

Thr Gly Ser Pro Gly Gly Gly Ser Glu Ser Glu Ala Gly Ser Pro Pro
465                 470                 475                 480

Gly Leu Asp Met Asp Thr Phe Asp Ser Gly Phe Ala Gly Ser Asp Cys
                485                 490                 495

Gly Ser Pro Val Glu Thr Asp Glu Gly Pro Pro Arg Ser Tyr Leu Arg
            500                 505                 510

Gln Trp Val Val Arg Thr Pro Pro Pro Val Asp Ser Gly Ala Gln Ser
        515                 520                 525

Ser
```

<210> SEQ ID NO 86
<211> LENGTH: 16
<212> TYPE: DNA
<213> ORGANISM: Artificial Sequence
<220> FEATURE:
<223> OTHER INFORMATION: Oligonucleotide primer ZC3424

<400> SEQUENCE: 86
aacagctatg accatg 16

<210> SEQ ID NO 87
<211> LENGTH: 20
<212> TYPE: DNA
<213> ORGANISM: Artificial Sequence
<220> FEATURE:
<223> OTHER INFORMATION: Oligonucleotide primer ZC694

<400> SEQUENCE: 87
taatacgact cactataggg 20

<210> SEQ ID NO 88
<211> LENGTH: 20
<212> TYPE: DNA
<213> ORGANISM: Artificial Sequence
<220> FEATURE:
<223> OTHER INFORMATION: Oligonucleotide primer ZC24399

<400> SEQUENCE: 88
agcggtctca gcctacagtg 20

<210> SEQ ID NO 89
<211> LENGTH: 20
<212> TYPE: DNA
<213> ORGANISM: Artificial Sequence
<220> FEATURE:
<223> OTHER INFORMATION: Oligonucleotide primer ZC24400

<400> SEQUENCE: 89
tgagctgggg acaacaaggt 20

<210> SEQ ID NO 90
<211> LENGTH: 20
<212> TYPE: DNA
<213> ORGANISM: Artificial Sequence
<220> FEATURE:
<223> OTHER INFORMATION: Oligonucleotide primer ZC24806

```
<400> SEQUENCE: 90

tgacgaaccc tccaactacg                                              20


<210> SEQ ID NO 91
<211> LENGTH: 20
<212> TYPE: DNA
<213> ORGANISM: Artificial Sequence
<220> FEATURE:
<223> OTHER INFORMATION: Oligonucleotide primer ZC24807

<400> SEQUENCE: 91

tgctctcagc caggacaaag                                              20
```

METHODS FOR PRODUCING CYTOKINE RECEPTOR ZALPHA11

REFERENCE TO RELATED APPLICATIONS

This application is a continuation of U.S. patent application Ser. No. 13/039,459 filed Mar. 3, 2011 now U.S. Pat. No. 8,110,372, which is a divisional of U.S. patent application Ser. No. 12/623,651, filed Nov. 23, 2009, issued as U.S. Pat. No. 7,923,212, which is a continuation of U.S. patent application Ser. No. 11/537,835, filed Oct. 2, 2006, issued as U.S. Pat. No. 7,638,286, which is a divisional of U.S. patent application Ser. No. 10/715,998, filed Nov. 18, 2003, issued as U.S. Pat. No. 7,411,056, which is a divisional of U.S. patent application Ser. No. 09/404,641, filed Sep. 23, 1999, issued as U.S. Pat. No. 6,576,744, which claims the benefit of U.S. Provisional Patent Application No. 60/100,896, filed Sep. 23, 1998, U.S. Provisional Patent Application 60/123,546, filed Mar. 9, 1999, and U.S. Provisional Patent Application No. 60/142,574, filed Jul. 6, 1999, all of which are incorporated herein by reference.

BACKGROUND OF THE INVENTION

Proliferation and differentiation of cells of multicellular organisms are controlled by hormones and polypeptide growth factors. These diffusable molecules allow cells to communicate with each other and act in concert to form cells and organs, and to repair damaged tissue. Examples of hormones and growth factors include the steroid hormones (e.g. estrogen, testosterone), parathyroid hormone, follicle stimulating hormone, the interleukins, platelet derived growth factor (PDGF), epidermal growth factor (EGF), granulocyte-macrophage colony stimulating factor (GM-CSF), erythropoietin (EPO) and calcitonin.

Hormones and growth factors influence cellular metabolism by binding to receptors. Receptors may be integral membrane proteins that are linked to signaling pathways within the cell, such as second messenger systems. Other classes of receptors are soluble molecules, such as the transcription factors. Of particular interest are receptors for cytokines, molecules that promote the proliferation and/or differentiation of cells. Examples of cytokines include erythropoietin (EPO), which stimulates the development of red blood cells; thrombopoietin (TPO), which stimulates development of cells of the megakaryocyte lineage; and granulocyte-colony stimulating factor (G-CSF), which stimulates development of neutrophils. These cytokines are useful in restoring normal blood cell levels in patients suffering from anemia, thrombocytopenia, and neutropenia or receiving chemotherapy for cancer.

The demonstrated in vivo activities of these cytokines illustrate the enormous clinical potential of, and need for, other cytokines, cytokine agonists, and cytokine antagonists. The present invention addresses these needs by providing new a hematopoietic cytokine receptor, as well as related compositions and methods.

The present invention provides such polypeptides for these and other uses that should be apparent to those skilled in the art from the teachings herein.

SUMMARY OF THE INVENTION

Within one aspect, the present invention provides an isolated polynucleotide that encodes a zalpha11 polypeptide comprising a sequence of amino acid residues that is at least 90% identical to an amino acid sequence selected from the group consisting of: (a) the amino acid sequence as shown in SEQ ID NO:2 from amino acid number 20 (Cys), to amino acid number 237 (His); (b) the amino acid sequence as shown in SEQ ID NO:2 from amino acid number 20 (Cys), to amino acid number 255 (Leu); (c) the amino acid sequence as shown in SEQ ID NO:2 from amino acid number 256 (Lys), to amino acid number 538 (Ser); (d) the amino acid sequence as shown in SEQ ID NO:2 from amino acid number 20 (Cys), to amino acid number 538 (Ser); and (e) the amino acid sequence as shown in SEQ ID NO:2 from amino acid number 1 (Met) to amino acid number 538 (Ser), wherein the amino acid percent identity is determined using a FASTA program with ktup=1, gap opening penalty=10, gap extension penalty=1, and substitution matrix=BLOSUM62, with other parameters set as default. Within one embodiment, the isolated polynucleotide disclosed above comprises a sequence of polynucleotides that is selected from the group consisting of: (a) a polynucleotide sequence as shown in SEQ ID NO:4 from nucleotide 1 to nucleotide 1614; (b) a polynucleotide sequence as shown in SEQ ID NO:1 from nucleotide 126 to nucleotide 779; (c) a polynucleotide sequence as shown in SEQ ID NO:1 from nucleotide 126 to nucleotide 833; (d) a polynucleotide sequence as shown in SEQ ID NO:1 from nucleotide 834 to nucleotide 1682; (e) a polynucleotide sequence as shown in SEQ ID NO:1 from nucleotide 126 to nucleotide 1682; and (f) a polynucleotide sequence as shown in SEQ ID NO:1 from nucleotide 69 to nucleotide 1682. Within another embodiment, the isolated polynucleotide disclosed above comprises a sequence of amino acid residues selected from the group consisting of: (a) the amino acid sequence as shown in SEQ ID NO:2 from amino acid number 20 (Cys), to amino acid number 237 (His); (b) the amino acid sequence as shown in SEQ ID NO:2 from amino acid number 20 (Cys), to amino acid number 255 (Leu); (c) the amino acid sequence as shown in SEQ ID NO:2 from amino acid number 256 (Lys), to amino acid number 538 (Ser); (d) the amino acid sequence as shown in SEQ ID NO:2 from amino acid number 20 (Cys), to amino acid number 538 (Ser); and (e) the amino acid sequence as shown in SEQ ID NO:2 from amino acid number 1 (Met) to amino acid number 538 (Ser). Within another embodiment, the isolated polynucleotide disclosed above consists of a sequence of amino acid residues selected from the group consisting of: (a) the amino acid sequence as shown in SEQ ID NO:2 from amino acid number 20 (Cys), to amino acid number 237 (His); (b) the amino acid sequence as shown in SEQ ID NO:2 from amino acid number 20 (Cys), to amino acid number 255 (Leu); (c) the amino acid sequence as shown in SEQ ID NO:2 from amino acid number 256 (Lys), to amino acid number 538 (Ser); (d) the amino acid sequence as shown in SEQ ID NO:2 from amino acid number 20 (Cys), to amino acid number 538 (Ser); and (e) the amino acid sequence as shown in SEQ ID NO:2 from amino acid number 1 (Met) to amino acid number 538 (Ser). Within another embodiment, the isolated polynucleotide disclosed above further comprises a WSWSX domain. Within another embodiment, the isolated polynucleotide disclosed above further comprises a transmembrane domain. Within another embodiment, the isolated polynucleotide disclosed above comprises a transmembrane domain consisting of residues 238 (Leu) to 255 (Leu) of SEQ ID NO:2. Within another embodiment, the isolated polynucleotide disclosed above further comprises an intracellular domain. Within another embodiment, the isolated polynucleotide disclosed above comprises an intracellular domain consists of residues 256 (Lys) to 538 (Ser) of SEQ ID NO:2. Within another embodiment, the isolated polynucleotide disclosed above comprises an intracellular domain which domain further comprises Box I and Box II sites.

comprises an intracellular domain wherein the polypeptide further comprises an affinity tag.

Within a second aspect, the present invention provides an expression vector comprising the following operably linked elements: a transcription promoter; a DNA segment encoding a zalpha11 polypeptide having an amino acid sequence as shown in SEQ ID NO:2 from amino acid number 20 (Cys), to amino acid number 538 (Ser); and a transcription terminator, wherein the promoter is operably linked to the DNA segment, and the DNA segment is operably linked to the transcription terminator. Within one embodiment, the expression vector disclosed above further comprises a secretory signal sequence operably linked to the DNA segment.

Within a third aspect, the present invention provides a cultured cell comprising an expression vector as disclosed above, wherein the cell expresses a polypeptide encoded by the DNA segment.

Within a fourth aspect, the present invention provides an expression vector comprising: a transcription promoter; a DNA segment encoding a zalpha11 polypeptide having an amino acid sequence as shown in SEQ ID NO:2 from amino acid number 20 (Cys), to amino acid number 237 (His); and a transcription terminator, wherein the promoter, DNA segment, and terminator are operably linked. Within one embodiment, the expression vector disclosed above further comprises a secretory signal sequence operably linked to the DNA segment. Within another embodiment, the expression vector disclosed above further comprises a transmembrane domain operably linked to the DNA segment. Within another embodiment, the expression vector disclosed above further comprises a transmembrane domain consisting of residues 238 (Leu) to 255 (Leu) of SEQ ID NO:2. Within another embodiment, the expression vector disclosed above further comprises an intracellular domain operably linked to the DNA segment. Within another embodiment, the expression vector disclosed above further comprises an intracellular domain consisting of residues 256 (Lys) to 538 (Ser) of SEQ ID NO:2.

Within another aspect, the present invention provides a cultured cell into which has been introduced an expression vector according to claim 15, wherein the cell expresses a soluble receptor polypeptide encoded by the DNA segment. Within one embodiment, the cultured cell disclosed above is dependent upon an exogenously supplied hematopoietic growth factor for proliferation.

Within another aspect, the present invention provides a DNA construct encoding a fusion protein, the DNA construct comprising: a first DNA segment encoding a polypeptide having a sequence of amino acid residues selected from the group consisting of: (a) the amino acid sequence of SEQ ID NO:2 from amino acid number 1 (Met), to amino acid number 19 (Gly); (b) the amino acid sequence of SEQ ID NO:2 from amino acid number 20 (Cys) to amino acid number 237 (His); (c) the amino acid sequence of SEQ ID NO:2 from amino acid number 20 (Cys) to amino acid number 255 (Leu); (d) the amino acid sequence of SEQ ID NO:2 from amino acid number 238 (Leu) to amino acid number 255 (Leu); (e) the amino acid sequence of SEQ ID NO:2 from amino acid number 238 (Leu) to amino acid number 538 (Ser); (f) the amino acid sequence of SEQ ID NO:2 from amino acid number 256 (Lys) to amino acid number 538 (Ser); and (g) the amino acid sequence of SEQ ID NO:2 from amino acid number 20 (Cys), to amino acid number 538 (Ser); and at least one other DNA segment encoding an additional polypeptide, wherein the first and other DNA segments are connected in-frame; and wherein the first and other DNA segments encode the fusion protein.

Within another aspect, the present invention provides an expression vector comprising the following operably linked elements: a transcription promoter; a DNA construct encoding a fusion protein as disclosed above; and a transcription terminator, wherein the promoter is operably linked to the DNA construct, and the DNA construct is operably linked to the transcription terminator.

Within another aspect, the present invention provides a cultured cell comprising an expression vector as disclosed above, wherein the cell expresses a polypeptide encoded by the DNA construct.

Within another aspect, the present invention provides a method of producing a fusion protein comprising: culturing a cell as disclosed above; and isolating the polypeptide produced by the cell.

Within another aspect, the present invention provides an isolated polypeptide comprising a sequence of amino acid residues that is at least 90% identical to an amino acid sequence selected from the group consisting of: (a) the amino acid sequence as shown in SEQ ID NO:2 from amino acid number 20 (Cys), to amino acid number 237 (His); (b) the amino acid sequence as shown in SEQ ID NO:2 from amino acid number 20 (Cys), to amino acid number 255 (Leu); (c) the amino acid sequence as shown in SEQ ID NO:2 from amino acid number 256 (Lys), to amino acid number 538 (Ser); (d) the amino acid sequence as shown in SEQ ID NO:2 from amino acid number 20 (Cys), to amino acid number 538 (Ser); and (e) the amino acid sequence as shown in SEQ ID NO:2 from amino acid number 1 (Met) to amino acid number 538 (Ser), wherein the amino acid percent identity is determined using a FASTA program with ktup=1, gap opening penalty=10, gap extension penalty=1, and substitution matrix=BLOSUM62, with other parameters set as default. Within one embodiment, the isolated polypeptide disclosed above comprises a sequence of amino acid residues selected from the group consisting of: (a) the amino acid sequence as shown in SEQ ID NO:2 from amino acid number 20 (Cys), to amino acid number 237 (His); (b) the amino acid sequence as shown in SEQ ID NO:2 from amino acid number 20 (Cys), to amino acid number 255 (Leu); (c) the amino acid sequence as shown in SEQ ID NO:2 from amino acid number 256 (Lys), to amino acid number 538 (Ser); (d) the amino acid sequence as shown in SEQ ID NO:2 from amino acid number 20 (Cys), to amino acid number 538 (Ser); and (e) the amino acid sequence as shown in SEQ ID NO:2 from amino acid number 1 (Met) to amino acid number 538 (Ser). Within another embodiment, the isolated polypeptide disclosed above consists of a sequence of amino acid residues selected from the group consisting of: (a) the amino acid sequence as shown in SEQ ID NO:2 from amino acid number 20 (Cys), to amino acid number 237 (His); (b) the amino acid sequence as shown in SEQ ID NO:2 from amino acid number 20 (Cys), to amino acid number 255 (Leu); (c) the amino acid sequence as shown in SEQ ID NO:2 from amino acid number 256 (Lys), to amino acid number 538 (Ser); (d) the amino acid sequence as shown in SEQ ID NO:2 from amino acid number 20 (Cys), to amino acid number 538 (Ser); and (e) the amino acid sequence as shown in SEQ ID NO:2 from amino acid number 1 (Met) to amino acid number 538 (Ser). Within another embodiment, the isolated polypeptide disclosed above further contains a WSXWS motif. Within another embodiment, the isolated polypeptide disclosed above further comprises a transmembrane domain. Within another embodiment, the isolated polypeptide disclosed above further comprises a transmembrane domain, wherein the transmembrane domain consists of residues 238 (Leu) to 255 (Leu) of SEQ ID NO:2. Within another embodiment, the isolated polypeptide disclosed above further comprises an intracellular domain. Within another embodiment, the isolated polypeptide disclosed above further comprises an intracellular domain, wherein the intracellular domain consists of residues 256 (Lys) to 538 (Ser) of SEQ ID NO:2. Within another embodiment, the isolated polypeptide disclosed above further comprises an intracellular domain, wherein the intracellular domain further comprises Box I and Box II sites.

Within another aspect, the present invention provides a method of producing a zalpha11 polypeptide comprising: culturing a cell as disclosed above; and isolating the zalpha11 polypeptide produced by the cell.

Within another aspect, the present invention provides an isolated polypeptide comprising an amino acid sequence selected from the group consisting of: (a) the amino acid sequence as shown in SEQ ID NO:2 from amino acid number 20 (Cys), to amino acid number 237 (His); and wherein the polypeptide is substantially free of transmembrane and intracellular domains ordinarily associated with hematopoietic receptors. Within another embodiment, the isolated polypeptide disclosed above comprises an affinity tag.

Within another aspect, the present invention provides a method of producing a zalpha11 polypeptide comprising: culturing a cell as disclosed above; and isolating the zalpha11 polypeptide produced by the cell.

Within another aspect, the present invention provides a method of producing an antibody to zalpha11 polypeptide comprising: inoculating an animal with a polypeptide selected from the group consisting of: (a) a polypeptide consisting of 9 to 519 amino acids, wherein the polypeptide consists of a contiguous sequence of amino acids in SEQ ID NO:2 from amino acid number 20 (Cys), to amino acid number 538 (Ser); (b) a polypeptide consisting of the amino acid sequence of SEQ ID NO:2 from amino acid number 20 (Cys), to amino acid number 237 (His); (c) a polypeptide consisting of the amino acid sequence of SEQ ID NO:2 from amino acid number 101 (Leu) to amino acid number 122 (Gly); (d) a polypeptide consisting of the amino acid sequence of SEQ ID NO:2 from amino acid number 141 (Asn) to amino acid number 174 (Ala); (e) a polypeptide consisting of the amino acid sequence of SEQ ID NO:2 from amino acid number 193 (Cys) to amino acid number 261 (Val); (f) a polypeptide consisting of the amino acid sequence of SEQ ID NO:2 from amino acid number 51 (Trp) to amino acid number 61 (Glu); (g) a polypeptide consisting of the amino acid sequence of SEQ ID NO:2 from amino acid 136 (Ile) to amino acid number 143 (Glu); (h) a polypeptide consisting of the amino acid sequence of SEQ ID NO:2 from amino acid 187 (Pro) to amino acid number 195 (Ser); (i) a polypeptide consisting of the amino acid sequence of SEQ ID NO:2 from amino acid number 223 (Phe) to amino acid number 232 (Glu); and (j) a polypeptide consisting of the amino acid sequence of SEQ ID NO:2 from amino acid number 360 (Glu) to amino acid number 368 (Asp); and wherein the polypeptide elicits an immune response in the animal to produce the antibody; and isolating the antibody from the animal.

Within another aspect, the present invention provides an antibody produced by the method disclosed above, which specifically binds to a zalpha11 polypeptide. Within one embodiment, the antibody disclosed above is a monoclonal antibody.

Within another aspect, the present invention provides an antibody which specifically binds to a polypeptide as disclosed above.

Within another aspect, the present invention provides a method of detecting, in a test sample, the presence of a modulator of zalpha11 protein activity, comprising: culturing a cell into which has been introduced an expression vector as disclosed above, wherein the cell expresses the zalpha11 protein encoded by the DNA segment in the presence and absence of a test sample; and comparing levels of activity of zalpha11 in the presence and absence of a test sample, by a biological or biochemical assay; and determining from the comparison, the presence of modulator of zalpha11 activity in the test sample.

Within another aspect, the present invention provides a method for detecting a zalpha11 receptor ligand within a test sample, comprising: contacting a test sample with a polypeptide comprising an amino acid sequence as shown in SEQ ID NO:2 from amino acid number 20 (Cys), to amino acid number 237 (His); and detecting the binding of the polypeptide to a ligand in the sample. Within one embodiment, the method disclosed above further comprises a polypeptide comprising transmembrane and intracellular domains. Within another embodiment, the method disclosed above further comprises a polypeptide wherein the polypeptide is membrane bound within a cultured cell, and the detecting step comprises measuring a biological response in the cultured cell. Within another embodiment, the method disclosed above further comprises a polypeptide wherein the polypeptide is membrane bound within a cultured cell, and the detecting step comprises measuring a biological response in the cultured cell, wherein the biological response is cell proliferation or activation of transcription of a reporter gene. Within another embodiment, the method disclosed above further comprises a polypeptide wherein the polypeptide is immobilized on a solid support.

These and other aspects of the invention will become evident upon reference to the following detailed description of the invention.

BRIEF DESCRIPTION OF THE DRAWINGS

FIG. 2 is an alignment of human zalpha11 (zalpha) (SEQ ID NO: 2) and mouse zalpha11 (muza1p) (SEQ ID NO: 85).

DETAILED DESCRIPTION OF THE INVENTION

Figure 1A:
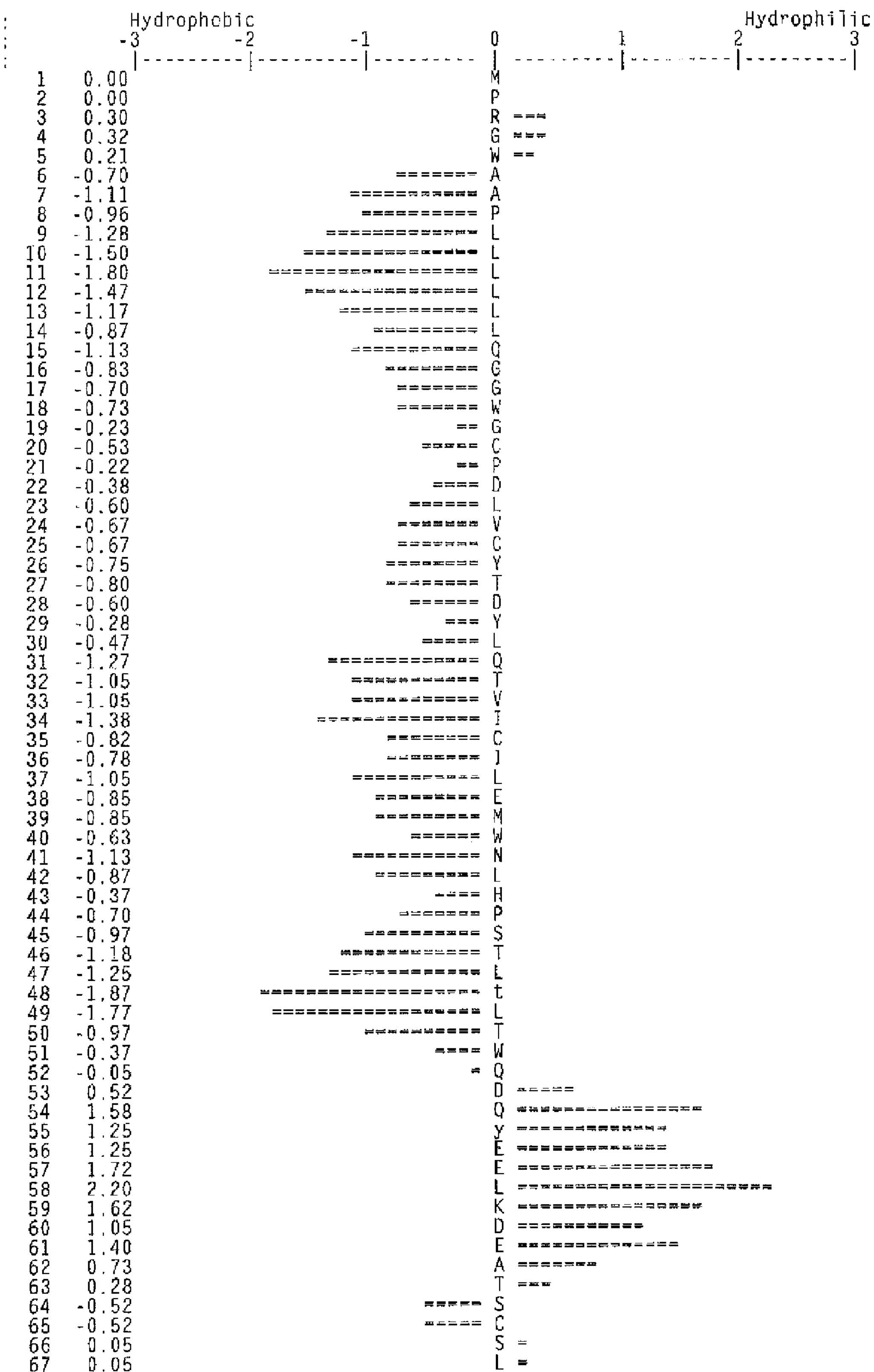
FIG. 1 is a Hopp/Woods hydrophilicity plot of human zalpha11.

Prior to setting forth the invention in detail, it may be helpful to the understanding thereof to define the following terms:

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952-4, 1985), substance P, Flag™ peptide (Hopp et al., *Biotechnology* 6:1204-10, 1988), streptavidin binding peptide, or other antigenic epitope or binding domain. See, in general, Ford et al., *Protein Expression and Purification* 2: 95-107, 1991. DNAs encoding affinity tags are available from commercial suppliers (e.g., Pharmacia Biotech, Piscataway, N.J.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like.

Where subsequent dissociation of the complement/anti-complement pair is desirable, the complement/anti-complement pair preferably has a binding affinity of $<10^9$ $M^{-1}$.

The term "complements of a polynucleotide molecule" is a polynucleotide molecule having a complementary base sequence and reverse orientation as compared to a reference sequence. For example, the sequence 5' ATGCACGGG 3' is complementary to 5' CCCGTGCAT 3'.

The term "contig" denotes a polynucleotide that has a contiguous stretch of identical or complementary sequence to another polynucleotide. Contiguous sequences are said to "overlap" a given stretch of polynucleotide sequence either in their entirety or along a partial stretch of the polynucleotide. For example, representative contigs to the polynucleotide sequence 5'-ATGGCTTAGCTT-3' are 5'-TAGCTTgagtct-3' and 3'-gtcgacTACCGA-5'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774-78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "operably linked", when referring to DNA segments, indicates that the segments are arranged so that they function in concert for their intended purposes, e.g., transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" is used herein to denote a cell-associated protein, or a polypeptide subunit of such a protein, that binds to a bioactive molecule (the "ligand") and mediates the effect of the ligand on the cell. Binding of ligand to receptor results in a conformational change in the receptor (and, in some cases, receptor multimerization, i.e., association of identical or different receptor subunits) that causes interactions between the effector domain(s) and other molecule(s) in the cell. These interactions in turn lead to alterations in the metabolism of the cell. Metabolic events that are linked to receptor-ligand interactions include gene transcription, phosphorylation, dephosphorylation, cell proliferation, increases in cyclic AMP production, mobilization of cellular calcium, mobilization of membrane lipids, cell adhesion, hydrolysis of inositol lipids and hydrolysis of phospholipids. Cell-surface cytokine receptors are characterized by a multi-domain structure as discussed in more detail below. These receptors are anchored in the cell membrane by a transmembrane domain characterized by a sequence of hydrophobic amino acid residues (typically about 21-25 residues), which is commonly flanked by positively charged residues (Lys or Arg). In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). The term “receptor polypeptide” is used to denote complete receptor polypeptide chains and portions thereof, including isolated functional domains (e.g., ligand-binding domains).

A “secretory signal sequence” is a DNA sequence that encodes a polypeptide (a “secretory peptide”) that, as a component of a larger polypeptide, directs the larger polypeptide through a secretory pathway of a cell in which it is synthesized. The larger peptide is commonly cleaved to remove the secretory peptide during transit through the secretory pathway.

A “soluble receptor” is a receptor polypeptide that is not bound to a cell membrane. Soluble receptors are most commonly ligand-binding receptor polypeptides that lack transmembrane and cytoplasmic domains. Soluble receptors can comprise additional amino acid residues, such as affinity tags that provide for purification of the polypeptide or provide sites for attachment of the polypeptide to a substrate, or immunoglobulin constant region sequences. Many cell-surface receptors have naturally occurring, soluble counterparts that are produced by proteolysis. Soluble receptor polypeptides are said to be substantially free of transmembrane and intracellular polypeptide segments when they lack sufficient portions of these segments to provide membrane anchoring or signal transduction, respectively.

The term “splice variant” is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as “about” X or “approximately” X, the stated value of X will be understood to be accurate to ±10%.

All references cited herein are incorporated by reference in their entirety.

The present invention is based in part upon the discovery of a novel DNA sequence that encodes a protein having the structure of a class I cytokine receptor. The deduced amino acid sequence indicated that the encoded receptor belongs to the receptor subfamily that includes the IL-2 receptor β-subunit and the β-common receptor (i.e., IL3, IL-5, and GM-CSF receptor β-subunits). Analysis of the tissue distribution of the mRNA corresponding to this novel DNA showed expression in lymph node, peripheral blood leukocytes (PBLs), spleen, and thymus. Moreover, the mRNA was abundant in the Raji cell line (ATCC No. CCL-86) derived from a Burkitt’s lymphoma. The polypeptide has been designated zalpha11.

The novel zalpha11 polypeptides of the present invention were initially identified by querying an EST database. An EST was found and its corresponding cDNA was sequenced. The novel polypeptide encoded by the cDNA showed homology with class I cytokine receptors. The zalpha11 polynucleotide sequence encodes the entire coding sequence of the predicted protein. Zalpha11 is a novel cytokine receptor that may be involved in an apoptotic cellular pathway, cell-cell signaling molecule, growth factor receptor, or extracellular matrix associated protein with growth factor hormone activity, or the like.

The sequence of the zalpha11 polypeptide was deduced from a single clone that contained its corresponding polynucleotide sequence. The clone was obtained from a spinal cord library. Other libraries that might also be searched for such sequences include PBL, thymus, spleen, lymph node, human erythroleukemia cell lines (e.g., TF-1), Raji cells, acute monocytic leukemia cell lines, other lymphoid and hematopoietic cell lines, and the like.

The nucleotide sequence of a representative zalpha11-encoding DNA is described in SEQ ID NO:1 (from nucleotide 69 to 1682), and its deduced 538 amino acid sequence is described in SEQ ID NO:2. In its entirety, the zalpha11 polypeptide (SEQ ID NO:2) represents a full-length polypeptide segment (residue 1 (Met) to residue 538 (Ser) of SEQ ID NO:2). The domains and structural features of the zalpha11 polypeptide are further described below. Analysis of the zalpha11 polypeptide encoded by the DNA sequence of SEQ ID NO:1 revealed an open reading frame encoding 538 amino acids (SEQ ID NO:2) comprising a predicted secretory signal peptide of 19 amino acid residues (residue 1 (Met) to residue 19 (Gly) of SEQ ID NO:2), and a mature polypeptide of 519 amino acids (residue 20 (Cys) to residue 538 (Ser) of SEQ ID NO:2). In addition to the WSXWS motif (SEQ ID NO:3) corresponding to residues 214 to 218 of SEQ ID NO:2, the receptor comprises a cytokine-binding domain of approximately 200 amino acid residues (residues 20 (Cys) to 237 (His) of SEQ ID NO:2); a domain linker (residues 120 (Pro) to 123 (Pro) of SEQ ID NO:2); a penultimate strand region (residues 192 (Lys) to 202 (Ala) of SEQ ID NO:2); a transmembrane domain (residues 238 (Leu) to 255 (Leu) of SEQ ID NO:2); complete intracellular signaling domain (residues 256 (Lys) to 538 (Ser) of SEQ ID NO:2) which contains a “Box I” signaling site (residues 267 (Ile) to 273 (Pro) of SEQ ID NO:2), and a “Box II” signaling site (residues 301 (Leu) to 304 (Gly) of SEQ ID NO:2). Those skilled in the art will recognize that these domain boundaries are approximate, and are based on alignments with known proteins and predictions of protein folding. In addition to these domains, conserved receptor features in the encoded receptor include (as shown in SEQ ID NO:2) a conserved Trp residue at position 138, and a conserved Arg residue at position 201. The corresponding polynucleotides encoding the zalpha11 polypeptide regions, domains, motifs, residues and sequences described above are as shown in SEQ ID NO:1.

The presence of transmembrane regions, and conserved and low variance motifs generally correlates with or defines important structural regions in proteins. Regions of low variance (e.g., hydrophobic clusters) are generally present in regions of structural importance (Sheppard, P. et al., supra.). Such regions of low variance often contain rare or infrequent amino acids, such as Tryptophan. The regions flanking and between such conserved and low variance motifs may be more variable, but are often functionally significant because they may relate to or define important structures and activities such as binding domains, biological and enzymatic activity, signal transduction, cell-cell interaction, tissue localization domains and the like.

The regions of conserved amino acid residues in zalpha11, described above, can be used as tools to identify new family members. For instance, reverse transcription-polymerase chain reaction (RT-PCR) can be used to amplify sequences encoding the conserved regions from RNA obtained from a variety of tissue sources or cell lines. In particular, highly degenerate primers designed from the zalpha11 sequences are useful for this purpose. Designing and using such degenerate primers may be readily performed by one of skill in the art.

The present invention provides polynucleotide molecules, including DNA and RNA molecules, that encode the zalpha11 polypeptides disclosed herein. Those skilled in the art will recognize that, in view of the degeneracy of the genetic code, considerable sequence variation is possible among these polynucleotide molecules. SEQ ID NO:4 is a degenerate DNA sequence that encompasses all DNAs that encode the zalpha11 polypeptide of SEQ ID NO:2. Those skilled in the art will recognize that the degenerate sequence of SEQ ID NO:4 also provides all RNA sequences encoding SEQ ID NO:2 by substituting U for T. Thus, zalpha11 polypeptide-encoding polynucleotides comprising nucleotide 1 to nucleotide 1614 of SEQ ID NO:4 and their RNA equivalents are contemplated by the present invention. Table 1 sets forth the one-letter codes used within SEQ ID NO:4 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 1

| Nucleotide | Resolution | Complement | Resolution |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:4, encompassing all possible codons for a given amino acid, are set forth in Table 2.

TABLE 2

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B | | RAY |
| Glu\|Gln | Z | | SAR |
| Any | X | | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NO:2. Variant sequences can be readily tested for functionality as described herein.

One of ordinary skill in the art will also appreciate that different species can exhibit "preferential codon usage." In general, see, Grantham, et al., *Nuc. Acids Res.* 8:1893-912, 1980; Haas, et al. *Curr. Biol.* 6:315-24, 1996; Wain-Hobson, et al., *Gene* 13:355-64, 1981; Grosjean and Fiers, *Gene*

18:199-209, 1982; Holm, *Nuc. Acids Res.* 14:3075-87, 1986; Ikemura, *J. Mol. Biol.* 158:573-97, 1982. As used herein, the term "preferential codon usage" or "preferential codons" is a term of art referring to protein translation codons that are most frequently used in cells of a certain species, thus favoring one or a few representatives of the possible codons encoding each amino acid (See Table 2). For example, the amino acid Threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequence disclosed in SEQ ID NO:4 serves as a template for optimizing expression of polynucleotides in various cell types and species commonly used in the art and disclosed herein. Sequences containing preferential codons can be tested and optimized for expression in various species, and tested for functionality as disclosed herein.

Within preferred embodiments of the invention the isolated polynucleotides will hybridize to similar sized regions of SEQ ID NO:1, or a sequence complementary thereto, under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Numerous equations for calculating $T_m$ are known in the art, and are specific for DNA, RNA and DNA-RNA hybrids and polynucleotide probe sequences of varying length (see, for example, Sambrook et al., *Molecular Cloning: A Laboratory Manual*, Second Edition (Cold Spring Harbor Press 1989); Ausubel et al., (eds.), *Current Protocols in Molecular Biology* (John Wiley and Sons, Inc. 1987); Berger and Kimmel (eds.), *Guide to Molecular Cloning Techniques*, (Academic Press, Inc. 1987); and Wetmur, *Crit. Rev. Biochem. Mol. Biol.* 26:227 (1990)). Sequence analysis software such as OLIGO 6.0 (LSR; Long Lake, Minn.) and *Primer Premier* 4.0 (Premier Biosoft International; Palo Alto, Calif.), as well as sites on the Internet, are available tools for analyzing a given sequence and calculating $T_m$ based on user defined criteria. Such programs can also analyze a given sequence under defined conditions and identify suitable probe sequences. Typically, hybridization of longer polynucleotide sequences (e.g., >50 base pairs) is performed at temperatures of about 20-25° C. below the calculated $T_m$. For smaller probes (e.g., <50 base pairs) hybridization is typically carried out at the $T_m$ or 5-10° C. below. This allows for the maximum rate of hybridization for DNA-DNA and DNA-RNA hybrids. Higher degrees of stringency at lower temperatures can be achieved with the addition of formamide which reduces the $T_m$ of the hybrid about 1° C. for each 1% formamide in the buffer solution. Suitable stringent hybridization conditions are equivalent to about a 5 h to overnight incubation at about 42° C. in a solution comprising: about 40-50% formamide, up to about 6×SSC, about 5×Denhardt's solution, zero up to about 10% dextran sulfate, and about 10-20 μg/ml denatured commercially-available carrier DNA. Generally, such stringent conditions include temperatures of 20-70° C. and a hybridization buffer containing up to 6×SSC and 0-50% formamide; hybridization is then followed by washing filters in up to about 2×SSC. For example, a suitable wash stringency is equivalent to 0.1×SSC to 2×SSC, 0.1% SDS, at 55° C. to 65° C. Different degrees of stringency can be used during hybridization and washing to achieve maximum specific binding to the target sequence. Typically, the washes following hybridization are performed at increasing degrees of stringency to remove non-hybridized polynucleotide probes from hybridized complexes. Stringent hybridization and wash conditions depend on the length of the probe, reflected in the Tm, hybridization and wash solutions used, and are routinely determined empirically by one of skill in the art.

As previously noted, the isolated polynucleotides of the present invention include DNA and RNA. Methods for preparing DNA and RNA are well known in the art. In general, RNA is isolated from a tissue or cell that produces large amounts of zalpha11 RNA. Such tissues and cells are identified by Northern blotting (Thomas, *Proc. Natl. Acad. Sci. USA* 77:5201, 1980), and include PBLs, spleen, thymus, and lymph tissues, Raji cells, human erythroleukemia cell lines (e.g., TF-1), acute monocytic leukemia cell lines, other lymphoid and hematopoietic cell lines, and the like. Total RNA can be prepared using guanidinium isothiocyanate extraction followed by isolation by centrifugation in a CsCl gradient (Chirgwin et al., *Biochemistry* 18:52-94, 1979). Poly $(A)^+$ RNA is prepared from total RNA using the method of Aviv and Leder (*Proc. Natl. Acad. Sci. USA* 69:1408-12, 1972). Complementary DNA (cDNA) is prepared from poly$(A)^+$ RNA using known methods. In the alternative, genomic DNA can be isolated. Polynucleotides encoding zalpha11 polypeptides are then identified and isolated by, for example, hybridization or polymerase chain reaction (PCR) (Mullis, U.S. Pat. No. 4,683,202).

A full-length clone encoding zalpha11 can be obtained by conventional cloning procedures. Complementary DNA (cDNA) clones are preferred, although for some applications (e.g., expression in transgenic animals) it may be preferable to use a genomic clone, or to modify a cDNA clone to include at least one genomic intron. Methods for preparing cDNA and genomic clones are well known and within the level of ordinary skill in the art, and include the use of the sequence disclosed herein, or parts thereof, for probing or priming a library. Expression libraries can be probed with antibodies to zalpha11, receptor fragments, or other specific binding partners.

The polynucleotides of the present invention can also be synthesized using DNA synthesis machines. Currently the method of choice is the phosphoramidite method. If chemically synthesized double stranded DNA is required for an application such as the synthesis of a gene or a gene fragment, then each complementary strand is made separately. The production of short polynucleotides (60 to 80 bp) is technically straightforward and can be accomplished by synthesizing the complementary strands and then annealing them. However, for producing longer polynucleotides (>300 bp), special strategies are usually employed, because the coupling efficiency of each cycle during chemical DNA synthesis is seldom 100%. To overcome this problem, synthetic genes (double-stranded) are assembled in modular form from single-stranded fragments that are from 20 to 100 nucleotides in length.

One method for building a synthetic gene requires the initial production of a set of overlapping, complementary oligonucleotides, each of which is between 20 to 60 nucleotides long. Each internal section of the gene has complementary 3' and 5' terminal extensions designed to base pair precisely with an adjacent section. Thus, after the gene is assembled, process is completed by sealing the nicks along the backbones of the two strands with T4 DNA ligase. In addition to the protein coding sequence, synthetic genes can be designed with terminal sequences that facilitate insertion into a restriction endonuclease site of a cloning vector. Moreover, other sequences should can be added that contain signals for proper initiation and termination of transcription and translation.

An alternative way to prepare a full-length gene is to synthesize a specified set of overlapping oligonucleotides (40 to 100 nucleotides). After the 3' and 5' short overlapping complementary regions (6 to 10 nucleotides) are annealed, large gaps still remain, but the short base-paired regions are both long enough and stable enough to hold the structure together. The gaps are filled and the DNA duplex is completed via enzymatic DNA synthesis by *E. coli* DNA polymerase I. After the enzymatic synthesis is completed, the nicks are sealed with T4 DNA ligase. Double-stranded constructs are sequentially linked to one another to form the entire gene sequence which is verified by DNA sequence analysis. See Glick and Pasternak, *Molecular Biotechnology, Principles & Applications of Recombinant DNA*, (ASM Press, Washington, D.C. 1994); Itakura et al., *Annu. Rev. Biochem.* 53: 323-56, 1984 and Climie et al., *Proc. Natl. Acad. Sci. USA* 87:633-7, 1990.

The present invention further provides counterpart polypeptides and polynucleotides from other species (orthologs). These species include, but are not limited to mammalian, avian, amphibian, reptile, fish, insect and other vertebrate and invertebrate species. Of particular interest are zalpha11 polypeptides from other mammalian species, including murine, porcine, ovine, bovine, canine, feline, equine, and other primate polypeptides. Orthologs of human zalpha11 can be cloned using information and compositions provided by the present invention in combination with conventional cloning techniques. For example, a cDNA can be cloned using mRNA obtained from a tissue or cell type that expresses zalpha11 as disclosed herein. Suitable sources of mRNA can be identified by probing Northern blots with probes designed from the sequences disclosed herein. A library is then prepared from mRNA of a positive tissue or cell line. A zalpha11-encoding cDNA can then be isolated by a variety of methods, such as by probing with a complete or partial human cDNA or with one or more sets of degenerate probes based on the disclosed sequences. A cDNA can also be cloned using PCR (Mullis, supra.), using primers designed from the representative human zalpha11 sequence disclosed herein. Within an additional method, the cDNA library can be used to transform or transfect host cells, and expression of the cDNA of interest can be detected with an antibody to zalpha11 polypeptide. Similar techniques can also be applied to the isolation of genomic clones.

Cytokine receptor subunits are characterized by a multi-domain structure comprising an extracellular domain, a transmembrane domain that anchors the polypeptide in the cell membrane, and an intracellular domain. The extracellular domain may be a ligand-binding domain, and the intracellular domain may be an effector domain involved in signal transduction, although ligand-binding and effector functions may reside on separate subunits of a multimeric receptor. The ligand-binding domain may itself be a multi-domain structure. Multimeric receptors include homodimers (e.g., PDGF receptor αα and ββ isoforms, erythropoietin receptor, MPL, and G-CSF receptor), heterodimers whose subunits each have ligand-binding and effector domains (e.g., PDGF receptor αβ isoform), and multimers having component subunits with disparate functions (e.g., IL-2, IL-3, IL-4, IL-5, IL-6, IL-7, and GM-CSF receptors). Some receptor subunits are common to a plurality of receptors. For example, the AIC2B subunit, which cannot bind ligand on its own but includes an intracellular signal transduction domain, is a component of IL-3 and GM-CSF receptors. Many cytokine receptors can be placed into one of four related families on the basis of the structure and function. Hematopoietic receptors, for example, are characterized by the presence of a domain containing conserved cysteine residues and the WSXWS motif (SEQ ID NO:3). Cytokine receptor structure has been reviewed by Urdal, *Ann. Reports Med. Chem.* 26:221-228, 1991 and Cosman, *Cytokine* 5:95-106, 1993. Under selective pressure for organisms to acquire new biological functions, new receptor family members likely arise from duplication of existing receptor genes leading to the existence of multi-gene families. Family members thus contain vestiges of the ancestral gene, and these characteristic features can be exploited in the isolation and identification of additional family members. Thus, the cytokine receptor superfamily is subdivided into several families, for example, the immunoglobulin family (including CSF-1, MGF, IL-1, and PDGF receptors); the hematopoietin family (including IL-2 receptor β-subunit, GM-CSF receptor α-subunit, GM-CSF receptor β-subunit; and G-CSF, EPO, IL-3, IL-4, IL-5, IL-6, IL-7, and IL-9 receptors); TNF receptor family (including TNF (p80) TNF (p60) receptors, CD27, CD30, CD40, Fas, and NGF receptor).

Analysis of the zalpha11 sequence suggests that it is a member of the same receptor subfamily as the IL-2 receptor β-subunit, IL-3, IL-4, and IL-6 receptors. Certain receptors in this subfamily (e.g., G-CSF) associate to form homodimers that transduce a signal. Other members of the subfamily (e.g., IL-6, IL-11, and LIF receptors) combine with a second subunit (termed a β-subunit) to bind ligand and transduce a signal. Specific β-subunits associate with a plurality of specific cytokine receptor subunits. For example, the β-subunit gp130 (Hibi et al., *Cell* 63:1149-1157, 1990) associates with receptor subunits specific for IL-6, IL-11, and LIF (Gearing et al., *EMBO J.* 10:2839-2848, 1991; Gearing et al., U.S. Pat. No. 5,284,755). Oncostatin M binds to a heterodimer of LIF receptor and gp130. CNTF binds to trimeric receptors comprising CNTF receptor, LIF receptor, and gp130 subunits.

A polynucleotide sequence for the mouse ortholog of human zalpha11 has been identified and is shown in SEQ ID NO:84 and the corresponding amino acid sequence shown in SEQ ID NO: 85. Analysis of the mouse zalpha11 polypeptide encoded by the DNA sequence of SEQ ID NO:84 revealed an open reading frame encoding 529 amino acids (SEQ ID NO:85) comprising a predicted secretory signal peptide of 19 amino acid residues (residue 1 (Met) to residue 19 (Ser) of SEQ ID NO:85), and a mature polypeptide of 510 amino acids (residue 20 (Cys) to residue 529 (Ser) of SEQ ID NO:2). In addition to the WSXWS motif (SEQ ID NO:3) corresponding to residues 214 to 218 of SEQ ID NO:85, the receptor comprises a cytokine-binding domain of approximately 200 amino acid residues (residues 20 (Cys) to 237 (His) of SEQ ID NO:85); a domain linker (residues 120 (Pro) to 123 (Pro) of SEQ ID NO:85); a penultimate strand region (residues 192 (Lys) to 202 (Ala) of SEQ ID NO:85); a transmembrane domain (residues 238 (Met) to 254 (Leu) of SEQ ID NO:85); complete intracellular signaling domain (residues 255 (Lys) to 529 (Ser) of SEQ ID NO:85) which contains a "Box I" signaling site (residues 266 (Ile) to 273 (Pro) of SEQ ID NO:85), and a "Box II" signaling site (residues 301 (Ile) to 304 (Val) of SEQ ID NO:2). A comparison of the human and mouse amino acid sequences reveals that both the human and orthologous polypeptides contain corresponding structural features described above (See, FIG. 2). The mature sequence for the mouse zalpha11 begins at $Cys_{20}$ (as shown in SEQ ID NO:85), which corresponds to $Cys_{20}$ (as shown in SEQ ID NO:2) in the human sequence. There is about 63% identity between the mouse and human sequences over the entire amino acid sequence corresponding to SEQ ID NO:2 and SEQ ID NO:85. There is about 69% identity a between the mouse and human zalpha11 sequences over the extracellular cytokine binding domain corresponding to residues 20 (Cys) to 237 (His) of SEQ ID NO:2 and residues 20 (Cys) to 237 (His) of SEQ ID NO:85. There is about 60% identity a between the mouse and human zalpha11 sequences over the intracellular signalling domain corresponding to residues 256 (Lys) to 538 (Ser) of SEQ ID NO:2, and residues 255 (Lys) to 529 (Ser) of SEQ ID NO:85. The above percent identities were determined using a FASTA program with ktup=1, gap opening penalty=12, gap extension penalty=2, and substitution matrix=BLOSUM62, with other parameters set as default. The corresponding polynucleotides encoding the mouse zalpha11 polypeptide regions, domains, motifs, residues and sequences described above are as shown in SEQ ID NO:84.

Those skilled in the art will recognize that the sequence disclosed in SEQ ID NO:1 represents a single allele of human zalpha11 and that allelic variation and alternative splicing are expected to occur. Allelic variants of this sequence can be cloned by probing cDNA or genomic libraries from different individuals according to standard procedures. Allelic variants of the DNA sequence shown in SEQ ID NO:1, including those containing silent mutations and those in which mutations result in amino acid sequence changes, are within the scope of the present invention, as are proteins which are allelic variants of SEQ ID NO:2. cDNAs generated from alternatively spliced mRNAs, which retain the properties of the zalpha11 polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

The present invention also provides isolated zalpha11 polypeptides that are substantially similar to the polypeptides of SEQ ID NO:2 and their orthologs. The term "substantially similar" is used herein to denote polypeptides having at least 70%, more preferably at least 80%, sequence identity to the sequences shown in SEQ ID NO:2 or their orthologs. Such polypeptides will more preferably be at least 90% identical, and most preferably 95% or more identical to SEQ ID NO:2 or its orthologs.) Percent sequence identity is determined by conventional methods. See, for example, Altschul et al., *Bull. Math. Bio.* 48: 603-616, 1986 and Henikoff and Henikoff, *Proc. Natl. Acad. Sci. USA* 89:10915-10919, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 3 (amino acids are indicated by the standard one-letter codes). The percent identity is then calculated as:

$$\frac{\text{Total number of identical matches}}{\left[\begin{array}{c}\text{length of the longer sequence plus}\\ \text{the number of gaps introduced into}\\ \text{the longer sequence in order to align}\\ \text{the two sequences}\end{array}\right]}\times 100$$

TABLE 3

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | −1 | 5 | | | | | | | | | | | | | | | | | | |
| N | −2 | 0 | 6 | | | | | | | | | | | | | | | | | |
| D | −2 | −2 | 1 | 6 | | | | | | | | | | | | | | | | |
| C | 0 | −3 | −3 | −3 | 9 | | | | | | | | | | | | | | | |
| Q | −1 | 1 | 0 | 0 | −3 | 5 | | | | | | | | | | | | | | |
| E | −1 | 0 | 0 | 2 | −4 | 2 | 5 | | | | | | | | | | | | | |
| G | 0 | −2 | 0 | −1 | −3 | −2 | −2 | 6 | | | | | | | | | | | | |
| H | −2 | 0 | 1 | −1 | −3 | 0 | 0 | −2 | 8 | | | | | | | | | | | |
| I | −1 | −3 | −3 | −3 | −1 | −3 | −3 | −4 | −3 | 4 | | | | | | | | | | |
| L | −1 | −2 | −3 | −4 | −1 | −2 | −3 | −4 | −3 | 2 | 4 | | | | | | | | | |
| K | −1 | 2 | 0 | −1 | −3 | 1 | 1 | −2 | −1 | −3 | −2 | 5 | | | | | | | | |
| M | −1 | −1 | −2 | −3 | −1 | 0 | −2 | −3 | −2 | 1 | 2 | −1 | 5 | | | | | | | |
| F | −2 | −3 | −3 | −3 | −2 | −3 | −3 | −3 | −1 | 0 | 0 | −3 | 0 | 6 | | | | | | |
| P | −1 | −2 | −2 | −1 | −3 | −1 | −1 | −2 | −2 | −3 | −3 | −1 | −2 | −4 | 7 | | | | | |
| S | 1 | −1 | 1 | 0 | −1 | 0 | 0 | 0 | −1 | −2 | −2 | 0 | −1 | −2 | −1 | 4 | | | | |
| T | 0 | −1 | 0 | −1 | −1 | −1 | −1 | −2 | −2 | −1 | −1 | −1 | −1 | −2 | −1 | 1 | 5 | | | |
| W | −3 | −3 | −4 | −4 | −2 | −2 | −3 | −2 | −2 | −3 | −2 | −3 | −1 | 1 | −4 | −3 | −2 | 11 | | |
| Y | −2 | −2 | −2 | −3 | −2 | −1 | −2 | −3 | 2 | −1 | −1 | −2 | −1 | 3 | −3 | −2 | −2 | 2 | 7 | |
| V | 0 | −3 | −3 | −3 | −1 | −2 | −2 | −3 | −3 | 3 | 1 | −2 | 1 | −1 | −2 | −2 | 0 | −3 | −1 | 4 |

Sequence identity of polynucleotide molecules is determined by similar methods using a ratio as disclosed above.

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative variant zsig57. The FASTA algorithm is described by Pearson and Lipman, *Proc. Nat'l Acad. Sci. USA* 85:2444 (1988), and by Pearson, *Meth. Enzymol.* 183:63 (1990).

Briefly, FASTA first characterizes sequence similarity by identifying regions shared by the query sequence (e.g., SEQ ID NO:2) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444 (1970); Sellers, *SIAM J. Appl. Math.* 26:787 (1974)), which allows for amino acid insertions and deletions. Preferred parameters for FASTA analysis are: ktup=1, gap opening penalty=10, gap extension penalty=1, and substitution matrix=BLOSUM62, with other parameters set as default. These parameters can be introduced into a FASTA program by modifying the scoring matrix file ("SMATRIX"), as explained in Appendix 2 of Pearson, *Meth. Enzymol.* 183:63 (1990).

FASTA can also be used to determine the sequence identity of nucleic acid molecules using a ratio as disclosed above. For nucleotide sequence comparisons, the ktup value can range between one to six, preferably from three to six, most preferably three, with other parameters set as default.

The BLOSUM62 table (Table 3) is an amino acid substitution matrix derived from about 2,000 local multiple alignments of protein sequence segments, representing highly conserved regions of more than 500 groups of related proteins (Henikoff and Henikoff, *Proc. Nat'l Acad. Sci. USA* 89:10915 (1992)). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed below), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Variant zalpha11 polypeptides or substantially homologous zalpha11 polypeptides are characterized as having one or more amino acid substitutions, deletions or additions. These changes are preferably of a minor nature, that is conservative amino acid substitutions (see Table 4) and other substitutions that do not significantly affect the folding or activity of the polypeptide; small deletions, typically of one to about 30 amino acids; and small amino- or carboxyl-terminal extensions, such as an amino-terminal methionine residue, a small linker peptide of up to about 20-25 residues, or an affinity tag. The present invention thus includes polypeptides of from about 489 to about 568 amino acid residues that comprise a sequence that is at least 80%, preferably at least 90%, and more preferably 95% or more identical to the corresponding region of SEQ ID NO:2. Polypeptides comprising affinity tags can further comprise a proteolytic cleavage site between the zalpha11 polypeptide and the affinity tag. Suitable sites include thrombin cleavage sites and factor Xa cleavage sites.

TABLE 4

| Conservative amino acid substitutions | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

The present invention further provides a variety of other polypeptide fusions and related multimeric proteins comprising one or more polypeptide fusions. For example, a zalpha11 polypeptide can be prepared as a fusion to a dimerizing protein as disclosed in U.S. Pat. Nos. 5,155,027 and 5,567,584. Preferred dimerizing proteins in this regard include immunoglobulin constant region domains. Immunoglobulin-zalpha11 polypeptide fusions can be expressed in genetically engineered cells to produce a variety of multimeric zalpha11 analogs. Auxiliary domains can be fused to zalpha11 polypeptides to target them to specific cells, tissues, or macromolecules (e.g., collagen). A zalpha11 polypeptide can be fused to two or more moieties, such as an affinity tag for purification and a targeting domain. Polypeptide fusions can also comprise one or more cleavage sites, particularly between domains. See, Tuan et al., *Connective Tissue Research* 34:1-9, 1996.

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tent-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806-9, 1993; and Chung et al., *Proc. Natl. Acad. Sci. USA* 90:10145-9, 1993). In a second method, translation is carried out in *Xenopus* oocytes by microinjection of mutated mRNA and chemically aminoacylated suppressor tRNAs (Turcatti et al., *J. Biol. Chem.* 271:19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470-7476, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395-403, 1993).

A limited number of non-conservative amino acids, amino acids that are not encoded by the genetic code, non-naturally occurring amino acids, and unnatural amino acids may be substituted for zalpha11 amino acid residues.

Essential amino acids in the polypeptides of the present invention can be identified according to procedures known in the art, such as site-directed mutagenesis or alanine-scanning mutagenesis (Cunningham and Wells, *Science* 244: 1081-5, 1989; Bass et al., *Proc. Natl. Acad. Sci. USA* 88:4498-502, 1991). In the latter technique, single alanine mutations are introduced at every residue in the molecule, and the resultant mutant molecules are tested for biological activity (e.g. ligand binding and signal transduction) as disclosed below to identify amino acid residues that are critical to the activity of the molecule. See also, Hilton et al., *J. Biol. Chem.* 271:4699-4708, 1996. Sites of ligand-receptor, protein-protein or other biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306-312, 1992; Smith et al., *J. Mol. Biol.* 224:899-904, 1992; Wlodaver et al., *FEBS Lett.* 309:59-64, 1992. The identities of essential amino acids can also be inferred from analysis of homologies with related receptors.

Determination of amino acid residues that are within regions or domains that are critical to maintaining structural integrity can be determined. Within these regions one can determine specific residues that will be more or less tolerant of change and maintain the overall tertiary structure of the molecule. Methods for analyzing sequence structure include, but are not limited to, alignment of multiple sequences with high amino acid or nucleotide identity and computer analysis using available software (e.g., the INSIGHT II® viewer and homology modeling tools; MSI, San Diego, Calif.), secondary structure propensities, binary patterns, complementary packing and buried polar interactions (Barton, *Current Opin. Struct. Biol.* 5:372-376, 1995 and Cordes et al., *Current Opin. Struct. Biol.* 6:3-10, 1996). In general, when designing modifications to molecules or identifying specific fragments determination of structure will be accompanied by evaluating activity of modified molecules.

Amino acid sequence changes are made in zalpha11 polypeptides so as to minimize disruption of higher order structure essential to biological activity. For example, when the zalpha11 polypeptide comprises one or more helices, changes in amino acid residues will be made so as not to disrupt the helix geometry and other components of the molecule where changes in conformation abate some critical function, for example, binding of the molecule to its binding partners. The effects of amino acid sequence changes can be predicted by, for example, computer modeling as disclosed above or determined by analysis of crystal structure (see, e.g., Lapthorn et al., *Nat. Struct. Biol.* 2:266-268, 1995). Other techniques that are well known in the art compare folding of a variant protein to a standard molecule (e.g., the native protein). For example, comparison of the cysteine pattern in a variant and standard molecules can be made. Mass spectrometry and chemical modification using reduction and alkylation provide methods for determining cysteine residues which are associated with disulfide bonds or are free of such associations (Bean et al., *Anal. Biochem.* 201:216-226, 1992; Gray, *Protein Sci.* 2:1732-1748, 1993; and Patterson et al., *Anal. Chem.* 66:3727-3732, 1994). It is generally believed that if a modified molecule does not have the same disulfide bonding pattern as the standard molecule folding would be affected. Another well known and accepted method for measuring folding is circular dichrosism (CD). Measuring and comparing the CD spectra generated by a modified molecule and standard molecule is routine (Johnson, *Proteins* 7:205-214, 1990). Crystallography is another well known method for analyzing folding and structure. Nuclear magnetic resonance (NMR), digestive peptide mapping and epitope mapping are also known methods for analyzing folding and structural similarities between proteins and polypeptides (Schaanan et al., *Science* 257:961-964, 1992).

Figure 1H:
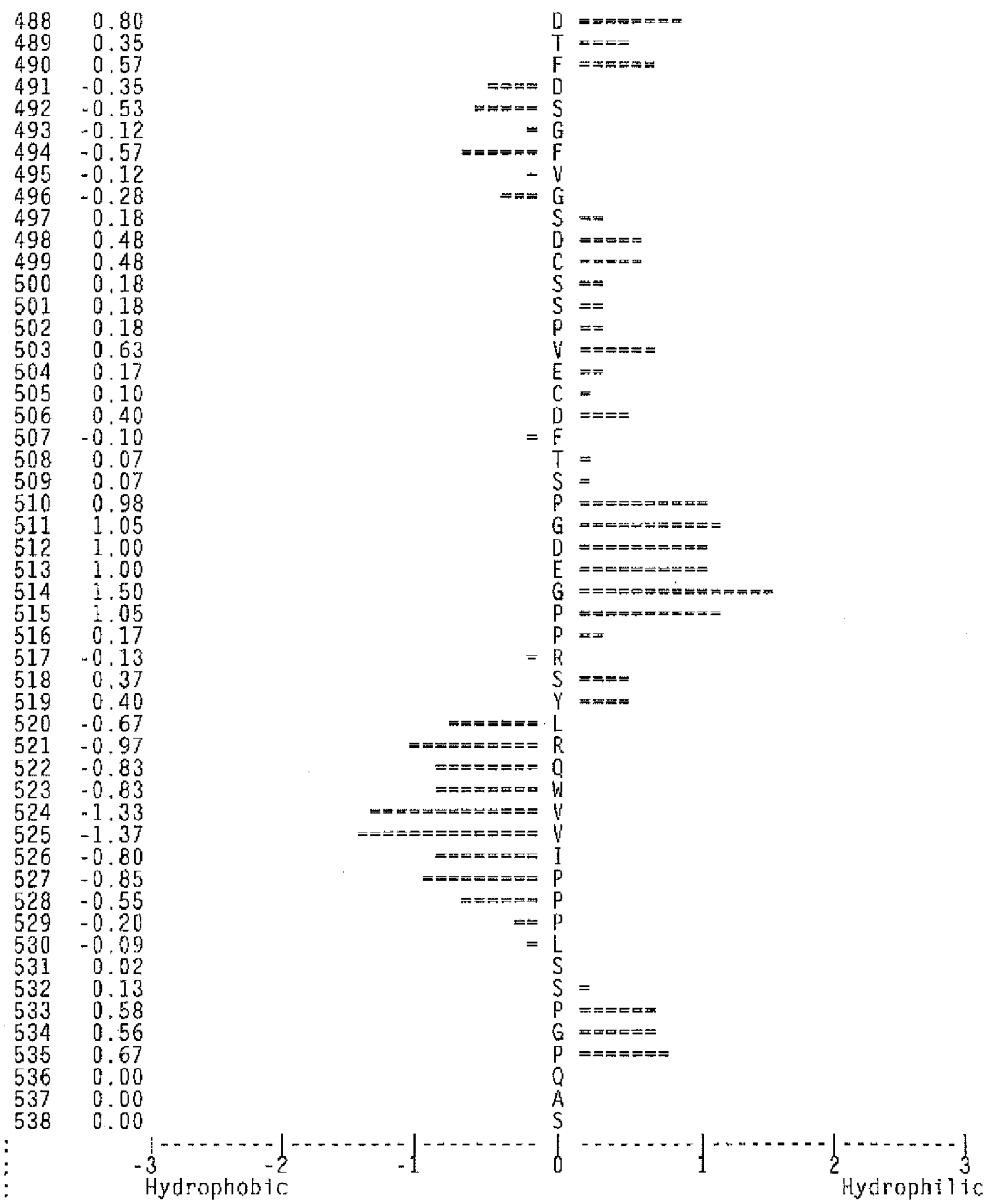

A Hopp/Woods hydrophilicity profile of the zalpha11 protein sequence as shown in SEQ ID NO:2 can be generated (Hopp et al., *Proc. Natl. Acad. Sci.* 78:3824-3828, 1981; Hopp, *J. Immun Meth.* 88:1-18, 1986 and Triquier et al., *Protein Engineering* 11:153-169, 1998). See, FIG. 1. The profile is based on a sliding six-residue window. Buried G, S, and T residues and exposed H, Y, and W residues were ignored. For example, in zalpha11, hydrophilic regions include amino acid residues 55 through 60 of SEQ ID NO: 2, amino acid residues 56 through 61 of SEQ ID NO: 2, amino acid residues 139 through 144 of SEQ ID NO: 2, amino acid residues 227 through 232 of SEQ ID NO: 2, and amino acid residues 364 through 369 of SEQ ID NO: 2.

Those skilled in the art will recognize that hydrophilicity or hydrophobicity will be taken into account when designing modifications in the amino acid sequence of a zalpha11 polypeptide, so as not to disrupt the overall structural and biological profile. Of particular interest for replacement are hydrophobic residues selected from the group consisting of Val, Leu and Ile or the group consisting of Met, Gly, Ser, Ala, Tyr and Trp. For example, residues tolerant of substitution could include such residues as shown in SEQ ID NO: 2. However, Cysteine residues could be relatively intolerant of substitution.

The identities of essential amino acids can also be inferred from analysis of sequence similarity between class I cytokine receptor family members with zalpha11. Using methods such as "FASTA" analysis described previously, regions of high similarity are identified within a family of proteins and used to analyze amino acid sequence for conserved regions. An alternative approach to identifying a variant zalpha11 polynucleotide on the basis of structure is to determine whether a nucleic acid molecule encoding a potential variant zalpha11 polynucleotide can hybridize to a nucleic acid molecule having the nucleotide sequence of SEQ ID NO:1, as discussed above.

Other methods of identifying essential amino acids in the polypeptides of the present invention are procedures known in the art, such as site-directed mutagenesis or alanine-scanning mutagenesis (Cunningham and Wells, *Science* 244:1081 (1989), Bass et al., *Proc. Natl. Acad. Sci. USA* 88:4498 (1991), Coombs and Corey, "Site-Directed Mutagenesis and Protein Engineering," in *Proteins: Analysis and Design*, Angeletti (ed.), pages 259-311 (Academic Press, Inc. 1998)). In the latter technique, single alanine mutations are introduced at every residue in the molecule, and the resultant mutant molecules are tested for biological activity as disclosed below to identify amino acid residues that are critical to the activity of the molecule. See also, Hilton et al., *J. Biol. Chem.* 271:4699 (1996).

The present invention also includes functional fragments of zalpha11 polypeptides and nucleic acid molecules encoding such functional fragments. A "functional" zalpha11 or fragment thereof defined herein is characterized by its proliferative or differentiating activity, by its ability to induce or inhibit specialized cell functions, or by its ability to bind specifically to an anti-zalpha11 antibody or zalpha11 ligand (either soluble or immobilized). As previously described herein, zalpha11 is characterized by a class I cytokine receptor structure. Thus, the present invention further provides fusion proteins encompassing: (a) polypeptide molecules comprising an extracellular or intracellular domain described herein; and (b) functional fragments comprising one or more of these domains. The other polypeptide portion of the fusion protein may be contributed by another class I cytokine receptor, for exapmple, IL-2 receptor β-subunit and the β-common receptor (i.e., IL3, IL-5, and GM-CSF receptor β-subunits), or by a non-native and/or an unrelated secretory signal peptide that facilitates secretion of the fusion protein.

Routine deletion analyses of nucleic acid molecules can be performed to obtain functional fragments of a nucleic acid molecule that encodes a zalpha11 polypeptide. As an illustration, DNA molecules having the nucleotide sequence of SEQ ID NO:1 or fragments thereof, can be digested with Bal31 nuclease to obtain a series of nested deletions. These DNA fragments are then inserted into expression vectors in proper reading frame, and the expressed polypeptides are isolated and tested for zalpha11 activity, or for the ability to bind anti-zalpha11 antibodies or zalpha11 ligand. One alternative to exonuclease digestion is to use oligonucleotide-directed mutagenesis to introduce deletions or stop codons to specify production of a desired zalpha11 fragment. Alternatively, particular fragments of a zalpha11 polynucleotide can be synthesized using the polymerase chain reaction.

Standard methods for identifying functional domains are well-known to those of skill in the art. For example, studies on the truncation at either or both termini of interferons have been summarized by Horisberger and Di Marco, *Pharmac. Ther.* 66:507 (1995). Moreover, standard techniques for functional analysis of proteins are described by, for example, Treuter et al., *Molec. Gen. Genet.* 240:113 (1993); Content et al., "Expression and preliminary deletion analysis of the 42 kDa 2-5A synthetase induced by human interferon," in *Biological Interferon Systems, Proceedings of ISIR-TNO Meeting on Interferon Systems*, Cantell (ed.), pages 65-72 (Nijhoff 1987); Herschman, "The EGF Receptor," in *Control of Animal Cell Proliferation* 1 Boynton et al., (eds.) pages 169-199 (Academic Press 1985); Coumailleau et al., *J. Biol. Chem.* 270:29270 (1995); Fukunaga et al., *J. Biol. Chem.* 270:25291 (1995); Yamaguchi et al., *Biochem. Pharmacol.* 50:1295 (1995); and Meisel et al., *Plant Molec. Biol.* 30:1 (1996).

Multiple amino acid substitutions can be made and tested using known methods of mutagenesis and screening, such as those disclosed by Reidhaar-Olson and Sauer (Science 241: 53-57, 1988) or Bowie and Sauer (*Proc. Natl. Acad. Sci. USA* 86:2152-2156, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832-10837, 1991; Ladner et al., U.S. Pat. No. 5,223,409; Huse, WIPO Publication WO 92/062045) and region-directed mutagenesis (Derbyshire et al., *Gene* 46:145, 1986; Ner et al., *DNA* 7:127, 1988).

Variants of the disclosed zalpha11 DNA and polypeptide sequences can be generated through DNA shuffling as disclosed by Stemmer, *Nature* 370:389-91, 1994, Stemmer, *Proc. Natl. Acad. Sci. USA* 91:10747-51, 1994 and WIPO Publication WO 97/20078. Briefly, variant DNAs are generated by in vitro homologous recombination by random fragmentation of a parent DNA followed by reassembly using PCR, resulting in randomly introduced point mutations. This technique can be modified by using a family of parent DNAs, such as allelic variants or DNAs from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized zalpha11 receptor polypeptides in host cells. Preferred assays in this regard include cell proliferation assays and biosensor-based ligand-binding assays, which are described below. Mutagenized DNA molecules that encode active receptors or portions thereof (e.g., ligand-binding fragments, signaling domains, and the like) can be recovered from the host cells and rapidly sequenced using modern equipment. These methods allow the rapid determination of the importance of individual amino acid residues in a polypeptide of interest, and can be applied to polypeptides of unknown structure.

In addition, the proteins of the present invention (or polypeptide fragments thereof) can be joined to other bioactive molecules, particularly other cytokines, to provide multi-functional molecules. For example, one or more helices from zalpha11 can be joined to other cytokines to enhance their biological properties or efficiency of production.

The present invention thus provides a series of novel, hybrid molecules in which a segment comprising one or more of the helices of zalpha11 is fused to another polypeptide. Fusion is preferably done by splicing at the DNA level to allow expression of chimeric molecules in recombinant production systems. The resultant molecules are then assayed for such properties as improved solubility, improved stability, prolonged clearance half-life, improved expression and secretion levels, and pharmacodynamics. Such hybrid molecules may further comprise additional amino acid residues (e.g. a polypeptide linker) between the component proteins or polypeptides.

Using the methods discussed herein, one of ordinary skill in the art can identify and/or prepare a variety of polypeptide fragments or variants of SEQ ID NO:2 that retain the signal transduction or ligand binding activity. For example, one can make a zalpha11 "soluble receptor" by preparing a variety of polypeptides that are substantially homologous to the cytokine-binding domain (residues 20 (Cys) to 237 (His) of SEQ ID NO:2 or allelic variants or species orthologs thereof) and retain ligand-binding activity of the wild-type zalpha11 protein. Such polypeptides may include additional amino acids from, for example, part or all of the transmembrane and intracellular domains. Such polypeptides may also include additional polypeptide segments as generally disclosed herein such as labels, affinity tags, and the like.

For any zalpha11 polypeptide, including variants, soluble receptors, and fusion polypeptides or proteins, one of ordinary skill in the art can readily generate a fully degenerate polynucleotide sequence encoding that variant using the information set forth in Tables 1 and 2 above.

The zalpha11 polypeptides of the present invention, including full-length polypeptides, biologically active fragments, and fusion polypeptides, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., Molecular Cloning: *A Laboratory Manual,* 2nd ed., Cold Spring Harbor Laboratory Press, Cold Spring Harbor, N.Y., 1989, and Ausubel et al., eds., *Current Protocols in Molecular Biology*, John Wiley and Sons, Inc., NY, 1987.

In general, a DNA sequence encoding a zalpha11 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a zalpha11 polypeptide into the secretory pathway of a host cell, a secretory signal sequence (also known as a leader sequence, prepro sequence or pre sequence) is provided in the expression vector. The secretory signal sequence may be that of zalpha11, or may be derived from another secreted protein (e.g., t-PA) or synthesized de novo. The secretory signal sequence is operably linked to the zalpha11 DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain secretory signal sequences may be positioned elsewhere in the DNA sequence of interest (see, e.g., Welch et al., U.S. Pat. No. 5,037,743; Holland et al., U.S. Pat. No. 5,143,830).

Alternatively, the secretory signal sequence contained in the polypeptides of the present invention is used to direct other polypeptides into the secretory pathway. The present invention provides for such fusion polypeptides. A signal fusion polypeptide can be made wherein a secretory signal sequence derived from amino acid 1 (Met) to amino acid 19 (Gly) of SEQ ID NO:2 is operably linked to another polypeptide using methods known in the art and disclosed herein. The secretory signal sequence contained in the fusion polypeptides of the present invention is preferably fused amino-terminally to an additional peptide to direct the additional peptide into the secretory pathway. Such constructs have numerous applications known in the art. For example, these novel secretory signal sequence fusion constructs can direct the secretion of an active component of a normally non-secreted protein. Such fusions may be used in vivo or in vitro to direct peptides through the secretory pathway.

Cultured mammalian cells are suitable hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841-845, 1982), DEAE-dextran mediated transfection (Ausubel et al., ibid.), and liposome-mediated transfection (Hawley-Nelson et al., Focus 15:73, 1993; Ciccarone et al., *Focus* 15:80, 1993, and viral vectors (Miller and Rosman, *BioTechniques* 7:980-90, 1989; Wang and Finer, *Nature Med.* 2:714-716, 1996). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59-72, 1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Other higher eukaryotic cells can also be used as hosts, including plant cells, insect cells and avian cells. The use of *Agrobacterium rhizogenes* as a vector for expressing genes in plant cells has been reviewed by Sinkar et al., *J. Biosci.* (*Bangalore*) 11:47-58, 1987. Transformation of insect cells and production of foreign polypeptides therein is disclosed by Guarino et al., U.S. Pat. No. 5,162,222 and WIPO publication WO 94/06463. Insect cells can be infected with recombinant baculovirus, commonly derived from *Autographa californica* nuclear polyhedrosis virus (AcNPV). See, King, L. A. and Possee, R. D., *The Baculovirus Expression System: A Laboratory Guide*, London, Chapman & Hall; O'Reilly, D. R. et al., *Baculovirus Expression Vectors: A Laboratory Manual*, New York, Oxford University Press., 1994; and, Richardson, C. D., Ed., *Baculovirus Expression Protocols. Methods in Molecular Biology*, Totowa, N.J., Humana Press, 1995. A second method of making recombinant zalpha11 baculovirus utilizes a transposon-based system described by Luckow (Luckow, V. A, et al., *J Virol* 67:4566-79, 1993). This system, which utilizes transfer vectors, is sold in the Bac-to-Bac™ kit (Life Technologies, Rockville, Md.). This system utilizes a transfer vector, pFastBac1™ (Life Technologies) containing a Tn7 transposon to move the DNA encoding the zalpha11 polypeptide into a baculovirus genome maintained in *E. coli* as a large plasmid called a "bacmid." See, Hill-Perkins, M. S, and Possee, R. D., *J Gen Virol* 71:971-6, 1990; Bonning, B. C. et al., *J Gen Virol* 75:1551-6, 1994; and, Chazenbalk, G. D., and Rapoport, B., *J Biol Chem* 270:1543-9, 1995. In addition, transfer vectors can include an in-frame fusion with DNA encoding an epitope tag at the C- or N-terminus of the expressed zalpha11 polypeptide, for example, a Glu-Glu epitope tag (Grussenmeyer, T. et al., *Proc. Natl. Acad. Sci.* 82:7952-4, 1985). Using a technique known in the art, a transfer vector containing zalpha11 is transformed into *E. Coli*, and screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, e.g. Sf9 cells. Recombinant virus that expresses zalpha11 is subsequently produced. Recombinant viral stocks are made by methods commonly used in the art.

The recombinant virus is used to infect host cells, typically a cell line derived from the fall armyworm, *Spodoptera frugiperda*. See, in general, Glick and Pasternak, *Molecular Biotechnology: Principles and Applications of Recombinant DNA*, ASM Press, Washington, D.C., 1994. Another suitable cell line is the High FiveO™ cell line (Invitrogen) derived from *Trichoplusia ni* (U.S. Pat. No. 5,300,435). Commercially available serum-free media are used to grow and maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. Procedures used are generally described in available laboratory manuals (King, L. A. and Possee, R. D., ibid.; O'Reilly, D. R. et al., ibid.; Richardson, C. D., ibid.). Subsequent purification of the zalpha11 polypeptide from the supernatant can be achieved using methods described herein.

Fungal cells, including yeast cells, can also be used within the present invention. Yeast species of particular interest in this regard include *Saccharomyces cerevisiae, Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459-3465, 1986 and Cregg, U.S. Pat. No. 4,882,279. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533.

The use of *Pichia methanolica* as host for the production of recombinant proteins is disclosed in WIPO Publications WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Prokaryotic host cells, including strains of the bacteria *Escherichia coli, Bacillus* and other genera are also useful host cells within the present invention. Techniques for transforming these hosts and expressing foreign DNA sequences cloned therein are well known in the art (see, e.g., Sambrook et al., ibid.). When expressing a zalpha11 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine and 0.006% L-leucine).

Within one aspect of the present invention, a zalpha11 cytokine receptor (including transmembrane and intracellular domains) is produced by a cultured cell, and the cell is used to screen for ligands for the receptor, including the natural ligand, as well as agonists and antagonists of the natural ligand. To summarize this approach, a cDNA or gene encoding the receptor is combined with other genetic elements required for its expression (e.g., a transcription promoter), and the resulting expression vector is inserted into a host cell. Cells that express the DNA and produce functional receptor are selected and used within a variety of screening systems.

Mammalian cells suitable for use in expressing the novel receptors of the present invention and transducing a receptor-mediated signal include cells that express a β-subunit, such as gp130, and cells that co-express gp130 and LIF receptor (Gearing et al., *EMBO J.* 10:2839-2848, 1991; Gearing et al., U.S. Pat. No. 5,284,755). In this regard it is generally preferred to employ a cell that is responsive to other cytokines that bind to receptors in the same subfamily, such as IL-6 or LIF, because such cells will contain the requisite signal transduction pathway(s). Preferred cells of this type include the human TF-1 cell line (ATCC number CRL-2003) and the DA-1 cell line (Branch et al., *Blood* 69:1782, 1987; Broudy et al., *Blood* 75:1622-1626, 1990). In the alternative, suitable host cells can be engineered to produce a β-subunit or other cellular component needed for the desired cellular response. For example, the murine cell line BaF3 (Palacios and Steinmetz, *Cell* 41:727-734, 1985; Mathey-Prevot et al., *Mol. Cell. Biol.* 6: 4133-4135, 1986), a baby hamster kidney (BHK) cell line, or the CTLL-2 cell line (ATCC TIB-214) can be transfected to express the mouse gpl 30 subunit, or mouse gp130 and LIF receptor, in addition to zalpha11. It is generally preferred to use a host cell and receptor(s) from the same species, however this approach allows cell lines to be engineered to express multiple receptor subunits from any species, thereby overcoming potential limitations arising from species specificity. In the alternative, species homologs of the human receptor cDNA can be cloned and used within cell lines from the same species, such as a mouse cDNA in the BaF3 cell line. Cell lines that are dependent upon one hematopoietic growth factor, such as IL-3, can thus be engineered to become dependent upon a zalpha11 ligand.

Cells expressing functional zalpha11 are used within screening assays. A variety of suitable assays are known in the art. These assays are based on the detection of a biological response in the target cell. One such assay is a cell proliferation assay. Cells are cultured in the presence or absence of a test compound, and cell proliferation is detected by, for example, measuring incorporation of tritiated thymidine or by colorimetric assay based on the metabolic breakdown of Alymar Blue™ (AccuMed, Chicago, Ill.) or 3-(4,5-dimethylthiazol-2-yl)-2,5-diphenyl tetrazolium bromide (MTT) (Mosman, *J. Immunol. Meth.* 65: 55-63, 1983). An alternative assay format uses cells that are further engineered to express a reporter gene. The reporter gene is linked to a promoter element that is responsive to the receptor-linked pathway, and the assay detects activation of transcription of the reporter gene. A preferred promoter element in this regard is a serum response element, or SRE (see, for example, Shaw et al., *Cell* 56:563-572, 1989). A preferred such reporter gene is a luciferase gene (de Wet et al., *Mol. Cell. Biol.* 7:725, 1987). Expression of the luciferase gene is detected by luminescence using methods known in the art (e.g., Baumgartner et al., *J. Biol. Chem.* 269:19094-29101, 1994; Schenborn and Goiffin, *Promega Notes* 41:11, 1993). Luciferase assay kits are commercially available from, for example, Promega Corp., Madison, Wis. Target cell lines of this type can be used to screen libraries of chemicals, cell-conditioned culture media, fungal broths, soil samples, water samples, and the like. For example, a bank of cell- or tissue-conditioned media samples can be assayed on a target cell to identify cells that produce ligand. Positive cells are then used to produce a cDNA library in a mammalian cell expression vector, which is divided into pools, transfected into host cells, and expressed. Media samples from the transfected cells are then assayed, with subsequent division of pools, retransfection, subculturing, and re-assay of positive cells to isolate a clonal cell line expressing the ligand. Media samples conditioned by kidney, liver, spleen, thymus, other lymphoid tissues, or T-cells are preferred sources of ligand for use in screening procedures.

A natural ligand for zalpha11 can also be identified by mutagenizing a cytokine-dependent cell line expressing zalpha11 and culturing it under conditions that select for autocrine growth. See WIPO publication WO 95/21930. Within a typical procedure, cells expressing zalpha11 are mutagenized, such as with EMS. The cells are then allowed to recover in the presence of the required cytokine, then transferred to a culture medium lacking the cytokine. Surviving cells are screened for the production of a ligand for zalpha11, such as by adding soluble (ligand-binding) receptor polypeptide to the culture medium or by assaying conditioned media on wild-type cells and transfected cells expressing the zalpha11. Preferred cell lines for use within this method include cells that are transfected to express gp130 or gp130 in combination with LIF receptor. Preferred such host cell lines include transfected CTLL-2 cells (Gillis and Smith, *Nature* 268:154-156, 1977) and transfected BaF3 cells.

Moreover, a secretion trap method employing zalpha11 soluble receptor polypeptide can be used to isolate a zalpha11 ligand (Aldrich, et al, *Cell* 87: 1161-1169, 1996). A cDNA expression library prepared from a known or suspected ligand source is transfected into COS-7 cells. The cDNA library vector generally has an SV40 origin for amplification in COS-7 cells, and a CMV promoter for high expression. The transfected COS-7 cells are grown in a monolayer and then fixed and permeabilized. Tagged or biotin-labeled zalpha11 soluble receptor, described herein, is then placed in contact with the cell layer and allowed to bind cells in the monolayer that express an anti-complementary molecule, i.e., a zalpha11 ligand. A cell expressing a ligand will thus be bound with receptor molecules. An anti-tag antibody (anti-Ig for Ig fusions, M2 or anti-FLAG for FLAG-tagged fusions, streptavidin, and the like) which is conjugated with horseradish peroxidase (HRP) is used to visualize these cells to which the tagged or biotin-labeled zalpha11 soluble receptor has bound. The HRP catalyzes deposition of a tyramide reagent, for example, tyramide-FITC. A commercially-available kit can be used for this detection (for example, Renaissance TSA-Direct™ Kit; NEN Life Science Products, Boston, Mass.). Cells which express zalpha11 receptor ligand will be identified under fluorescence microscopy as green cells and picked for subsequent cloning of the ligand using procedures for plasmid rescue as outlined in Aldrich, et al, supra., followed by subsequent rounds of secretion trap assay until single clones are identified.

As a receptor, the activity of zalpha11 polypeptide can be measured by a silicon-based biosensor microphysiometer which measures the extracellular acidification rate or proton excretion associated with receptor binding and subsequent physiologic cellular responses. An exemplary device is the Cytosensor™ Microphysiometer manufactured by Molecular Devices, Sunnyvale, Calif. A variety of cellular responses, such as cell proliferation, ion transport, energy production, inflammatory response, regulatory and receptor activation, and the like, can be measured by this method. See, for example, McConnell, H. M. et al., *Science* 257:1906-1912, 1992; Pitchford, S. et al., *Meth. Enzymol.* 228:84-108, 1997; Arimilli, S. et al., *J. Immunol. Meth.* 212:49-59, 1998; Van Liefde, I. Et al., *Eur. J. Pharmacol.* 346:87-95, 1998. The microphysiometer can be used for assaying eukaryotic, prokaryotic, adherent or non-adherent cells. By measuring extracellular acidification changes in cell media over time, the microphysiometer directly measures cellular responses to various stimuli, including agonists, ligands, or antagonists of the zalpha11 polypeptide. Preferably, the microphysiometer is used to measure responses of a zalpha11-expressing eukaryotic cell, compared to a control eukaryotic cell that does not express zalpha11 polypeptide. Zalpha11-expressing eukaryotic cells comprise cells into which zalpha11 has been transfected, as described herein, creating a cell that is responsive to zalpha11-modulating stimuli, or are cells naturally expressing zalpha11, such as zalpha11-expressing cells derived from lymphoid, spleen, thymus tissue or PBLs. Differences, measured by an increase or decrease in extracellular acidification, in the response of cells expressing zalpha11, relative to a control, are a direct measurement of zalpha11-modulated cellular responses. Moreover, such zalpha11-modulated responses can be assayed under a variety of stimuli. Also, using the microphysiometer, there is provided a method of identifying agonists and antagonists of zalpha11 polypeptide, comprising providing cells expressing a zalpha11 polypeptide, culturing a first portion of the cells in the absence of a test compound, culturing a second portion of the cells in the presence of a test compound, and detecting an increase or a decrease in a cellular response of the second portion of the cells as compared to the first portion of the cells. Antagonists and agonists, including the natural ligand for zalpha11 polypeptide, can be rapidly identified using this method.

Additional assays provided by the present invention include the use of hybrid receptor polypeptides. These hybrid polypeptides fall into two general classes. Within the first class, the intracellular domain of zalpha11, comprising approximately residues 256 (Lys) to 528 (Ser) of SEQ ID NO:2, is joined to the ligand-binding domain of a second receptor. It is preferred that the second receptor be a hematopoietic cytokine receptor, such as mpl receptor (Souyri et al., *Cell* 63:1137-1147, 1990). The hybrid receptor will further comprise a transmembrane domain, which may be derived from either receptor. A DNA construct encoding the hybrid receptor is then inserted into a host cell. Cells expressing the hybrid receptor are cultured in the presence of a ligand for the binding domain and assayed for a response. This system provides a means for analyzing signal transduction mediated by zalpha11 while using readily available ligands. This system can also be used to determine if particular cell lines are capable of responding to signals transduced by zalpha11. A second class of hybrid receptor polypeptides comprise the extracellular (ligand-binding) domain of zalpha11 (approximately residues 20 (Cys) to 237 (His) of SEQ ID NO:2) with a cytoplasmic domain of a second receptor, preferably a cytokine receptor, and a transmembrane domain. The transmembrane domain may be derived from either receptor. Hybrid receptors of this second class are expressed in cells known to be capable of responding to signals transduced by the second receptor. Together, these two classes of hybrid receptors enable the use of a broad spectrum of cell types within receptor-based assay systems.

Cells found to express a ligand for zalpha11 are then used to prepare a cDNA library from which the ligand-encoding cDNA may be isolated as disclosed above. The present invention thus provides, in addition to novel receptor polypeptides, methods for cloning polypeptide ligands for the receptors.

The tissue specificity of zalpha11 expression suggests a role in early thymocyte development and immune response regulation. These processes involve stimulation of cell proliferation and differentiation in response to the binding of one or more cytokines to their cognate receptors. In view of the tissue distribution observed for this receptor, agonists (including the natural ligand) and antagonists have enormous potential in both in vitro and in vivo applications. Compounds identified as receptor agonists are useful for stimulating proliferation and development of target cells in vitro and in vivo. For example, agonist compounds are useful as components of defined cell culture media, and may be used alone or in combination with other cytokines and hormones to replace serum that is commonly used in cell culture. Agonists are thus useful in specifically promoting the growth and/or development of T-cells, B-cells, and other cells of the lymphoid and myeloid lineages, and hematopoietic cells in culture.

Agonist ligands for zalpha11 may be useful in stimulating cell-mediated immunity and for stimulating lymphocyte proliferation, such as in the treatment of infections involving immunosuppression, including certain viral infections. Additional uses include tumor suppression, where malignant transformation results in tumor cells that are antigenic. Agonist ligands could be used to induce cytotoxicity, which may be mediated through activation of effector cells such as T-cells, NK (natural killer) cells, or LAK (lymphoid activated killer) cells, or induced directly through apoptotic pathways. Agonist ligands may also be useful in treating leukopenias by increasing the levels of the affected cell type, and for enhancing the regeneration of the T-cell repertoire after bone marrow transplantation.

Antagonist ligands or compounds may find utility in the suppression of the immune system, such as in the treatment of autoimmune diseases, including rheumatoid arthritis, multiple sclerosis, diabetes mellitis, inflammatory bowel disease, Crohn's disease, etc. Immune suppression can also be used to reduce rejection of tissue or organ transplants and grafts and to treat T-cell specific leukemias or lymphomas by inhibiting proliferation of the affected cell type.

Zalpha11 may also be used within diagnostic systems for the detection of circulating levels of ligand. Within a related embodiment, antibodies or other agents that specifically bind to zalpha11 can be used to detect circulating receptor polypeptides. Elevated or depressed levels of ligand or receptor polypeptides may be indicative of pathological conditions, including cancer. Soluble receptor polypeptides may contribute to pathologic processes and can be an indirect marker of an underlying disease. For example, elevated levels of soluble IL-2 receptor in human serum have been associated with a wide variety of inflammatory and neoplastic conditions, such as myocardial infarction, asthma, myasthenia gravis, rheumatoid arthritis, acute T-cell leukemia, B-cell lymphomas, chronic lymphocytic leukemia, colon cancer, breast cancer, and ovarian cancer (Heaney et al., *Blood* 87:847-857, 1996).

A ligand-binding polypeptide of a zalpha11 receptor, or "soluble receptor," can be prepared by expressing a truncated DNA encoding the zalpha11 cytokine binding domain (approximately residue 20 (Cys) through residue 237 (His) of the human receptor (SEQ ID NO:2)) or the corresponding region of a non-human receptor. It is preferred that the extracellular domain be prepared in a form substantially free of transmembrane and intracellular polypeptide segments. Moreover, ligand-binding polypeptide fragments within the zalpha11 cytokine binding domain, described above, can also serve as zalpha11 soluble receptors for uses described herein. To direct the export of a receptor polypeptide from the host cell, the receptor DNA is linked to a second DNA segment encoding a secretory peptide, such as a t-PA secretory peptide or a zalpha11 secretory peptide. To facilitate purification of the secreted receptor polypeptide, a C-terminal extension, such as a poly-histidine tag, substance P, Flag™ peptide (Hopp et al., *Bio/Technology* 6:1204-1210, 1988; available from Eastman Kodak Co., New Haven, Conn.) or another polypeptide or protein for which an antibody or other specific binding agent is available, can be fused to the receptor polypeptide.

In an alternative approach, a receptor extracellular domain can be expressed as a fusion with immunoglobulin heavy chain constant regions, typically an $F_c$ fragment, which contains two constant region domains and lacks the variable region. Such fusions are typically secreted as multimeric molecules wherein the Fc portions are disulfide bonded to each other and two receptor polypeptides are arrayed in close proximity to each other. Fusions of this type can be used to affinity purify the cognate ligand from solution, as an in vitro assay tool, to block signals in vitro by specifically titrating out ligand, and as antagonists in vivo by administering them parenterally to bind circulating ligand and clear it from the circulation. To purify ligand, a zalpha11-Ig chimera is added to a sample containing the ligand (e.g., cell-conditioned culture media or tissue extracts) under conditions that facilitate receptor-ligand binding (typically near-physiological temperature, pH, and ionic strength). The chimera-ligand complex is then separated by the mixture using protein A, which is immobilized on a solid support (e.g., insoluble resin beads). The ligand is then eluted using conventional chemical techniques, such as with a salt or pH gradient. In the alternative, the chimera itself can be bound to a solid support, with binding and elution carried out as above. Collected fractions can be re-fractionated until the desired level of purity is reached.

Moreover, zalpha11 soluble receptors can be used as a "ligand sink," i.e., antagonist, to bind ligand in vivo or in vitro in therapeutic or other applications where the presence of the ligand is not desired. For example, in cancers that are expressing large amount of bioactive zalpha11 ligand, zalpha11 soluble receptors can be used as a direct antagonist of the ligand in vivo, and may aid in reducing progression and symptoms associated with the disease. Moreover, zalpha11 soluble receptor can be used to slow the progression of cancers that over-express zalpha11 receptors, by binding ligand in vivo that would otherwise enhance proliferation of those cancers. Similar in vitro applications for a zalpha11 soluble receptor can be used, for instance, as a negative selection to select cell lines that grow in the absence of zalpha11 ligand.

Moreover, zalpha11 soluble receptor can be used in vivo or in diagnostic applications to detect zalpha11 ligand-expressing cancers in vivo or in tissue samples. For example, the zalpha11 soluble receptor can be conjugated to a radio-label or fluorescent label as described herein, and used to detect the presence of the ligand in a tissue sample using an in vitro ligand-receptor type binding assay, or fluorescent imaging assay. Moreover, a radio-labeled zalpha11 soluble receptor could be administered in vivo to detect ligand-expressing solid tumors through a radio-imaging method known in the art.

Analysis of the tissue distribution of the mRNA corresponding to this novel DNA showed expression in lymphoid tissues, including thymus, spleen, lymph nodes, and peripheral blood leukocytes. These data indicate a role for the zalpha11 receptor in proliferation, differentiation, and/or activation of immune cells, and suggest a role in development and regulation of immune responses. The data also suggest that the interaction of zalpha11 with its ligand may stimulate proliferation and development of myeloid cells and may, like IL-2, IL-6, LIF, IL-11 and OSM (Baumann et al., *J. Biol. Chem.* 268:8414-8417, 1993), induce acute-phase protein synthesis in hepatocytes.

It is preferred to purify the polypeptides of the present invention to 80% purity, more preferably to ≧90% purity, even more preferably ≧95% purity, and particularly preferred is a pharmaceutically pure state, that is greater than 99.9% pure with respect to contaminating macromolecules, particularly other proteins and nucleic acids, and free of infectious and pyrogenic agents. Preferably, a purified polypeptide is substantially free of other polypeptides, particularly other polypeptides of animal origin.

Expressed recombinant zalpha11 polypeptides (or zalpha11 chimeric or fusion polypeptides) can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding receptor polypeptides to support media are well known in the art. Selection of a particular method is a matter of routine design and is determined in part by the properties of the chosen support. See, for example, *Affinity Chromatography: Principles & Methods*, Pharmacia LKB Biotechnology, Uppsala, Sweden, 1988.

The polypeptides of the present invention can be isolated by exploitation of their biochemical, structural, and biological properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1-7, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (*Methods in Enzymol*., Vol. 182, "Guide to Protein Purification", M. Deutscher, (ed.), Acad. Press, San Diego, 1990, pp. 529-39). Within additional embodiments of the invention, a fusion of the polypeptide of interest and an affinity tag (e.g., maltose-binding protein, an immunoglobulin domain) may be constructed to facilitate purification.

Moreover, using methods described in the art, polypeptide fusions, or hybrid zalpha11 proteins, are constructed using regions or domains of the inventive zalpha11 in combination with those of other human cytokine receptor family proteins, or heterologous proteins (Sambrook et al., ibid., Altschul et al., ibid., Picard, *Cur. Opin. Biology,* 5:511-5, 1994, and references therein). These methods allow the determination of the biological importance of larger domains or regions in a polypeptide of interest. Such hybrids may alter reaction kinetics, binding, constrict or expand the substrate specificity, or alter tissue and cellular localization of a polypeptide, and can be applied to polypeptides of unknown structure.

Fusion polypeptides or proteins can be prepared by methods known to those skilled in the art by preparing each component of the fusion protein and chemically conjugating them. Alternatively, a polynucleotide encoding one or more components of the fusion protein in the proper reading frame can be generated using known techniques and expressed by the methods described herein. For example, part or all of a domain(s) conferring a biological function may be swapped between zalpha11 of the present invention with the functionally equivalent domain(s) from another cytokine family member. Such domains include, but are not limited to, the secretory signal sequence, extracellular cytokine binding domain, transmembrane domain, and intracellular signaling domain, Box I and Box II sites, as disclosed herein. Such fusion proteins would be expected to have a biological functional profile that is the same or similar to polypeptides of the present invention or other known family proteins, depending on the fusion constructed. Moreover, such fusion proteins may exhibit other properties as disclosed herein.

Standard molecular biological and cloning techniques can be used to swap the equivalent domains between the zalpha11 polypeptide and those polypeptides to which they are fused. Generally, a DNA segment that encodes a domain of interest, e.g., a zalpha11 domain described herein, is operably linked in frame to at least one other DNA segment encoding an additional polypeptide (for instance a domain or region from another cytokine receptor, such as the IL-2 receptor), and inserted into an appropriate expression vector, as described herein. Generally DNA constructs are made such that the several DNA segments that encode the corresponding regions of a polypeptide are operably linked in frame to make a single construct that encodes the entire fusion protein, or a functional portion thereof. For example, a DNA construct would encode from N-terminus to C-terminus a fusion protein comprising a signal polypeptide followed by a cytokine binding domain, followed by a transmembrane domain, followed by an intracellular signaling domain. Such fusion proteins can be expressed, isolated, and assayed for activity as described herein.

Zalpha11 polypeptides or fragments thereof may also be prepared through chemical synthesis. zalpha11 polypeptides may be monomers or multimers; glycosylated or non-glycosylated; pegylated or non-pegylated; and may or may not include an initial methionine amino acid residue.

Polypeptides of the present invention can also be synthesized by exclusive solid phase synthesis, partial solid phase methods, fragment condensation or classical solution synthesis. Methods for synthesizing polypeptides are well known in the art. See, for example, Merrifield, *J. Am. Chem. Soc.* 85:2149, 1963; Kaiser et al., *Anal. Biochem.* 34:595, 1970. After the entire synthesis of the desired peptide on a solid support, the peptide-resin is with a reagent which cleaves the polypeptide from the resin and removes most of the side-chain protecting groups. Such methods are well established in the art.

The activity of molecules of the present invention can be measured using a variety of assays that measure cell differentiation and proliferation. Such assays are well known in the art.

Proteins of the present invention are useful for example, in treating lymphoid, immune, inflammatory, spleenic, blood or bone disorders, and can be measured in vitro using cultured cells or in vivo by administering molecules of the claimed invention to the appropriate animal model. For instance, host cells expressing a zalpha11 soluble receptor polypeptide can be embedded in an alginate environment and injected (implanted) into recipient animals. Alginate-poly-L-lysine microencapsulation, permselective membrane encapsulation and diffusion chambers are a means to entrap transfected mammalian cells or primary mammalian cells. These types of non-immunogenic "encapsulations" permit the diffusion of proteins and other macromolecules secreted or released by the captured cells to the recipient animal. Most importantly, the capsules mask and shield the foreign, embedded cells from the recipient animal's immune response. Such encapsulations can extend the life of the injected cells from a few hours or days (naked cells) to several weeks (embedded cells). Alginate threads provide a simple and quick means for generating embedded cells.

The materials needed to generate the alginate threads are known in the art. In an exemplary procedure, 3% alginate is prepared in sterile $H_2O$, and sterile filtered. Just prior to preparation of alginate threads, the alginate solution is again filtered. An approximately 50% cell suspension (containing about $5\times10^5$ to about $5\times10^7$ cells/ml) is mixed with the 3% alginate solution. One ml of the alginate/cell suspension is extruded into a 100 mM sterile filtered $CaCl_2$ solution over a time period of ~15 min, forming a "thread". The extruded thread is then transferred into a solution of 50 mM $CaCl_2$, and then into a solution of 25 mM $CaCl_2$. The thread is then rinsed with deionized water before coating the thread by incubating in a 0.01% solution of poly-L-lysine. Finally, the thread is rinsed with Lactated Ringer's Solution and drawn from solution into a syringe barrel (without needle). A large bore needle is then attached to the syringe, and the thread is intraperitoneally injected into a recipient in a minimal volume of the Lactated Ringer's Solution.

An in vivo approach for assaying proteins of the present invention involves viral delivery systems. Exemplary viruses for this purpose include adenovirus, herpesvirus, retroviruses, vaccinia virus, and adeno-associated virus (AAV). Adenovirus, a double-stranded DNA virus, is currently the best studied gene transfer vector for delivery of heterologous nucleic acid (for review, see T. C. Becker et al., *Meth. Cell Biol.* 43:161-89, 1994; and J. T. Douglas and D. T. Curiel, *Science & Medicine* 4:44-53, 1997). The adenovirus system offers several advantages: (i) adenovirus can accommodate relatively large DNA inserts; (ii) can be grown to high-titer; (iii) infect a broad range of mammalian cell types; and (iv) can be used with a large number of different promoters including ubiquitous, tissue specific, and regulatable promoters. Also, because adenoviruses are stable in the bloodstream, they can be administered by intravenous injection.

Using adenovirus vectors where portions of the adenovirus genome are deleted, inserts are incorporated into the viral DNA by direct ligation or by homologous recombination with a co-transfected plasmid. In an exemplary system, the essential E1 gene has been deleted from the viral vector, and the virus will not replicate unless the E1 gene is provided by the host cell (the human 293 cell line is exemplary). When intravenously administered to intact animals, adenovirus primarily targets the liver. If the adenoviral delivery system has an E1 gene deletion, the virus cannot replicate in the host cells. However, the host's tissue (e.g., liver) will express and process (and, if a secretory signal sequence is present, secrete) the heterologous protein. Secreted proteins will enter the circulation in the highly vascularized liver, and effects on the infected animal can be determined.

Moreover, adenoviral vectors containing various deletions of viral genes can be used in an attempt to reduce or eliminate immune responses to the vector. Such adenoviruses are E1 deleted, and in addition contain deletions of E2A or E4 (Lusky, M. et al., *J. Virol.* 72:2022-2032, 1998; Raper, S. E. et al., *Human Gene Therapy* 9:671-679, 1998). In addition, deletion of E2b is reported to reduce immune responses (Amalfitano, A. et al., *J. Virol.* 72:926-933, 1998). Moreover, by deleting the entire adenovirus genome, very large inserts of heterologous DNA can be accommodated. Generation of so called "gutless" adenoviruses where all viral genes are deleted are particularly advantageous for insertion of large inserts of heterologous DNA. For review, see Yeh, P. and Perricaudet, M., *FASEB J.* 11:615-623, 1997.

The adenovirus system can also be used for protein production in vitro. By culturing adenovirus-infected non-293 cells under conditions where the cells are not rapidly dividing, the cells can produce proteins for extended periods of time. For instance, BHK cells are grown to confluence in cell factories, then exposed to the adenoviral vector encoding the secreted protein of interest. The cells are then grown under serum-free conditions, which allows infected cells to survive for several weeks without significant cell division. Alternatively, adenovirus vector infected 293 cells can be grown as adherent cells or in suspension culture at relatively high cell density to produce significant amounts of protein (See Gartner et al., *Cytotechnol.* 15:145-55, 1994). With either protocol, an expressed, secreted heterologous protein can be repeatedly isolated from the cell culture supernatant, lysate, or membrane fractions depending on the disposition of the expressed protein in the cell. Within the infected 293 cell production protocol, non-secreted proteins may also be effectively obtained.

In view of the tissue distribution observed for zalpha11, agonists (including the natural ligand/substrate/cofactor/etc.) and antagonists have enormous potential in both in vitro and in vivo applications. Compounds identified as zalpha11 agonists are useful for stimulating growth of immune and hematopoietic cells in vitro and in vivo. For example, zalpha11 and agonist compounds are useful as components of defined cell culture media, and may be used alone or in combination with other cytokines and hormones to replace serum that is commonly used in cell culture. Agonists are thus useful in specifically promoting the growth and/or development of T-cells, B-cells, and other cells of the lymphoid and myeloid lineages in culture. Moreover, zalpha11 soluble receptor, agonist, or antagonist may be used in vitro in an assay to measure stimulation of colony formation from isolated primary bone marrow cultures. Such assays are well known in the art.

Antagonists are also useful as research reagents for characterizing sites of ligand-receptor interaction. Inhibitors of zalpha11 activity (zalpha11 antagonists) include anti-zalpha11 antibodies and soluble zalpha11 receptors, as well as other peptidic and non-peptidic agents (including ribozymes).

Zalpha11 can also be used to identify modulators (e.g, antagonists) of its activity. Test compounds are added to the assays disclosed herein to identify compounds that inhibit the activity of zalpha11. In addition to those assays disclosed herein, samples can be tested for inhibition of zalpha11 activity within a variety of assays designed to measure zalpha11 binding, oligomerization, or the stimulation/inhibition of zalpha11-dependent cellular responses. For example, zalpha11-expressing cell lines can be transfected with a reporter gene construct that is responsive to a zalpha11-stimulated cellular pathway. Reporter gene constructs of this type are known in the art, and will generally comprise a zalpha11-DNA response element operably linked to a gene encoding an assay detectable protein, such as luciferase. DNA response elements can include, but are not limited to, cyclic AMP response elements (CRE), hormone response elements (HRE) insulin response element (IRE) (Nasrin et al., *Proc. Natl. Acad. Sci. USA* 87:5273-7, 1990) and serum response elements (SRE) (Shaw et al. *Cell* 56: 563-72, 1989). Cyclic AMP response elements are reviewed in Roestler et al., *J. Biol. Chem.* 263 (19):9063-6; 1988 and Habener, *Molec. Endocrinol.* 4 (8):1087-94; 1990. Hormone response elements are reviewed in Beato, *Cell* 56:335-44; 1989. Candidate compounds, solutions, mixtures or extracts or conditioned media from various cell types are tested for the ability to enhance the activity of zalpha11 receptor as evidenced by a increase in zalpha11 stimulation of reporter gene expression. Assays of this type will detect compounds that directly stimulate zalpha11 signal transduction activity through binding the receptor or by otherwise stimulating part of the signal cascade. As such, there is provided a method of identifying agonists of zalpha11 polypeptide, comprising providing cells responsive to a zalpha11 polypeptide, culturing a first portion of the cells in the absence of a test compound, culturing a second portion of the cells in the presence of a test compound, and detecting a increase in a cellular response of the second portion of the cells as compared to the first portion of the cells. Moreover third cell, containing the reporter gene construct described above, but not expressing zaplpha11 receptor, can be used as a control cell to assess non-specific, or non-zalpha11-mediated, stimulation of the reporter. Agonists, including the natural ligand, are therefore useful to stimulate or increase zalpha11 polypeptide function.

A zalpha11 ligand-binding polypeptide, such as the cytokine binding domain disclosed herein, can also be used for purification of ligand. The polypeptide is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting medium will generally be configured in the form of a column, and fluids containing ligand are passed through the column one or more times to allow ligand to bind to the receptor polypeptide. The ligand is then eluted using changes in salt concentration, chaotropic agents (guanidine HCl), or pH to disrupt ligand-receptor binding.

An assay system that uses a ligand-binding receptor (or an antibody, one member of a complement/anti-complement pair) or a binding fragment thereof, and a commercially available biosensor instrument may be advantageously employed (e.g., BIAcore™, Pharmacia Biosensor, Piscataway, N.J.; or SELDI™ technology, Ciphergen, Inc., Palo Alto, Calif.). Such receptor, antibody, member of a complement/anti-complement pair or fragment is immobilized onto the surface of a receptor chip. Use of this instrument is disclosed by Karlsson, *J. Immunol. Methods* 145:229-240, 1991 and Cunningham and Wells, *J. Mol. Biol.* 234:554-63, 1993. A receptor, antibody, member or fragment is covalently attached, using amine or sulfhydryl chemistry, to dextran fibers that are attached to gold film within the flow cell. A test sample is passed through the cell. If a ligand, epitope, or opposite member of the complement/anti-complement pair is present in the sample, it will bind to the immobilized receptor, antibody or member, respectively, causing a change in the refractive index of the medium, which is detected as a change in surface plasmon resonance of the gold film. This system allows the determination of on- and off-rates, from which binding affinity can be calculated, and assessment of stoichiometry of binding.

Ligand-binding receptor polypeptides can also be used within other assay systems known in the art. Such systems include Scatchard analysis for determination of binding affinity (see Scatchard, *Ann. NY Acad. Sci.* 51: 660-672, 1949) and calorimetric assays (Cunningham et al., *Science* 253:545-48, 1991; Cunningham et al., *Science* 245:821-25, 1991).

Zalpha11 polypeptides can also be used to prepare antibodies that bind to zalpha11 epitopes, peptides or polypeptides. The zalpha11 polypeptide or a fragment thereof serves as an antigen (immunogen) to inoculate an animal and elicit an immune response. One of skill in the art would recognize that antigens or immunogenic epitopes can consist of stretches of amino acids within a longer polypeptide, from about 10 amino acids and up to about the entire length of the polypeptide or longer depending on the polypeptide. Suitable antigens include the zalpha11 polypeptide encoded by SEQ ID NO:2 from amino acid number 20 (Cys) to amino acid number 538 (Ser), or a contiguous 9 to 519 AA amino acid fragment thereof. Preferred peptides to use as antigens are the cytokine binding domain, intracellular signaling domain, Box I and Box II sites, disclosed herein, and zalpha11 hydrophilic peptides such as those predicted by one of skill in the art from a hydrophobicity plot, determined for example, from a Hopp/Woods hydrophilicity profile based on a sliding six-residue window, with buried G, S, and T residues and exposed H, Y, and W residues ignored (See, FIG. 1). Zalpha11 hydrophilic peptides include peptides comprising amino acid sequences selected from the group consisting of: (1) amino acid number 51 (Trp) to amino acid number 61 (Glu) of SEQ ID NO:2; (2) amino acid number 136 (Ile) to amino acid number 143 (Glu) of SEQ ID NO:2; (3) amino acid number 187 (Pro) to amino acid number 195 (Ser) of SEQ ID NO:2; (4) amino acid number 223 (Phe) to amino acid number 232 (Glu) of SEQ ID NO:2; and (5) amino acid number 360 (Glu) to amino acid number 368 (Asp) of SEQ ID NO:2. In addition, conserved motifs, and variable regions between conserved motifs of zalpha11 are suitable antigens. Moreover, corresponding regions of the mouse zalpha11 polypeptide (SEQ ID NO:85) can be used to generate antibodies against the mouse zalpha11. Antibodies generated from this immune response can be isolated and purified as described herein. Methods for preparing and isolating polyclonal and monoclonal antibodies are well known in the art. See, for example, *Current Protocols in Immunology*, Cooligan, et al. (eds.), National Institutes of Health, John Wiley and Sons, Inc., 1995; Sambrook et al., *Molecular Cloning: A Laboratory Manual, Second Edition*, Cold Spring Harbor, N.Y., 1989; and Hurrell, J. G. R., Ed., *Monoclonal Hybridoma Antibodies: Techniques and Applications*, CRC Press, Inc., Boca Raton, Fla., 1982.

As would be evident to one of ordinary skill in the art, polyclonal antibodies can be generated from inoculating a variety of warm-blooded animals such as horses, cows, goats, sheep, dogs, chickens, rabbits, mice, and rats with a zalpha11 polypeptide or a fragment thereof. The immunogenicity of a zalpha11 polypeptide may be increased through the use of an adjuvant, such as alum (aluminum hydroxide) or Freund's complete or incomplete adjuvant. Polypeptides useful for immunization also include fusion polypeptides, such as fusions of zalpha11 or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as $F(ab')_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced.

Alternative techniques for generating or selecting antibodies useful herein include in vitro exposure of lymphocytes to zalpha11 protein or peptide, and selection of antibody display libraries in phage or similar vectors (for instance, through use of immobilized or labeled zalpha11 protein or peptide). Genes encoding polypeptides having potential zalpha11 polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the zalpha11 sequences disclosed herein to identify proteins which bind to zalpha11. These "binding peptides" which interact with zalpha11 polypeptides can be used for tagging cells; for isolating homolog polypeptides by affinity purification; they can be directly or indirectly conjugated to drugs, toxins, radionuclides and the like. These binding peptides can also be used in analytical methods such as for screening expression libraries and neutralizing activity. The binding peptides can also be used for diagnostic assays for determining circulating levels of zalpha11 polypeptides; for detecting or quantitating soluble zalpha11 polypeptides as marker of underlying pathology or disease. These binding peptides can also act as zalpha11 "antagonists" to block zalpha11 binding and signal transduction in vitro and in vivo. These anti-zalpha11 binding peptides would be useful for inhibiting the action of a ligand that binds with zalpha11.

Antibodies are determined to be specifically binding if: 1) they exhibit a threshold level of binding activity, and/or 2) they do not significantly cross-react with related polypeptide molecules. First, antibodies herein specifically bind if they bind if they bind to a zalpha11 polypeptide, peptide or epitope with an affinity at least 10-fold greater than the binding affinity to control (non-zalpha11) polypeptide. It is preferred that the antibodies exhibit a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, G., *Ann. NY Acad. Sci.* 51: 660-672, 1949).

Second, antibodies are determined to specifically bind if they do not significantly cross-react with related polypeptides. Antibodies do not significantly cross-react with related polypeptide molecules, for example, if they detect zalpha11 but not known related polypeptides using a standard Western blot analysis (Ausubel et al., ibid.). Examples of known related polypeptides are orthologs, proteins from the same species that are members of a protein family (e.g. IL-6), zalpha11 polypeptides, and non-human zalpha11. Moreover, antibodies may be "screened against" known related polypeptides to isolate a population that specifically binds to the inventive polypeptides. For example, antibodies raised to zalpha11 are adsorbed to related polypeptides adhered to insoluble matrix; antibodies specific to zalpha11 will flow through the matrix under the proper buffer conditions. Such screening allows isolation of polyclonal and monoclonal antibodies non-crossreactive to closely related polypeptides (*Antibodies: A Laboratory Manual*, Harlow and Lane (eds.), Cold Spring Harbor Laboratory Press, 1988; *Current Protocols in Immunology*, Cooligan, et al. (eds.), National Institutes of Health, John Wiley and Sons, Inc., 1995). Screening and isolation of specific antibodies is well known in the art. See, *Fundamental Immunology*, Paul (eds.), Raven Press, 1993; Getzoff et al., *Adv. in Immunol.* 43: 1-98, 1988; *Monoclonal Antibodies: Principles and Practice*, Goding, J. W. (eds.), *Academic Press Ltd.,* 1996; Benjamin et al., *Ann. Rev. Immunol.* 2: 67-101, 1984.

A variety of assays known to those skilled in the art can be utilized to detect antibodies which specifically bind to zalpha11 proteins or peptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radioimmunoassay, radioimmuno-precipitation, enzyme-linked immunosorbent assay (ELISA), dot blot or Western blot assay, inhibition or competition assay, and sandwich assay. In addition, antibodies can be screened for binding to wild-type versus mutant zalpha11 protein or polypeptide.

Antibodies to zalpha11 may be used for tagging cells that express zalpha11; for isolating zalpha11 by affinity purification; for diagnostic assays for determining circulating levels of zalpha11 polypeptides; for detecting or quantitating soluble zalpha11 as marker of underlying pathology or disease; in analytical methods employing FACS; for screening expression libraries; for generating anti-idiotypic antibodies; and as neutralizing antibodies or as antagonists to block zalpha11 activity in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications. Moreover, antibodies to zalpha11 or fragments thereof may be used in vitro to detect denatured zalpha11 or fragments thereof in assays, for example, Western Blots or other assays known in the art.

Antibodies to zalpha11 are useful for tagging cells that express the receptor and assaying Zalpha11 expression levels, for affinity purification, within diagnostic assays for determining circulating levels of soluble receptor polypeptides, analytical methods employing fluorescence-activated cell sorting. Divalent antibodies may be used as agonists to mimic the effect of the zalpha11 ligand.

Antibodies herein can also be directly or indirectly conjugated to drugs, toxins, radionuclides and the like, and these conjugates used for in vivo diagnostic or therapeutic applications. For instance, antibodies or binding polypeptides which recognize zalpha11 of the present invention can be used to identify or treat tissues or organs that express a corresponding anti-complementary molecule (i.e., a zalpha11 receptor). More specifically, anti-zalpha11 antibodies, or bioactive fragments or portions thereof, can be coupled to detectable or cytotoxic molecules and delivered to a mammal having cells, tissues or organs that express the zalpha11 molecule.

Suitable detectable molecules may be directly or indirectly attached to polypeptides that bind zalpha11 ("binding polypeptides," including binding peptides disclosed above), antibodies, or bioactive fragments or portions thereof. Suitable detectable molecules include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria toxin, *Pseudomonas* exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Binding polypeptides or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the binding polypeptide or antibody portion. For these purposes, biotin/streptavidin is an exemplary complementary/anticomplementary pair.

In another embodiment, binding polypeptide-toxin fusion proteins or antibody-toxin fusion proteins can be used for targeted cell or tissue inhibition or ablation (for instance, to treat cancer cells or tissues). Alternatively, if the binding polypeptide has multiple functional domains (i.e., an activation domain or a ligand binding domain, plus a targeting domain), a fusion protein including only the targeting domain may be suitable for directing a detectable molecule, a cytotoxic molecule or a complementary molecule to a cell or tissue type of interest. In instances where the fusion protein including only a single domain includes a complementary molecule, the anti-complementary molecule can be conjugated to a detectable or cytotoxic molecule. Such domain-complementary molecule fusion proteins thus represent a generic targeting vehicle for cell/tissue-specific delivery of generic anti-complementary-detectable/cytotoxic molecule conjugates.

In another embodiment, zalpha11 binding polypeptide-cytokine or antibody-cytokine fusion proteins can be used for enhancing in vivo killing of target tissues (for example, blood, lymphoid, colon, and bone marrow cancers), if the binding polypeptide-cytokine or anti-zalpha11 antibody targets the hyperproliferative cell (See, generally, Hornick et al., *Blood* 89:4437-47, 1997). They described fusion proteins enable targeting of a cytokine to a desired site of action, thereby providing an elevated local concentration of cytokine. Suitable anti-zalpha11 antibodies target an undesirable cell or tissue (i.e., a tumor or a leukemia), and the fused cytokine mediates improved target cell lysis by effector cells. Suitable cytokines for this purpose include interleukin 2 and granulocyte-macrophage colony-stimulating factor (GM-CSF), for instance.

Alternatively, zalpha11 binding polypeptide or antibody fusion proteins described herein can be used for enhancing in vivo killing of target tissues by directly stimulating a zalpha11-modulated apoptotic pathway, resulting in cell death of hyperproliferative cells expressing zalpha11.

The bioactive binding polypeptide or antibody conjugates described herein can be delivered orally, intravenously, intraarterially or intraductally, or may be introduced locally at the intended site of action.

Four-helix bundle cytokines that bind to cytokine receptors as well as other proteins produced by activated lymphocytes play an important biological role in cell differentiation, activation, recruitment and homeostasis of cells throughout the body. Therapeutic utility includes treatment of diseases which require immune regulation including autoimmune diseases, such as, rheumatoid arthritis, multiple sclerosis, myasthenia gravis, systemic lupus erythomatosis and diabetes. Zalpha11 antagonists or agonists, including soluble receptors and the natural ligand, may be important in the regulation of inflammation, and therefore would be useful in treating rheumatoid arthritis, asthma, ulcerative colitis, inflammatory bowel disease, Crohn's disease, and sepsis. There may be a role of zalpha11 antagonists or agonists, including soluble receptors and the natural ligand, in mediating tumorgenesis, and therefore would be useful in the treatment of cancer. Zalpha11 antagonists or agonists, including soluble receptors and the natural ligand, may be a potential therapeutic in suppressing the immune system which would be important for reducing graft rejection. Zalpha11 Ligand may have usefulness in prevention of graft vs. host disease.

Alternatively, zalpha11 antagonists or agonists, including soluble receptors and the natural ligand may activate the immune system which would be important in boosting immunity to infectious diseases, treating immunocompromised patients, such as HIV+ patient, or in improving vaccines. In particular, zalpha11 antagonists or agonists, including soluble receptors and the natural ligand can modulate, stimulate or expand NK cells, or their progenitors, and would provide therapeutic value in treatment of viral infection, and as an anti-neoplastic factor. NK cells are thought to play a major role in elimination of metastatic tumor cells and patients with both metastases and solid tumors have decreased levels of NK cell activity (Whiteside et. al., *Curr. Top. Microbiol. Immunol.* 230:221-244, 1998).

Polynucleotides encoding zalpha11 polypeptides are useful within gene therapy applications where it is desired to increase or inhibit zalpha11 activity. If a mammal has a mutated or absent zalpha11 gene, the zalpha11 gene can be introduced into the cells of the mammal. In one embodiment, a gene encoding a zalpha11 polypeptide is introduced in vivo in a viral vector. Such vectors include an attenuated or defective DNA virus, such as, but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes simplex virus 1 (HSV1) vector (Kaplitt et al., *Molec. Cell. Neurosci.* 2:320-30, 1991); an attenuated adenovirus vector, such as the vector described by Stratford-Perricaudet et al., *J. Clin. Invest.* 90:626-30, 1992; and a defective adeno-associated virus vector (Samulski et al., *J. Virol.* 61:3096-101, 1987; Samulski et al., *J. Virol.* 63:3822-8, 1989).

In another embodiment, a zalpha11 gene can be introduced in a retroviral vector, e.g., as described in Anderson et al., U.S. Pat. No. 5,399,346; Mann et al. *Cell* 33:153, 1983; Temin et al., U.S. Pat. No. 4,650,764; Temin et al., U.S. Pat. No. 4,980,289; Markowitz et al., *J. Virol.* 62:1120, 1988; Temin et al., U.S. Pat. No. 5,124,263; International Patent Publication No. WO 95/07358, published Mar. 16, 1995 by Dougherty et al.; and Kuo et al., *Blood* 82:845, 1993. Alternatively, the vector can be introduced by lipofection in vivo using liposomes. Synthetic cationic lipids can be used to prepare liposomes for in vivo transfection of a gene encoding a marker (Feigner et al., *Proc. Natl. Acad. Sci. USA* 84:7413-7, 1987; Mackey et al., *Proc. Natl. Acad. Sci. USA* 85:8027-31, 1988). The use of lipofection to introduce exogenous genes into specific organs in vivo has certain practical advantages. Molecular targeting of liposomes to specific cells represents one area of benefit. More particularly, directing transfection to particular cells represents one area of benefit. For instance, directing transfection to particular cell types would be particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

It is possible to remove the target cells from the body; to introduce the vector as a naked DNA plasmid; and then to re-implant the transformed cells into the body. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., *J. Biol. Chem.* 267:963-7, 1992; Wu et al., *J. Biol. Chem.* 263:14621-4, 1988.

Antisense methodology can be used to inhibit zalpha11 gene transcription, such as to inhibit cell proliferation in vivo. Polynucleotides that are complementary to a segment of a zalpha11-encoding polynucleotide (e.g., a polynucleotide as set froth in SEQ ID NO:1) are designed to bind to zalpha11-encoding mRNA and to inhibit translation of such mRNA. Such antisense polynucleotides are used to inhibit expression of zalpha11 polypeptide-encoding genes in cell culture or in a subject.

In addition, as a cell surface molecule, zalpha11 polypeptide can be used as a target to introduce gene therapy into a cell. This application would be particularly appropriate for introducing therapeutic genes into cells in which zalpha11 is normally expressed, such as lymphoid tissue and PBLs, or cancer cells which express zalpha11 polypeptide. For example, viral gene therapy, such as described above, can be targeted to specific cell types in which express a cellular receptor, such as zalpha11 polypeptide, rather than the viral receptor. Antibodies, or other molecules that recognize zalpha11 molecules on the target cell's surface can be used to direct the virus to infect and administer gene therapeutic material to that target cell. See, Woo, S. L. C, *Nature Biotech.* 14:1538, 1996; Wickham, T. J. et al, *Nature Biotech.* 14:1570-1573, 1996; Douglas, J. T et al., *Nature Biotech.* 14:1574-1578, 1996; Rihova, B., *Crit. Rev. Biotechnol.* 17:149-169, 1997; and Vile, R. G. et al., *Mol. Med. Today* 4:84-92, 1998. For example, a bispecific antibody containing a virus-neutralizing Fab fragment coupled to a zalpha11-specific antibody can be used to direct the virus to cells expressing the zalpha11 receptor and allow efficient entry of the virus containing a genetic element into the cells. See, for example, Wickham, T. J., et al., *J. Virol.* 71:7663-7669, 1997; and Wickham, T. J., et al., *J. Virol.* 70:6831-6838, 1996.

The present invention also provides reagents which will find use in diagnostic applications. For example, the zalpha11 gene, a probe comprising zalpha11 DNA or RNA or a subsequence thereof can be used to determine if the zalpha11 gene is present on chromosome 16 or if a mutation has occurred. Zalpha11 is located at the 16p11.1 region of chromosome 16 (See, Example 3). Detectable chromosomal aberrations at the zalpha11 gene locus include, but are not limited to, aneuploidy, gene copy number changes, insertions, deletions, restriction site changes and rearrangements. Such aberrations can be detected using polynucleotides of the present invention by employing molecular genetic techniques, such as restriction fragment length polymorphism (RFLP) analysis, fluorescence in situ hybridization methods, short tandem repeat (STR) analysis employing PCR techniques, and other genetic linkage analysis techniques known in the art (Sambrook et al., ibid.; Ausubel et. al., ibid.; Marian, *Chest* 108: 255-65, 1995).

The precise knowledge of a gene's position can be useful for a number of purposes, including: 1) determining if a sequence is part of an existing contig and obtaining additional surrounding genetic sequences in various forms, such as YACs, BACs or cDNA clones; 2) providing a possible candidate gene for an inheritable disease which shows linkage to the same chromosomal region; and 3) cross-referencing model organisms, such as mouse, which may aid in determining what function a particular gene might have.

The zalpha11 gene is located at the 16p11.1 region of chromosome 16. Several genes of known function map to this region. For example, the interleukin 4 (IL-4) cytokine receptor alpha-subunit, a member of the hematopoietin receptor family, maps to 16p12.1-p11.2. This subunit may form a heterodimer with zalpha11. Moreover, zalpha11 polynucleotide probes can be used to detect abnormalities or genotypes associated with defects in IL-4 receptor, such as those that are implicated in some allergic inflammatory disorders and asthma (Deichman, K. A. et al., *Exp. Allergy* 28:151-155; 1998; Mitsuyasu, H. et al., *Nature Genet.* 19:119-120, 1998). In addition, zalpha11 polynucleotide probes can be used to detect abnormalities or genotypes associated with inflammatory bowel disease, where a susceptibility marker maps to 16p12-q13 (Cho, J. H. et al, *Proc. Nat. Acad. Sci.* 95:7502-7507, 1998). Further, zalpha11 polynucleotide probes can be used to detect abnormalities or genotypes associated with hemoglobin loci located at 16pter-p13.3, and particularly hemoglobin-alpha defects associated with alpha-thalassemia syndromes, such as hydrops fetalis (for review, see Chui, M. P., and Waye, J. S. *Blood* 91:2213-2222, 1998). Moreover, amongst other genetic loci, those for Wilms tumor, type III (16q), Rubenstein-Taybi syndrome (16p13.3), severe infantile polycystic kidney disease (16p13.3), all manifest themselves in human disease states as well as map to this region of the human genome. See the Online Mendellian Inheritance of Man (OMIM) gene map, and references therein, for this region of chromosome 16 on a publicly available WWW server. All of these serve as possible candidate genes for an inheritable disease which show linkage to the same chromosomal region as the zalpha11 gene.

Similarly, defects in the zalpha11 locus itself may result in a heritable human disease state. Molecules of the present invention, such as the polypeptides, antagonists, agonists, polynucleotides and antibodies of the present invention would aid in the detection, diagnosis prevention, and treatment associated with a zalpha11 genetic defect.

Mice engineered to express the zalpha11 gene, referred to as "transgenic mice," and mice that exhibit a complete absence of zalpha11 gene function, referred to as "knockout mice," may also be generated (Snouwaert et al., *Science* 257: 1083, 1992; Lowell et al., *Nature* 366:740-42, 1993; Capecchi, M. R., Science 244: 1288-1292, 1989; Palmiter, R. D. et al. *Annu Rev Genet.* 20: 465-499, 1986). For example, transgenic mice that over-express zalpha11, either ubiquitously or under a tissue-specific or tissue-restricted promoter can be used to ask whether over-expression causes a phenotype. For example, over-expression of a wild-type zalpha11 polypeptide, polypeptide fragment or a mutant thereof may alter normal cellular processes, resulting in a phenotype that identifies a tissue in which zalpha11 expression is functionally relevant and may indicate a therapeutic target for the zalpha11, its agonists or antagonists. For example, a preferred transgenic mouse to engineer is one that expresses a "dominant-negative" phenotype, such as one that over-expresses the zalpha11 extracellular cytokine binding domain with the transmembrane domain attached (approximately amino acids 20 (Cys) to 255 (Leu) of SEQ ID NO:2). Moreover, such over-expression may result in a phenotype that shows similarity with human diseases. Similarly, knockout zalpha11 mice can be used to determine where zalpha11 is absolutely required in vivo. The phenotype of knockout mice is predictive of the in vivo effects of that a zalpha11 antagonist, such as those described herein, may have. The mouse or the human zalpha11 cDNA can be used to isolate murine zalpha11 mRNA, cDNA and genomic DNA, which are subsequently used to generate knockout mice. These mice may be employed to study the zalpha11 gene and the protein encoded thereby in an in vivo system, and can be used as in vivo models for corresponding human diseases. Moreover, transgenic mice expression of zalpha11 antisense polynucleotides or ribozymes directed against zalpha11, described herein, can be used analogously to transgenic mice described above.

For pharmaceutical use, the soluble receptor polypeptides of the present invention are formulated for parenteral, particularly intravenous or subcutaneous, delivery according to conventional methods. Intravenous administration will be by bolus injection or infusion over a typical period of one to several hours. In general, pharmaceutical formulations will include a zalpha11 soluble receptor polypeptide in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in Remington: *The Science and Practice of Pharmacy*, Gennaro, ed., Mack Publishing Co., Easton, Pa., 19th ed., 1995. Therapeutic doses will generally be in the range of 0.1 to 100 μg/kg of patient weight per day, preferably 0.5-20 mg/kg per day, with the exact dose determined by the clinician according to accepted standards, taking into account the nature and severity of the condition to be treated, patient traits, etc. Determination of dose is within the level of ordinary skill in the art. The proteins may be administered for acute treatment, over one week or less, often over a period of one to three days or may be used in chronic treatment, over several months or years. In general, a therapeutically effective amount of zalpha11 soluble receptor polypeptide is an amount sufficient to produce a clinically significant effect.

The invention is further illustrated by the following non-limiting examples.

EXAMPLES

Example 1

Identification of Human Zalpha11

Using an EST Sequence to Obtain Full-length Zalpha11

Scanning of a translated DNA database resulted in identification of an expressed sequence tag (EST) sequence found to be a member of the Class I Cytokine Receptor family and designated zalpha11.

Confirmation of the EST sequence was made by sequence analyses of the cDNA from which the EST originated. This cDNA clone was obtained and sequenced using the following primers: ZC 447 (SEQ ID NO:5), ZC 976 (SEQ ID NO:6), ZC 19345 (SEQ ID NO:7), ZC 19346 (SEQ ID NO:8), ZC 19349 (SEQ ID NO:9), and ZC 19350 (SEQ ID NO:10), ZC 19458 (SEQ ID NO:11), ZC 19459 (SEQ ID NO:12), ZC 19460 (SEQ ID NO:13), ZC 19461 (SEQ ID NO:14), ZC 19572 (SEQ ID NO:15), ZC 19573 (SEQ ID NO:16), ZC 19657 (SEQ ID NO:17). The insert was 2945 bp, and was full-length.

Example 2

Tissue Distribution

Northern blot analysis was performed using human MULTIPLE TISSUE NORTHERN BLOTS™(MTN I, MTN II, and MTN III) (Clontech). The cDNA described in Example 1 was used in a PCR reaction using oligos ZC19,181 (SEQ ID NO:18) and ZC19,182 (SEQ ID NO:19) as primers. PCR conditions were as follows: 94° C. for 1.5 minutes; 35 cycles at 94° C. for 15 seconds then 68° C. for 30 seconds; 72° C. for 10 minutes; 4° C. overnight A sample of the PCR reaction product was run on a 1.5% agarose gel. A band of the expected size of 175 bp was seen. The 175 by PCR fragment, was gel purified using a commercially available kit (QIAEXII™; QIAGEN®) and then radioactively labeled with $^{32}$P-dCTP using REDIPRIME II™(Amersham), a random prime labeling system, according to the manufacturer's specifications. The probe was then purified using a NUC-TRAP™column (Stratagene) according to the manufacturer's instructions. EXPRESSHYB™(Clontech) solution was used for prehybridization and as a hybridizing solution for the Northern blots. Hybridization took place overnight at 65° C. using 1-2×$10^6$ cpm/ml of labeled probe. The blots were then washed 4 times for 15 minutes in 2×SSC/1% SDS at 25° C., followed by a wash in 0.1×SSC/0.1% SDS at 50° C. Transcripts of approximately 3 kb and 5 kb were detected in lymph node, peripheral blood leukocytes, and thymus.

Dot Blots were also performed using Human RNA Master Blots™ (Clontech). The methods and conditions for the Dot Blots are the same as for the Multiple Tissue Blots described above. Dot blot had strongest signals in thymus, lymph node, and spleen.

Northern analysis was also performed using Human Cancer Cell Line MTN™ (Clontech). The cDNA described in Example 1 was used in a PCR reaction using oligos ZC19,907 (SEQ ID NO:20) and ZC19,908 (SEQ ID NO:21) as primers. PCR conditions were as follows: 35 cycles at 95° C. for 1 minute, then 60° C. for 1 minute; 72° C. for 1.5 minutes; 72° C. for 10 minutes; 4° C. overnight A sample of the PCR reaction product was run on a 1.5% agarose gel. A band of the expected size of 1.2 kb was seen. The 1.2 kb PCR fragment, was gel purified using a commercially available kit (QIAQUICK™_Gel Extraction Kit; Qiagen) and then radioactively labeled with $^{32}$P-dCTP using Prime-It II™ (Stratagene), a random prime labeling system, according to the manufacturer's specifications. The probe was then purified using a NUC-TRAPT™ column (Stratagene) according to the manufacturer's instructions. EXPRESSHYB™ (Clontech) solution was used for prehybridization and as a hybridizing solution for the Northern blots. Hybridization took place for 2 hours at 65° C. using 1-2×$10^6$ cpm/ml of labeled probe. The blots were then washed 4 times for 15 minutes in 2×SSC/1% SDS at 25° C., followed by two 30 minute washes in 0.1×SSC/0.1% SDS at 50° C. A strong signal was seen in the Raji cell line derived from Burkitt's lymphoma.

Example 3

PCR-Based Chromosomal Mapping of the Zalpha11 Gene

Zalpha11 was mapped to chromosome 16 using the commercially available "GeneBridge 4 Radiation Hybrid Panel" (Research Genetics, Inc., Huntsville, Ala.). The GeneBridge 4 Radiation Hybrid Panel contains PCRable DNAs from each of 93 radiation hybrid clones, plus two control DNAs (the HFL donor and the A23 recipient). A publicly available WWW server allows mapping relative to the Whitehead Institute/MIT Center for Genome Research's radiation hybrid map of the human genome (the "WICGR" radiation hybrid map) which was constructed with the GeneBridge 4 Radiation Hybrid Panel.

For the mapping of Zalpha11 with the "GeneBridge 4 RH Panel," 20 μl reactions were set up in a 96-well microtiter plate (Stratagene, La Jolla, Calif.) and used in a "RoboCycler Gradient 96" thermal cycler (Stratagene). Each of the 95 PCR reactions consisted of 2 μl 10×PCR reaction buffer (Clontech Laboratories, Inc., Palo Alto, Calif.), 1.6 μl dNTPs mix (2.5 mM each, Perkin-Elmer, Foster City, Calif.), 1 μl sense primer, ZC 19,954, (SEQ ID NO:22), 1 μl antisense primer, ZC 19,955 (SEQ ID NO:23), 2 μl "RediLoad" (Research Genetics, Inc., Huntsville, Ala.), 0.4 μl 50× ADVANTAGE™ KlenTaq Polymerase Mix (Clontech), 25 ng of DNA from an individual hybrid clone or control and ddH2O for a total volume of 20 μl. The reactions were overlaid with an equal amount of mineral oil and sealed. The PCR cycler conditions were as follows: an initial 1 cycle 4 minute denaturation at 94° C.; 35 cycles of a 45 seconds at 94° C., 45 seconds at 68° C., and 1 minute at 72° C.; followed by 7 minutes at 72° C. The reactions were separated by electrophoresis on a 2% agarose gel (Life Technologies).

The results showed that zalpha11 maps 9.54 cR_3000 from the framework marker WI-3768 on the chromosome 16 WICGR radiation hybrid map. Proximal and distal framework markers were WI-3768 and TIGR-A002K05, respectively. The use of surrounding markers positions Zalpha11 in the 16p11.1 region on the integrated LDB chromosome 16 map (The Genetic Location Database, University of Southhampton.

Example 4

Construction of Human MPL-zalpha11 Polypeptide Chimera: MPL Extracellular and TM Domain Fused to the Zalpha11 Intracellular Signaling Domain The extracellular and transmembrane domains of the MPL receptor were isolated from a plasmid containing the MPL receptor (PHZ1/MPL plasmid) using PCR with primers ZC17,212 (SEQ ID NO:24) and ZC19,914 (SEQ ID NO:25). The reaction conditions were as follows: 95° C. for 1 min.; 35 cycles at 95° C. for 1 min., 45° C. for 1 min., 72° C. for 2 min.; followed by 72° C. at 10 min.; then a 10° C. soak. The PCR product was run on a 1% low melting point agarose (Boerhinger Mannheim, Indianapolis, Ind.) and the approximately 1.5 kb MPL receptor fragment isolated using QIAQUICK™ gel extraction kit (Qiagen) as per manufacturer's instructions.

The intracellular domains of zalpha11 were isolated from a plasmid containing zalpha11 receptor cDNA using PCR with primers ZC19,913 (SEQ ID NO:26) and ZC20,097 (SEQ ID NO:27). The polynucleotide sequence corresponding to the zalpha11 receptor coding sequence is shown in SEQ ID NO:1 from nucleotide 69 to 1682. The reaction conditions were as per above. The PCR product was run on a 1% low melting point agarose (Boerhinger Mannheim) and the approximately 900 bp zalpha11 fragment isolated using QIAQUICK™ gel extraction kit as per manufacturer's instructions.

Each of the isolated fragments described above were mixed at a 1:1 volumetric ratio and used in a PCR reaction using ZC17,212 (SEQ ID NO:24) and ZC20,097 (SEQ ID NO:27) to create the MPL-zalpha11 chimera. The reaction conditions were as follows: 95° C. for 1 min.; 35 cycles at 95° C. for 1 min., 55° C. for 1 min., 72° C. for 2 min.; followed by 72° C. at 10 min.; then a 10° C. soak. The entire PCR product was run on a 1% low melting point agarose (Boehringer Mannheim) and the approximately 2.4 kb MPL-zalpha11 chimera fragment isolated using QIAQUICK™ gel extraction kit (Qiagen) as per manufacturer's instructions. The MPL-zalpha11 chimera fragment was digested with EcoRI (BRL) and XbaI (Boerhinger Mannheim) as per manufacturer's instructions. The entire digest was run on a 1% low melting point agarose (Boehringer Mannheim) and the cleaved MPL-zalpha11 chimera isolated using QIAQUICK™ gel extraction kit (Qiagen) as per manufacturer's instructions. The resultant cleaved MPL-zalpha11 chimera was inserted into an expression vector as described below.

Recipient expression vector pZP-5N was digested with EcoRI (BRL) and HindIII (BRL) as per manufacturer's instructions, and gel purified as described above. This vector fragment was combined with the EcoRI and XbaI cleaved MPL-zalpha11 chimera isolated above and a XbaI/HindIII linker fragment in a ligation reaction. The ligation was run using T4 Ligase (BRL), at 15° C. overnight. A sample of the ligation was electroporated in to DH10B ELECTROMAX™_electrocompetent *E. coli* cells (25 μF, 200Ω, 2.3V). Transformants were plated on LB+Ampicillin plates and single colonies screened by PCR to check for the MPL-zalpha11 chimera using ZC17,212 (SEQ ID NO:24) and ZC20,097 (SEQ ID NO:27) using the PCR conditions as described above.

Confirmation of the MPL-zalpha11 chimera sequence was made by sequence analyses using the following primers: ZC12,700 (SEQ ID NO:28), ZC5,020 (SEQ ID NO:29), ZC6,675 (SEQ ID NO:30), ZC7,727 (SEQ ID NO:31), ZC8,290 (SEQ ID NO:32), ZC19,572 (SEQ ID NO:15), ZC6,622 (SEQ ID NO:33), ZC7,736 (SEQ ID NO:34), and ZC9,273 (SEQ ID NO:35). The insert was approximately 2.4 bp, and was full-length.

Example 5

MPL-zalpha11 Chimera Based Proliferation in BAF3 Assay Using ALAMAR BLUE™

A. Construction of BaF3 Cells Expressing MPL-zalpha11 Chimera

BaF3, an interleukin-3 (IL-3) dependent pre-lymphoid cell line derived from murine bone marrow (Palacios and Steinmetz, *Cell* 41: 727-734, 1985; Mathey-Prevot et al., *Mol. Cell. Biol.* 6: 4133-4135, 1986), was maintained in complete media (RPMI medium (JRH Bioscience Inc., Lenexa, Kans.) supplemented with 10% heat-inactivated fetal calf serum, 2 ng/ml murine IL-3 (mIL-3) (R & D, Minneapolis, Minn.), 2 mM L-GLUTAMAX™ media_(Gibco BRL), 1 mM Sodium Pyruvate (Gibco BRL), and PSN antibiotics (GIBCO BRL)). Prior to electroporation, pZP-5N/MPL-zalpha11 DNA (Example 4) was prepared and purified using a Qiagen Maxi Prep kit (Qiagen) as per manufacturer's instructions. BaF3 cells for electroporation were washed once in RPMI media and then resuspended in RPMI media at a cell density of $10^7$ cells/ml. One ml of resuspended BaF3 cells was mixed with 30 μg of the pZP-5N/MPL-zalpha11 plasmid DNA and transferred to separate disposable electroporation chambers (GIBCO BRL). Following a 15 minute incubation at room temperature the cells were given two serial shocks (800 lFad/300 V.; 1180 lFad/300 V.) delivered by an electroporation apparatus (CELL-PORATOR™; GIBCO BRL). After a 5 minute recovery time, the electroporated cells were transferred to 50 ml of complete media and placed in an incubator for 15-24 hours (37° C., 5% $CO_2$). The cells were then spun down and resuspended in 50 ml of complete media containing GENETICIN™ (Gibco) selection (500 μg/ml G418) in a T-162 flask to isolate the G418-resistant pool. Pools of the transfected BaF3 cells, hereinafter called BaF3/MPL-zalpha11 cells, were assayed for signaling capability as described below.

B. Testing Capability of the BaF3/MPL-zalpha11 Cells Using an ALAMAR BLUE™ Proliferation Assay BaF3/MPL-zalpha11 cells were spun down and washed in the complete media, described above, but without mIL-3

(hereinafter referred to as "mIL-3 free media"). The cells were spun and washed 3 times to ensure the removal of the mIL-3. Cells were then counted in a hemacytometer. Cells were plated in a 96-well format at 5000 cells per well in a volume of 100 μl per well using the mIL-3 free media.

Proliferation of the BaF3/MPL-zalpha11 cells was assessed using thrombopoietin (TPO) diluted with mIL-3 free media to 500 ng/ml, 250 ng/ml, 125 ng/ml, 62 ng/ml, 30 ng/ml, 15 ng/ml, 7.5 ng/ml, 3.75 ng/ml, 1.8 ng/ml, 0.9 ng/ml, 0.5 ng/ml and 0.25 ng/ml concentrations. 100 μl of the diluted TPO was added to the BaF3/MPL-zalpha11 cells. The total assay volume is 200 μl. Negative controls were run in parallel using mIL-3 free media only, without the addition of TPO. The assay plates were incubated at 37° C., 5% $CO_2$ for 3 days at which time ALAMAR BLUE™ (Accumed, Chicago, Ill.) was added at 20 μl/well. Alamar Blue gives a fluourometric readout based on number of live cells, and is thus a direct measurement of cell proliferation in comparison to a negative control. Plates were again incubated at 37° C., 5% $CO_2$ for 24 hours. Plates were read on the FMAX™ plate reader (Molecular Devices Sunnyvale, Calif.) using the SOFTMAX™ Pro program, at wavelengths 544 (Excitation) and 590 (Emission).

Results confirmed the signaling capability of the intracellular portion of the zalpha11 receptor as the thrombopoietin induced proliferation at approximately 10 fold over back ground at 62 ng/ml and greater.

Example 6

Construction of Expression Vector Expressing Full-length Zalpha11

The entire zalpha11 receptor was isolated from a plasmid containing zalpha11 receptor cDNA using PCR with primers ZC19,905 (SEQ ID NO:36) and ZC19,906 (SEQ ID NO:37). The reaction conditions were as follows: 95° C. for 1 min; 35 cycles at 95° C. for 1 min, 55° C. for 1 min, 72° C. for 2 min; followed by 72° C. at 10 min; then a 10° C. soak. The PCR product was run on a 1% low melting point agarose (Boerhinger Mannheim) and the approximately 1.5 kb zalpha11 cDNA isolated using QIAQUICK™ gel extraction kit (Qiagen) as per manufacturer's instructions.

The purified zalpha11 cDNA was digested with BamHI (Boerhinger Mannheim) and EcoRI (BRL) as per manufacturer's instructions. The entire digest was run on a 1% low melting point agarose (Boerhinger Mannheim) and purified the cleaved zalpha11 fragment using QIAQUICK™ gel extraction kit as per manufacturer's instructions. The resultant cleaved zalpha11 chimera was inserted into an expression vector as described below.

Recipient expression vector pZP-5N was digested with BamHI (Boerhinger Mannheim) and EcoRI (BRL) as per manufacturer's instructions, and gel purified as described above. This vector fragment was combined with the BamHI and EcoRI cleaved zalpha11 fragment isolated above in a ligation reaction. The ligation was run using T4 Ligase (BRL), at 15° C. overnight. A sample of the ligation was electroporated in to DH10B ELECTROMAX™ electrocompetent *E. coli* cells (25 μF, 200Ω, 2.3V). Transformants were plated on LB+Ampicillin plates and single colonies screened by PCR to check for the zalpha11 sequence using ZC19,905 (SEQ ID NO:36) and ZC19,906 (SEQ ID NO:37) using the PCR conditions as described above.

Confirmation of the MPL-zalpha11 sequence was made by sequence analyses using the following primers: ZC12,700 (SEQ ID NO:28), ZC5,020 (SEQ ID NO:29), ZC20,114 (SEQ ID NO:38), ZC19,459 (SEQ ID NO:12), ZC19,954 (SEQ ID NO:39), and ZC20,116 (SEQ ID NO:40). The insert was approximately 1.6 kb, and was full-length.

Example 7

Zalpha11 Based Proliferation in BAF3 Assay Using ALAMAR BLUE™

A. Construction of BaF3 Cells Expressing Zalpha11 Receptor

BaF3 cells expressing the full-length zalpha11 receptor were constructed as per Example 5A above, using 30 μg of the zalpha11 expression vector, described in Example 6 above. The BaF3 cells expressing the zalpha11 receptor mRNA were designated as BaF3/zalpha11. These cells were used to screen for a zalpha11 activity as described below in Examples 8 and 12.

Example 8

Screening for Zalpha11 Activity Using BaF3/Zalpha11 Cells Using an ALAMAR BLUE™ Proliferation Assay A. Monkey Primary Source Used to Test for Presence of Zalpha11 Activity Conditioned media from primary monkey spleen cells was used to test for the presence of activity as described below. Monkey spleen cells were activated with 5 ng/ml Phorbol-12-myristate-13-acetate (PMA) (Calbiochem, San Diego, Calif.), and 0.5 μg/ml IONOMYCIN™ ionophore (Calbiochem) for 72 h. The supernatant from the stimulated monkey spleen cells was used to assay proliferation of the BaF3/zalpha11 cells as described below.

B. Screening for Zalpha11 Activity Using BaF3/Zalpha11 Cells Using an ALAMAR BLUE™ Proliferation Assay BaF3/Zalpha11 cells were spun down and washed in mIL-3 free media. The cells were spun and washed 3 times to ensure the removal of the mIL-3 Cells were then counted in a hemacytometer. Cells were plated in a 96-well format at 5000 cells per well in a volume of 100 μl per well using the mIL-3 free media.

Proliferation of the BaF3/Zalpha11 cells was assessed using conditioned media from activated monkey spleen (see Example 8A, above) was diluted with mIL-3 free media to 50%, 25%, 12.5%, 6.25%, 3.125%, 1.5%, 0.75% and 0.375% concentrations. 100 μl of the diluted conditioned media was added to the BaF3/Zalpha11 cells. The total assay volume is 200 μl. The assay plates were incubated at 37° C., 5% $CO_2$ for 3 days at which time ALAMAR BLUE™ dye (Accumed, Chicago, Ill.) was added at 20 μl/well. Plates were again incubated at 37° C., 5% $CO_2$ for 24 hours. Plates were read on the FMAX™ plate reader (Molecular devices) as described above (Example 5).

Results confirmed the proliferative response of the BaF3/Zalpha11 cells to a factor present in the activate monkey spleen conditioned media. The response, as measured, was approximately 4-fold over background at the 50% concentration. The BaF3 wild type cells did not proliferate in response to this factor, showing that this factor is specific for the Zalpha11 receptor.

C. Human Primary Source Used to Isolate Zalpha11 Activity 100 ml blood draws were taken from each of six donors. The blood was drawn using 10×10 ml vacutainer tubes containing heparin. Blood was pooled from six donors (600 ml), diluted 1:1 in PBS, and separated using a FICOLL-PAQUE®

PLUS solution (Pharmacia Biotech, Uppsala, Sweden). The isolated primary human cell yield after separation on the ficoll gradient was $1.2\times10^9$ cells.

Cells were suspended in 9.6 ml MACS buffer (PBS, 0.5% EDTA, 2 mM EDTA). 1.6 ml of cell suspension was removed and 0.4 ml CD3 microbeads (Miltenyi Biotec, Auburn, Calif.) added. The mixture was incubated for 15 min. at 4° C. These cells labeled with CD3 beads were washed with 30 ml MACS buffer, and then resuspended in 2 ml MACS buffer.

A VS+ column (Miltenyi) was prepared according to the manufacturer's instructions. The VS+ column was then placed in a VARIOMACS™ magnetic field (Miltenyi). The column was equilibrated with 5 ml MACS buffer. The isolated primary human cells were then applied to the column. The CD3 negative cells were allowed to pass through. The column was rinsed with 9 ml (3×3 ml) MACS buffer. The column was then removed from the magnet and placed over a 15 ml falcon tube. CD3+ cells were eluted by adding 5 ml MACS buffer to the column and bound cells flushed out using the plunger provided by the manufacturer. The incubation of the cells with the CD3 magnetic beads, washes, and VS+ column steps (incubation through elution) above were repeated five more times. The resulting CD3+ fractions from the six column separations were pooled. The yield of CD3+ selected human T-cells were $3\times10^8$ total cells.

A sample of the pooled CD3+ selected human T-cells was removed for staining and sorting on a fluorescent antibody cell sorter (FACS) to assess their purity. The CD3+ selected human T-cells were 91% CD3+ cells.

The CD3+ selected human T-cells were activated by incubating in RPMI+5% FBS+PMA 10 ng/ml and Ionomycin 0.5 μg/ml (Calbiochem) for 13 hours 37° C. The supernatant from these activated CD3+ selected human T-cells was tested for zalpha11 activity as described below.

D. Testing Supernatant from Activated Cd3+ Selected Human T-cells for Zalpha11 Activity Using BaF3/Zalpha11 Cells and an ALAMAR BLUE™ Proliferation Assay BaF3/Zalpha11 cells were spun down and washed in mIL-3 free media. The cells were spun and washed 3 times to ensure the removal of the mIL-3 Cells were then counted in a hemacytometer. Cells were plated in a 96-well format at 5000 cells per well in a volume of 100 μl per well using the mIL-3 free media.

Proliferation of the BaF3/Zalpha11 cells was assessed using conditioned media from activated CD3+ selected human T-cells (see Example 8C, above) diluted with mIL-3 free media to 50%, 25%, 12.5%, 6.25%, 3.125%, 1.5%, 0.75% and 0.375% concentrations. 100 μl of the diluted conditioned media was added to the BaF3/Zalpha11 cells. The total assay volume is 200 μl. The assay plates were incubated and assayed as described in Example 8B above.

Results confirmed the proliferative response of the BaF3/Zalpha11 cells to a factor present in the activated CD3+ selected human T-cell conditioned media. The response, as measured, was approximately 10-fold over background at the 50% concentration. The BaF3 wild type cells did not proliferate in response to this factor, showing that this factor is specific for the Zalpha11 receptor.

Example 9

Construction of Mammalian Expression Vectors Tthat Express Zalpha11 Soluble Receptors: Zalpha11CEE, zalpha11CFLG, Zalpha11CHIS and Zalph11-Fc4

A. Construction of Zalpha11 Mammalian Expression Vector Containing Zalph11CEE, Zalph11CFLG and Zalph11CHIS An expression vector was prepared for the expression of the soluble, extracellular domain of the zalpha11 polypeptide, pC4zalph11CEE, wherein the construct is designed to express a zalpha11 polypeptide comprised of the predicted initiating methionine and truncated adjacent to the predicted transmembrane domain, and with a C-terminal Glu-Glu tag (SEQ ID NO:41).

A 700 bp PCR generated zalpha11 DNA fragment was created using ZC19,931 (SEQ ID NO:42) and ZC19,932 (SEQ ID NO:43) as PCR primers to add Asp718 and BamHI restriction sites. A plasmid containing the zalpha11 receptor cDNA was used as a template. PCR amplification of the zalpha11 fragment was performed as follows: Twenty five cycles at 94 C for 0.5 minutes; five cycles at 94° C. for 10 seconds, 50° C. for 30 seconds, 68° C. for 45 seconds, followed by a 4° C. hold. The reaction was purified by chloroform/phenol extraction and isopropanol precipitation, and digested with Asp718 and BamHI (Gibco BRL) following manufacturer's protocol. A band of the predicted size, 700 bp, was visualized by 1% agarose gel electrophoresis, excised and the DNA was purified using a QIAEXII™ purification system (Qiagen) according the manufacturer's instructions.

The excised DNA was subcloned into plasmid pC4EE which had been cut with BamHI and Asp718. The pC4zalphl10EE expression vector uses the native zalpha11 signal peptide and attaches the Glu-Glu tag (SEQ ID NO:41) to the C-terminus of the zalpha11 polypeptide-encoding polynucleotide sequence. Plasmid pC4EE, is a mammalian expression vector containing an expression cassette having the mouse metallothionein-1 promoter, multiple restriction sites for insertion of coding sequences, a stop codon and a human growth hormone terminator. The plasmid also has an *E. coli* origin of replication, a mammalian selectable marker expression unit having an SV40 promoter, enhancer and origin of replication, a DHFR gene and the SV40 terminator.

About 30 ng of the restriction digested zalpha11 insert and about 12 ng of the digested vector were ligated overnight at 16° C. One microliter of each ligation reaction was independently electroporated into DH10B competent cells (GIBCO BRL, Gaithersburg, Md.) according to manufacturer's direction and plated onto LB plates containing 50 mg/ml ampicillin, and incubated overnight. Colonies were screened by restriction analysis of DNA prepared from 2 ml liquid cultures of individual colonies. The insert sequence of positive clones was verified by sequence analysis. A large scale plasmid preparation was done using a QIAGEN® Maxi prep kit (Qiagen) according to manufacturer's instructions.

The same process was used to prepare the zalpha11 soluble receptors with a C-terminal his tag, composed of 6 His residues in a row; and a C-terminal flag (SEQ ID NO:49) tag, zalpha11CFLAG. To construct these constructs, the aforementioned vector has either the HIS or the FLAG® tag in place of the glu-glu tag (SEQ ID NO:41).

B. Mammalian Expression Construction of Soluble Zalpha11 Receptor Zalpha11-Fc4

An expression plasmid containing all or part of a polynucleotide encoding zalpha11 was constructed via homologous recombination. A fragment of zalpha11 cDNA was isolated using PCR that includes the polynucleotide sequence from extracellular domain of the zalhal 1 receptor. The two primers used in the production of the zalpha11 fragment were: (1) The primers for PCR each include from 5' to 3' end: 40 bp of the vector flanking sequence (5' of the insert) and 17 bp corresponding to the 5' end of the zalpha11 extracellular domain (SEQ ID NO:44); and (2) 40 bp of the 5' end of the Fc4 polynucleotide sequence (SEQ ID NO:45) and 17 bp corresponding to the 3' end of the zalpha11 extracellular domain (SEQ ID NO:46). The fragment of Fc-4 for fusion with the zalpha11 was generated by PCR in a similar fashion. The two primers used in the production of the Fc4 fragment were: (1) a 5' primer consisting of 40 bp of sequence from the 3' end of zalpha11 extracellular domain and 17 bp of the 5' end of Fc4 (SEQ ID NO:47); and (2) a 3' primer consisting of 40 bp of vector sequence (3' of the insert) and 17 bp of the 3' end of Fc4 (SEQ ID NO:48).

PCR amplification of the each of the reactions described above was performed as follows: one cycle at 94° C. for 2 minutes; twenty-five cycles at 94° C. for 30 seconds, 60° C. for 30 seconds, 72° C. for 1 minute; one cycle at 72° C. for 5 minutes; followed by a 4° C. hold. Ten µl of the 100 µl PCR reaction was run on a 0.8% LMP agarose gel (Seaplaque GTG) with 1×TBE buffer for analysis. The remaining 90 µl of PCR reaction is precipitated with the addition of 5 µl 1 M NaCl and 250 µl of absolute ethanol. The expression vector used was derived from the plasmid pCZR199 (deposited at the American Type Culture Collection, 10801 University Boulevard, Manassas, Va. 20110-2209, and is designated No. 98668), and was cut with SmaI (BRL). The expression vector was derived from the plasmid pCZR199, and is a mammalian expression vector containing an expression cassette having the CMV immediate early promoter, a consensus intron from the variable region of mouse immunoglobulin heavy chain locus, multiple restriction sites for insertion of coding sequences, a stop codon and a human growth hormone terminator. The expression vector also has an *E. coli* origin of replication, a mammalian selectable marker expression unit having an SV40 promoter, enhancer and origin of replication, a DHFR gene and the SV40 terminator. The expression vector used was constructed from pCZR199 by the replacement of the metallothionein promoter with the CMV immediate early promoter.

One hundred microliters of competent yeast cells (*S. cerevisiae*) were combined with 10 µl containing approximately 1 µg each of the zalpha11 and Fc4 inserts, and 100 ng of SmaI (BRL) digested expression vector and transferred to a 0.2 cm electroporation cuvette. The yeast/DNA mixtures were electropulsed at 0.75 kV (5 kV/cm), "infinite" ohms, 25 µF. To each cuvette is added 600 µl of 1.2 M sorbitol and the yeast was plated in two 300 µl aliquots onto two URA-D plates and incubated at 30° C.

After about 48 hours, the Ura+ yeast transformants from a single plate were resuspended in 1 ml $H_2O$ and spun briefly to pellet the yeast cells. The cell pellet was resuspended in 1 ml of lysis buffer (2% Triton X-100, 1% SDS, 100 mM NaCl, 10 mM Tris, pH 8.0, 1 mM EDTA). Five hundred microliters of the lysis mixture was added to an Eppendorf tube containing 300 µl acid washed glass beads and 200 µl phenol-chloroform, vortexed for 1 minute intervals two or three times, followed by a 5 minute spin in a Eppendorf centrifuge at maximum speed. Three hundred microliters of the aqueous phase was transferred to a fresh tube, and the DNA precipitated with 600 µl ethanol (EtOH), followed by centrifugation for 10 minutes at 4° C. The DNA pellet was resuspended in 100 µl $H_2O$.

Transformation of electrocompetent *E. coli* cells (DH10B, GibcoBRL) is done with 0.5-2 ml yeast DNA prep and 40 ul of DH10B cells. The cells were electropulsed at 2.0 kV, 25 mF and 400 ohms. Following electroporation, 1 ml SOC (2% Bactoe Tryptone (Difco, Detroit, Mich.), 0.5% yeast extract (Difco), 10 mM NaCl, 2.5 mM KCl, 10 mM $MgCl_2$, 10 mM MgSO4, 20 mM glucose) was plated in 250 µl aliquots on four LB AMP plates (LB broth (Lennox), 1.8% Bacto Agar (Difco), 100 mg/L Ampicillin).

Individual clones harboring the correct expression construct for zalpha11-Fc4 were identified by restriction digest to verify the presence of the zalpha11-Fc4 insert and to confirm that the various DNA sequences have been joined correctly to one another. The insert of positive clones were subjected to sequence analysis. Larger scale plasmid DNA is isolated using the Qiagen Maxi kit (Qiagen) according to manufacturer's instructions.

Example 10

Transfection and Expression of Zalpha11 Soluble Receptor Polypeptides

BHK 570 cells (ATCC No. CRL-10314), passage 27, were plated at $1.2\times10^6$ cells/well (6-well plate) in 800 µl of serum free (SF) DMEM media (DMEM, Gibco/BRL High Glucose) (Gibco BRL, Gaithersburg, Md.). The cells were transfected with expression plasmids containing zalpha11CEE/CFLG/CHIS described above (see, Example 9), using LIPOFECTIN™ reagent (Gibco BRL), in serum free (SF) DMEM. Three micrograms of zalpha11CEE/CFLG/CHIS each were separately diluted into 1.5 ml tubes to a total final volume of 100 µl SF DMEM. In separate tubes, 15 µl of LIPOFECTIN™ reagent (Gibco BRL) was mixed with 100 µl of SF DMEM. The LIPOFECTIN™ reagent mix was incubated at room temperature for 30-45 minutes then the DNA mix was added and allowed to incubate approximately 10-15 minutes at room temperature.

The entire DNA:LIPOFECTINT™ reagent mixture was added to the plated cells and distributed evenly over them. The cells were incubated at 37° C. for approximately five hours, then transferred to separate 150 mm MAXI plates in a final volume of 30 ml DMEM/5% fetal bovine serum (FBS) (Hyclone, Logan, Utah). The plates were incubated at 37° C., 5% $CO_2$, overnight and the DNA:LIPOFECTIN™ reagent mixture was replaced with selection media (5% FBS/DMEM with 1 µM methotrexate (MTX)) the next day.

Approximately 10-12 days post-transfection, the plates were washed with 10 ml SF DMEM. The wash media was aspirated and replaced with 7.25 ml serum-free DMEM. Sterile Teflon meshes (Spectrum Medical Industries, Los Angeles, Calif.) pre-soaked in SF DMEM were then placed over the clonal cell colonies. A sterile nitrocellulose filter pre-soaked in SF DMEM was then placed over the mesh. Orientation marks on the nitrocellulose were transferred to the culture dish. The plates were then incubated for 5-6 hours in a 37° C., 5% $CO_2$ incubator.

Following incubation, the filters/meshes were removed, and the media aspirated and replaced with 5% FBS/DMEM with 1 µM MTX. The filters were then blocked in 10% nonfat dry milk/Western A buffer (Western A: 50 mM Tris pH 7.4, 5 mM EDTA, 0.05% NP-40, 150 mM NaCl and 0.25% gelatin) for 15 minutes at room temperature on a rotating shaker. The filters were then incubated with an anti-Glu-Glu, anti-FLAG®, or anti-HIS antibody-HRP conjugates, respectively, in 2.5% nonfat dry milk/Western A buffer for one hour at room temperature on a rotating shaker. The filters were then washed three times at room temperature with Western A for 5-10 minutes per wash. The filters were developed with ultra ECL reagent (Amersham Corp., Arlington Heights, Ill.) according the manufacturer's directions and visualized on the Lumi-Imager (Roche Corp.)

Positive expressing clonal colonies were mechanically picked to 12-well plates in one ml of 5% FCS/DMEM with 5 µM MTX, then grown to confluence. Conditioned media samples were then tested for expression levels via SDS- PAGE and Western anlaysis. The three highest expressing clones for each construct were picked; two out of three were frozen down as back up and one was expanded for mycoplasma testing and large-scale factory seeding.

B. Mammalian Expression of Soluble Zalpha11 Receptor Zalpha11-Fc4

BHK 570 cells (ATCC NO: CRL-10314) were plated in 10 cm tissue culture dishes and allowed to grow to approximately 50 to 70% confluency overnight at 37° C., 5% $CO_2$, in DMEM/FBS media (DMEM, Gibco/BRL High Glucose, (Gibco BRL, Gaithersburg, Md.), 5% fetal bovine serum (Hyclone, Logan, Utah), 1 mM L-glutamine (JRH Biosciences, Lenexa, Kans.), 1 mM sodium pyruvate (Gibco BRL)). The cells were then transfected with the plasmid containing zalpha11-Fc4 (see, Example 9), using LIPOFECTAMINE™ (Gibco BRL), in serum free (SF) media formulation (DMEM, 10 mg/ml transferrin, 5 mg/ml insulin, 2 mg/ml fetuin, 1% L-glutamine and 1% sodium pyruvate). The plasmid containing zalpha11-Fc4 was diluted into 15 ml tubes to a total final volume of 640 ml with SF media. 35 ml of LIPOFECTAMINE™ (Gibco BRL) was mixed with 605 ml of SF medium. The LIPOFECTAMINE™ mix was added to the DNA mix and allowed to incubate approximately 30 minutes at room temperature. Five milliliters of SF media was added to the DNA:LIPOFECTAMINE™ mixture. The cells were rinsed once with 5 ml of SF media, aspirated, and the DNA:LIPOFECTAMINE™ mixture is added. The cells were incubated at 37° C. for five hours, then 6.4 ml of DMEM/10% FBS, 1% PSN media was added to each plate. The plates were incubated at 37° C. overnight and the DNA:LIPOFECTAMINE™ mixture was replaced with fresh 5% FBS/DMEM media the next day. On day 2 post-transfection, the cells were split into the selection media (DMEM/FBS media from above with the addition of 1 mM methotrexate (Sigma Chemical Co., St. Louis, Mo.)) in 150 mm plates at 1:10, 1:20 and 1:50. The media on the cells was replaced with fresh selection media at day 5 post-transfection. Approximately 10 days post-transfection, two 150 mm culture dishes of methotrexate resistant colonies from each transfection were trypsinized and the cells are pooled and plated into a T-162 flask and transferred to large scale culture.

Example 11

Purification of Zalpha11 Soluble Receptors From BHK 570 Cells

A. Purification of Zalpha11CEE Polypeptide from BHK 570

Unless otherwise noted, all operations were carried out at 4° C. The following procedure was used for purifying zalpha11 polypeptide containing C-terminal GluGlu (EE) tags. Thirty liters of cell factory conditioned media was concentrated to 1.6 liters with an Amicon S10Y3 spiral cartridge on a ProFlux A30. A Protease inhibitor solution was added to the concentrated 1.6 liters of cell factory conditioned media from transfected BHK 570 cells (see, Example 10) to final concentrations of 2.5 mM ethylenediaminetetraacetic acid (EDTA, Sigma Chemical Co. St. Louis, Mo.), 0.003 mM leupeptin (Boehringer-Mannheim, Indianapolis, Ind.), 0.001 mM pepstatin (Boehringer-Mannheim) and 0.4 mM Pefabloc (Boehringer-Mannheim). Samples were removed for analysis and the bulk volume was frozen at −80° C. until the purification was started. Total target protein concentrations of the concentrated cell factory conditioned media was determined via SDS-PAGE and Western blot analysis with the anti-EE HRP conjugated antibody.

A 100 ml column of anti-EE G-Sepharose (prepared as described below) was poured in a Waters AP-5, 5 cm×10 cm glass column. The column was flow packed and equilibrated on a BioCad Sprint (PerSeptive BioSystems, Framingham, Mass.) with phosphate buffered saline (PBS) pH 7.4. The concentrated cell factory conditioned media was thawed, 0.2 micron sterile filtered, pH adjusted to 7.4, then loaded on the column overnight with 1 ml/minute flow rate. The column was washed with 10 column volumes (CVs) of phosphate buffered saline (PBS, pH 7.4), then plug eluted with 200 ml of PBS (pH 6.0) containing 0.5 mg/ml EE peptide (Anaspec, San Jose, Calif.) at 5 ml/minute. The EE peptide used has the sequence EYMPME (SEQ ID NO:41). The column was washed for 10 CVs with PBS, then eluted with 5 CVs of 0.2M glycine, pH 3.0. The pH of the glycine-eluted column was adjusted to 7.0 with 2 CVs of 5×PBS, then equilibrated in PBS (pH 7.4). Five ml fractions were collected over the entire elution chromatography and absorbance at 280 and 215 nM were monitored; the pass through and wash pools were also saved and analyzed. The EE-polypeptide elution peak fractions were analyzed for the target protein via SDS-PAGE Silver staining and Western Blotting with the anti-EE HRP conjugated antibody. The polypeptide elution fractions of interest were pooled and concentrated from 60 ml to 5.0 ml using a 10,000 Dalton molecular weight cutoff membrane spin concentrator (Millipore, Bedford, Mass.) according to the manufacturer's instructions.

To separate zalpha11CEE from other co-purifying proteins, the concentrated polypeptide elution pooled fractions were subjected to a POROS HQ-50 (strong anion exchange resin from PerSeptive BioSystems, Framingham, Mass.) at pH 8.0. A 1.0×6.0 cm column was poured and flow packed on a BioCad Sprint. The column was counter ion charged then equibrated in 20 mM TRIS pH 8.0 (Tris (Hydroxymethyl Aminomethane)). The sample was diluted 1:13 (to reduce the ionic strength of PBS) then loaded on the Poros HQ column at 5 ml/minute. The column was washed for 10 CVs with 20 mM Tris pH 8.0 then eluted with a 40 CV gradient of 20 mM Tris/1 M sodium chloride (NaCl) at 10 ml/minute. 1.5 ml fractions were collected over the entire chromatography and absorbance at 280 and 215 nM were monitored. The elution peak fractions were analyzed via SDS-PAGE Silver staining. Fractions of interest were pooled and concentrated to 1.5-2 ml using a 10,000 Dalton molecular weight cutoff membrane spin concentrator (Millipore, Bedford, Mass.) according to the manufacturer's instructions.

To separate zalpha11CEE polypeptide from free EE peptide and any contaminating co-purifying proteins, the pooled concentrated fractions were subjected to chromatography on a 1.5×90 cm Sephadex S200 (Pharmacia, Piscataway, N.J.) column equilibrated and loaded in PBS at a flow rate of 1.0 ml/min using a BioCad Sprint. 1.5 ml fractions were collected across the entire chromatography and the absorbance at 280 and 215 nM were monitored. The peak fractions were characterized via SDS-PAGE Silver staining, and only the most pure fractions were pooled. This material represented purified zalpha11CEE polypeptide.

This purified material was finally sujectd to a 4 ml ActiClean Etox (Sterogene) column to remove any remaining endotoxins. The sample was passed over the PBS equilibrated gravity column four times then the column was washed with a single 3 ml volume of PBS, which was pooled with the "cleaned" sample. The material was then 0.2 micron sterile filtered and stored at −80° C. until it was aliquoted.

On Western blotted, Coomassie Blue and Silver stained SDS-PAGE gels, the zalpha11CEE polypeptide was one major band of an apparent molecular weight of 50,000 Daltons. The mobility of this band was the same on reducing and non-reducing gels.

The protein concentration of the purified material was performed by BCA analysis (Pierce, Rockford, Ill.) and the protein was aliquoted, and stored at −80° C. according to our standard procedures. On IEF (isoelectric focusing) gels the protein runs with a PI of less than 4.5. The concentration of zalpha11CEE polypeptide was 1.0 mg/ml.

Purified zalpha11CEE polypeptide was prepared for injection into rabbits and sent to R & R Research and Development (Stanwood, Wash.) for antibody production. Rabbits were injected to produce anti-huzalpha11-CEE-BHK serum (Example 15, below).

To prepare anti-EE Sepharose, a 100 ml bed volume of protein G-Sepharose (Pharmacia, Piscataway, N.J.) was washed 3 times with 100 ml of PBS containing 0.02% sodium azide using a 500 ml Nalgene 0.45 micron filter unit. The gel was washed with 6.0 volumes of 200 mM triethanolamine, pH 8.2 (TEA, Sigma, St. Louis, Mo.), and an equal volume of EE antibody solution containing 900 mg of antibody was added. After an overnight incubation at 4° C., unbound antibody was removed by washing the resin with 5 volumes of 200 mM TEA as described above. The resin was resuspended in 2 volumes of TEA, transferred to a suitable container, and dimethylpimilimidate-2HCl (Pierce, Rockford, Ill.) dissolved in TEA, was added to a final concentration of 36 mg/ml of protein G-Sepharose gel. The gel was rocked at room temperature for 45 min and the liquid was removed using the filter unit as described above. Nonspecific sites on the gel were then blocked by incubating for 10 min. at room temperature with 5 volumes of 20 mM ethanolamine in 200 mM TEA. The gel was then washed with 5 volumes of PBS containing 0.02% sodium azide and stored in this solution at 4° C.

B. Purification of Zalpha11CFLAG Polypeptide from BHK 570

Unless otherwise noted, all operations were carried out at 4° C. The following procedure was used for purifying zalpha11 polypeptide containing C-terminal FLAG® (FLG) (Sigma-Aldrich Co.) tags. Thirty liters of cell factory conditioned media was concentrated to 1.7 liters with an Amicon 510Y3 spiral catridge on a ProFlux A30. A Protease inhibitor solution was added to the 1.7 liters of concentrated cell factory conditioned media from transfected BHK 570 cells (see, Example 10) to final concentrations of 2.5 mM ethylenediaminetetraacetic acid (EDTA, Sigma Chemical Co. St. Louis, Mo.), 0.003 mM leupeptin (Boehringer-Mannheim, Indianapolis, Ind.), 0.001 mM pepstatin (Boehringer-Mannheim) and 0.4 mM Pefabloc (Boehringer-Mannheim). Samples were removed for analysis and the bulk volume was frozen at −80° C. until the purification was started. Total target protein concentrations of the cell factory conditioned media was determined via SDS-PAGE and Western blot analysis with the anti-FLAG® (Kodak) HRP conjugated antibody. A 125 ml column of anti-FLAG® M2-Agarose affinity gel (Sigma-Aldrich Co.) was poured in a Waters AP-5, 5 cm×10 cm glass column. The column was flow packed and equilibrated on a BioCad Sprint (PerSeptive BioSystems, Framingham, Mass.) with phosphate buffered saline (PBS) pH 7.4. The concentrated cell factory conditioned media was thawed, 0.2 micron sterile filtered, pH adjusted to 7.4, then loaded on the column overnight with 1 ml/minute flow rate. The column was washed with 10 column volumes (CVs) of phosphate buffered saline (PBS, pH 7.4), then plug eluted with 250 ml of PBS (pH 6.0) containing 0.5 mg/ml FLAG® (Sigma-Aldrich Co.) peptide at 5 ml/minute. The FLAG® peptide used has the sequence DYKDDDDK (SEQ ID NO:49). The column was washed for 10 CVs with PBS, then eluted with 5 CVs of 0.2M glycine, pH 3.0. The pH of the glycine-eluted column was adjusted to 7.0 with 2 CVs of 5×PBS, then equilibrated in PBS (pH 7.4). Five ml fractions were collected over the entire elution chromatography and absorbence at 280 and 215 nM were monitored; the pass through and wash pools were also saved and analyzed. The FLAG®-polypeptide elution peak fractions were analyzed for the target protein via SDS-PAGE Silver staining and Western Blotting with the anti-FLAG HRP conjugated antibody. The polypeptide elution fractions of interest were pooled and concentrated from 80 ml to 12 ml using a 10,000 Dalton molecular weight cutoff membrane spin concentrator (Millipore, Bedford, Mass.) according to the manufacturer's instructions.

To separate zalpha11CFLG from other co-purifying proteins, the polypeptide elution pooled fractions were subjected to a POROS HQ-50 (strong anion exchange resin from PerSeptive BioSystems, Framingham, Mass.) at pH 8.0. A 1.0×6.0 cm column was poured and flow packed on a BioCad Sprint. The column was counter ion charged then equilibrated in 20 mM TRIS pH 8.0 (Tris (Hydroxymethyl Aminomethane)). The sample was diluted 1:13 (to reduce the ionic strength of PBS) then loaded on the Poros HQ-50 column at 5 ml/minute. The column was washed for 10 column volumes (CVs) with 20 mM Tris pH 8.0 then eluted with a 40 CV gradient of 20 mM Tris/1 M sodium chloride (NaCl) at 10 ml/minute. 1.5 ml fractions were collected over the entire chromatography and absorbance at 280 and 215 nM were monitored. The elution peak fractions were analyzed via SDS-PAGE Silver staining. Fractions of interest were pooled and concentrated to 1.5-2 ml using a 10,000 Dalton molecular weight cutoff membrane spin concentrator (Millipore, Bedford, Mass.) according to the manufacturer's instructions.

To separate zalpha11CFLG polypeptide from free FLAG® peptide and any contaminating co-purifying proteins, the pooled concentrated fractions were subjected to chromatography on a 1.5×90 cm Sephacryl S200 (Pharmacia, Piscataway, N.J.) column equilibrated and loaded in PBS at a flow rate of 1.0 ml/min using a BioCad Sprint. 1.5 ml fractions were collected across the entire chromatography and the absorbance at 280 and 215 nM were monitored. The peak fractions were characterized via SDS-PAGE Silver staining, and only the most pure fractions were pooled. This material represented purified zalpha11CFLG polypeptide.

This purified material was finally sujectd to a 4 ml ActiClean Etox (Sterogene) column to remove any remaining endotoxins. The sample was passed over the PBS equilibrated gravity column four times then the column was washed with a single 3 ml volume of PBS, which was pooled with the "cleaned" sample. The material was then 0.2 micron sterile filtered and stored at −80° C. until it was aliquoted.

On Western blotted, Coomassie Blue and Silver stained SDS-PAGE gels, the zalpha11CFLG polypeptide was one major band of an apparent molecular weight of 50,000 Daltons. The mobility of this band was the same on reducing and non-reducing gels.

The protein concentration of the purified material was performed by BCA analysis (Pierce, Rockford, Ill.) and the protein was aliquoted, and stored at −80° C. according to our standard procedures. On IEF (isoelectric focusing) gels the protein runs with a PI of less than 4.5. The concentration of zalpha11CFLG polypeptide was 1.2 mg/ml.

C. Purification of Zalpha11-Fc4 Polypeptide from Transfected BHK 570 Cells

Unless otherwise noted, all operations were carried out at 4° C. The following procedure was used for purifying zalpha11 polypeptide containing C-terminal fusion to human IgG/Fc (zalpha11-Fc4; Examples 8 and 9). 12,000 ml of conditioned media from BHK 570 cells transfected with zalpha11-Fc4 (Example 10) was filtered through a 0.2 mm sterilizing filter and then supplemented with a solution of protease inhibitors, to final concentrations of, 0.001 mM leupeptin (Boerhinger-Mannheim, Indianapolis, Ind.), 0.001 mM pepstatin (Boerhinger-Mannheim) and 0.4 mM Pefabloc (Boerhinger-Mannheim). A protein G sepharose (6 ml bed volume, Pharmacia Biotech) was packed and washed with 500 ml PBS (Gibco/BRL) The supplemented conditioned media was passed over the column with a flow rate of 10 ml/minute, followed by washing with 1000 ml PBS (BRL/Gibco). zalpha11-Fc4 was eluted from the column with 0.1 M Glycine pH 3.5 and 2 ml fractions were collected directly into 0.2 ml 2M Tris pH 8.0, to adjust the final pH to 7.0 in the fractions.

The eluted fractions were characterized by SDS-PAGE and western blotting with anti-human Fc (Amersham) antibodies. Western blot analysis of reducing SDS-PAGE gels reveal an immunoreactive protein of 80,000 KDa in fractions 2-10. Silver stained SDS-PAGE gels also revealed an 80,000 KDa zalpa11:Fc polypeptide in fractions 2-10. Fractions 2-10 were pooled.

The protein concentration of the pooled fractions was performed by BCA analysis (Pierce, Rockford, Ill.) and the material was aliquoted, and stored at −80° C. according to our standard procedures. The concentration of the pooled fractions was 0.26 mg/ml.

Example 12

Assay Using Zalpha11 Soluble Receptor Zalpha11CEE, Zalpha11CFLG and Zalpha11-Fc4 (Mutant) Soluble Receptors in Competitive Inhibition Assay BaF3/Zalpha11 cells were spun down and washed in mIL-3 free media. The cells were spun and washed 3 times to ensure the removal of the mIL-3 Cells were then counted in a hemacytometer. Cells were plated in a 96-well format at 5000 cells per well in a volume of 100 μl per well using the mIL-3 free media.

Both media from the monkey spleen cell activation and the CD3+ selected cells, described in Example 8 above, were added in separate experiments at 50%, 25%, 12.5%, 6.25%, 3.125%, 1.5%, 0.75% and 0.375% concentrations, with or without zalpha11 soluble receptors (CEE, C-flag, and Fc4 constructs; See, Example 10 and 11) at 10 μg/ml. The total assay volume was 200 μl.

The assay plates were incubated 37° C., 5% $CO_2$ for 3 days at which time Alamar Blue (Accumed) was added at 20 μl/well. Plates were again incubated at 37° C., 5% $CO_2$ for 24 hours. Plates were read on the Fmax™ plate reader (Molecular Devices) as described above (Example 5). Results demonstrated complete inhibition of cell growth from each of the different zalpha11 soluble receptor constructs at 10 μg/ml, confirming that the factor in each sample was specific for the zalpha11 receptor.

Titration curves, diluting out the soluble receptors, were also run using the above stated assay. Both the zalpha11CEE and zalpha11CFLG soluble zalpha11 receptors were able to completely inhibit growth as low as 20 ng/ml. The mutant zalpha11-Fc4 soluble zalpha11 receptor was only as effective at 1.5 μg/ml.

Example 13

Expression of Human Zalpha11 in *E. coli*

A. Construction of Expression Vector pCZR225 that Expresses Huzalpha11/MBP-6H Fusion Polypeptide An expression plasmid containing a polynucleotide encoding a human zalpha11 soluble receptor fused C-terminally to maltose binding protein (MBP) was constructed via homologous recombination. The polynucleotide sequence for the MBP-zalpha11 soluble receptor fusion polypeptide is shown in SEQ ID NO:50, with the corresponding protein sequence shown in SEQ ID NO:51. The fusion polypeptide, designated huzalpha11/MBP-6H, in Example 14, contains an MBP portion (amino acid 1 (Met) to amino acid 388 (Ser) of SEQ ID NO:51) fused to the human zalpha11 soluble receptor (amino acid 389 (Cys) to amino acid 606 (His) of SEQ ID NO:51). A fragment of human zalpha11 cDNA (SEQ ID NO:52) was isolated using PCR. Two primers were used in the production of the human zalpha11 fragment in a PCR reaction: (1) Primer ZC20,187 (SEQ ID NO:53), containing 40 bp of the vector flanking sequence and 25 bp corresponding to the amino terminus of the human zalpha11, and (2) primer ZC20,185 (SEQ ID NO:54), containing 40 bp of the 3' end corresponding to the flanking vector sequence and 25 bp corresponding to the carboxyl terminus of the human zalpha11. The PCR Reaction conditions were as follows: 25 cycles of 94° C. for 30 seconds, 50° C. for 30 seconds, and 72° C. for 1 minute; followed by 4° C. soak, run in duplicate. Two μl of the 100 μl PCR reaction was run on a 1.0% agarose gel with 1×TBE buffer for analysis, and the expected approximately 660 bp fragment was seen. The remaining 90 μl of PCR reaction was combined with the second PCR tube precipitated with 400 μl of absolute ethanol. The precipitated DNA used for recombining into the SmaI cut recipient vector pTAP98 to produce the construct encoding the MBP-zalpha11 fusion, as described below.

Plasmid pTAP98 was derived from the plasmids pRS316 and pMAL-c2. The plasmid pRS316 is a *Saccharomyces cerevisiae* shuttle vector (Hieter P. and Sikorski, R., *Genetics* 122:19-27, 1989). pMAL-C2 (NEB) is an *E. coli* expression plasmid. It carries the tac promoter driving MalE (gene encoding MBP) followed by a His tag, a thrombin cleavage site, a cloning site, and the rrnB terminator. The vector pTAP98 was constructed using yeast homologous recombination. 100 ng of EcoR1 cut pMAL-c2 was recombined with 1 μg Pvu1 cut pRS316, 1 μg linker, and 1 μg Sca1/EcoR1 cut pRS316. The linker consisted of oligos ZC19,372 (SEQ ID NO:55) (100 pmol): ZC19,351 (SEQ ID NO:56) (1 pmol): ZC19,352 (SEQ ID NO:57) (1 pmol), and ZC19,371 (SEQ ID NO:58) (100 pmol) combined in a PCR reaction. PCR reaction conditions were as follows: 10 cycles of 94° C. for 30 seconds, 50° C. for 30 seconds, and 72° C. for 30 seconds; followed by 4° C. soak. PCR products were concentrated via 100% ethanol precipitation.

One hundred microliters of competent yeast cells (*S. cerevisiae*) were combined with 10 μl of a mixture containing approximately 1 μg of the human zalpha11 receptor PCR product above, and 100 ng of SmaI digested pTAP98 vector, and transferred to a 0.2 cm electroporation cuvette. The yeast/DNA mixture was electropulsed at 0.75 kV (5 kV/cm), infinite ohms, 25 μF. To each cuvette was added 600 μl of 1.2 M sorbitol and the yeast was then plated in two 300 μl aliquots onto two-URA D plates and incubated at 30° C.

After about 48 hours, the Ura+ yeast transformants from a single plate were resuspended in 1 ml $H_2O$ and spun briefly to pellet the yeast cells. The cell pellet was resuspended in 1 ml of lysis buffer (2% Triton X-100, 1% SDS, 100 mM NaCl, 10 mM Tris, pH 8.0, 1 mM EDTA). Five hundred microliters of the lysis mixture was added to an Eppendorf tube containing 300 μl acid washed glass beads and 200 μl phenol-chloroform, vortexed for 1 minute intervals two or three times, followed by a 5 minute spin in a Eppendorf centrifuge at maximum speed. Three hundred microliters of the aqueous phase was transferred to a fresh tube, and the DNA precipitated with 600 μl ethanol (EtOH), followed by centrifugation for 10 minutes at 4° C. The DNA pellet was resuspended in 100 μl $H_2O$.

Transformation of electrocompetent *E. coli* cells (MC1061, Casadaban et. al. *J. Mol. Biol.* 138, 179-207) was done with 1 μl yeast DNA prep and 40 μl of MC1061 cells. The cells were electropulsed at 2.0 kV, 25 μF and 400 ohms. Following electroporation, 0.6 ml SOC (2% Bacto™ Tryptone (Difco, Detroit, Mich.), 0.5% yeast extract (Difco), 10 mM NaCl, 2.5 mM KCl, 10 mM MgCl2, 10 mM MgSO4, 20 mM glucose) was plated in one aliquot on MM/CA+AMP 100 mg/L plates (Pryor and Leiting, *Protein Expression and Pruification* 10:309-319, 1997).

Cells harboring the correct expression construct for human zalpha11 receptor were identified by expression. Cells were grown in MM/CA with 100 μg/ml Ampicillin for two hours, shaking, at 37° C. 1 ml of the culture was induced with 1 mM IPTG. 2-4 hours later the 250 μl of each culture was mixed with 250 μl acid washed glass beads and 250 μl Thorner buffer with 5% βME and dye (8M urea, 100 mM Tris pH7.0, 10% glycerol, 2 mM EDTA, 5% SDS). Samples were vortexed for one minute and heated to 65° C. for 10 minutes. 20 μl were loaded per lane on a 4%-12% PAGE gel (NOVEX). Gels were run in 1×MES buffer. The positive clones were designated pCZR225 and subjected to sequence analysis. The polynucleotide sequence of MBP-zalpha11 fusion is shown in SEQ ID NO:50.

B. Bacterial Expression of Human huzalpha11/MBP-6H Fusion Polypeptide

One microliter of sequencing DNA was used to transform strain BL21. The cells were electropulsed at 2.0 kV, 25 μF and 400 ohms. Following electroporation, 0.6 ml MM/CA with 100 mg/L Ampicillin.

Cells were grown in MM/CA with 100 μg/ml Ampicillin for two hours, shaking, at 37° C. 1 ml of the culture was induced with 1 mM IPTG. 2-4 hours later the 250 μl of each culture was mixed with 250 μl acid washed glass beads and 250 μl Thorner buffer with 5% βME and dye (8M urea, 100 mM Tris pH7.0, 10% glycerol, 2 mM EDTA, 5% SDS). Samples were vortexed for one minute and heated to 65° C. for 10 minutes. 20 μl were loaded per lane on a 4%-12% PAGE gel (NOVEX). Gels were run in 1×MES buffer. The positive clones were used to grow up for protein purification of the huzalpha11/MBP-6H fusion protein (Example 14, below).

Example 14

Purification of huzalpha11/MBP-6H Soluble Receptor from *E. coli* Fermentation

Unless otherwise noted, all operations were carried out at 4° C. The following procedure was used for purifying huzalpha11/MBP-6H soluble receptor polypeptide. *E. coli* cells containing the pCZR225 construct and expressing huzalpha11/MBP-6H soluble receptor (Example 13) were grown up in SuperBroth II (12 g/L Casien, 24 g/L Yeast Extract, 11.4 g/L di-potassium phosphate, 1.7 g/L Mono-potassium phosphate; Becton Dickenson, Cockeysville, Md.), and frozen in 0.5% glycerol. Twenty grams of the frozen cells in SuperBroth II+Glycerol were used to purify the protein. The frozen cells were thawed and diluted 1:10 in a protease inhibitor solution (Extraction buffer) prior to lysing the cells and releasing the huzalpha11/MBP-6H soluble receptor protein. The diluted cells contained final concentrations of 20 mM Tris (JT Baker, Philipsburg, N.J.) 100 mM Sodium Chloride (NaCl, Mallinkrodt, Paris, Ky.), 0.5 mM pheynlmethylsulfonyl fluoride (PMSF, Sigma Chemical Co., St. Louis, Mo.), 2 μg/ml Leupeptin (Fluka, Switzerland), and 2 μg/ml Aprotinin (Sigma). A French Press cell breaking system (Constant Systems Ltd., Warwick, UK) with temperature of −7 to −10° C. and 30K PSI was used to lyse the cells. The diluted cells were checked for breakage by $A_{600}$ readings before and after the French Press. The lysed cells were centrifuged @ 18,000 G for 45 minutes to remove the broken cell debris, and the supernatant used to purify the protein. Total target protein concentrations of the supernatant was determined via BCA Protein Assay (Pierce, Rockford, Ill.), according to manufacturer's instructions.

A 25 ml column of TALON® Metal Affinity resin (Clontech, Palo Alto, Calf.) (prepared as described below) was poured in a Bio-Rad, 2.5 cm D×10 cm H glass column. The column was packed and equilibrated by gravity with 10 column volumes (CVs) of TALON® Equilibration buffer (20 mM Tris, 100 mM NaCl, pH 8.0). The supernatant was batch loaded to TALON® metal affinity resin and was rocked overnight. The resin was poured back into the column and was washed with 10 CV's of TALON Equilibration buffer by gravity, then gravity eluted with 140 ml of Elution buffer (TALON® Equilibration buffer+200 mM Imidazole-Fluka Chemical). The TALON® column was cleaned with 5 CVs of 20 mM 2-(N-Morhpholino) ethanesulfonic acid pH 5.0 (MES, Sigma), 5 CVs of distilled $H_2O$, then stored in 20% Ethanol/0.1% Sodium Azide. Fourteen ml fractions were collected over the entire elution chromatography and the fractions were read with absorbance at 280 and 320 nM and BCA protein assay; the pass through and wash pools were also saved and analyzed. The protein elution fractions of interest were pooled and loaded straight to Amylose resin (New England Biolabs, Beverly, Mass.).

To obtain more pure huzalphal 11/MBP-6H polypeptide, the TALON® affinity elution pooled fractions were subjected to Amylose resin (22 m1s) at pH 7.4. A 2.5 cm D×10 cm H Bio-Rad column was poured, packed and equilibrated in 10 CVs of Amylose equilibration buffer-20 mM Tris (JT Baker), 100 mM NaCl (Mallinkrodt), 1 mM PMSF (Sigma), 10 mM beta-Mercaptoethanol (BME, ICN Biomedicals Inc., Aurora, Ohio) pH 7.4. The sample was loaded by gravity flow rate of 0.5 ml/min. The column was washed for 10 CVs with Amylose equilibration buffer, then eluted with ~2 CV of Amylose equilibration buffer+10 mM Maltose (Fluka Biochemical, Switzerland) by gravity. 5 ml fractions were collected over the entire chromatography and absorbance at 280 and 320 nM were read. The Amylose column was regenerated with 1 CV of distilled $H_2O$, 5 CVs of 0.1% (w/v) SDS (Sigma), 5 CVs of distilled $H_2O$, and then 5 CVs of Amylose equilibration buffer.

Fractions of interest were pooled and dialyzed in a Slide-A-Lyzer (Pierce) with 4×4L PBS pH 7.4 (Sigma) to remove low molecular weight contaminants, buffer exchange and desalt. After the changes of PBS, the material harvested represented the purified huzalpha11/MBP-6H polypeptide. The purified huzalpha11/MBP-6H polypeptide was analyzed via SDS-PAGE Coomassie staining and Western blot analysis with the anti-rabbit HRP conjugated antibody (Rockland, Gilbertsville, Pa.). The concentration of the huzalpha11/MBP-6H polypeptide was 1.92 mg/ml as determined by BCA analysis.

Purified huzalpha11/MBP-6H polypeptide was prepared for injection into rabbits and sent to R & R Research and Development (Stanwood, Wash.) for antibody production. Rabbits were injected to produce anti anti-huzalpha11/MBP-6H serum (Example 15, below).

Example 15

Zalpha11 Polyclonal Antibodies

Polyclonal antibodies were prepared by immunizing two female New Zealand white rabbits with the purified huzalpha11/MBP-6H polypeptide (Example 14), or the purified recombinant zalpha11CEE soluble receptor (Example 11A). Corresponding polyclonal antibodies were designated rabbit anti-huzalpha11/MBP-6H and rabbit anti-huzalpha11-CEE-BHK respectively. The rabbits were each given an initial intraperitoneal (IP) injection of 200 mg of purified protein in Complete Freund's Adjuvant (Pierce, Rockford, Ill.) followed by booster IP injections of 100 mg purified protein in Incomplete Freund's Adjuvant every three weeks. Seven to ten days after the administration of the third booster injection, the animals were bled and the serum was collected. The rabbits were then boosted and bled every three weeks.

The zalpha11-specific polyclonal antibodies were affinity purified from the rabbit serum using an CNBr-SEPHAROSE 4B protein column (Pharmacia LKB) that was prepared using 10 mg of the purified huzalpha11/MBP-6H polypeptide (Example 14) per gram CNBr-SEPHAROSE, followed by 20× dialysis in PBS overnight. Zalpha11-specific antibodies were characterized by an ELISA titer check using 1 mg/ml of the appropriate protein antigen as an antibody target. The lower limit of detection (LLD) of the rabbit anti-huzalpha11/MBP-6H affinity purified antibody is a dilution of 500 pg/ml. The LLD of the rabbit anti-huzalpha11-CEE-BHK affinity purified antibody is a dilution of 50 pg/ml.

Example 16

Identification of Cells Expressing Zalpha11 Receptor Using RT-PCR

Specific human cell types were isolated and screened for zalpha11 expression by RT-PCR. B-cells were isolated from fresh human tonsils by mechanical disruption through 100 μm nylon cell strainers (Falcon™; Bectin Dickenson, Franklin Lakes, N.J.). The B-cell suspensions were enriched for CD19+ B-cells by positive selection with VarioMACS VS+ magnetic column and CD19 microbeads (Miltenyi Biotec, Auburn, Calif.) as per manufacturer's instructions. T-cells and monocytes were isolated from human apheresed blood samples. CD3+ T-cells were purified by CD3 microbead VarioMACS positive selection and monocytes were purified by VarioMACS negative selection columns (Miltenyi) as per manufacturer's instructions. Samples from each population were stained and analyzed by fluorescent antibody cell sorting (FACS) (Bectin Dickinson, San Jose, Calif.) analysis to determine the percent enrichment and resulting yields. CD19+ B-cells were approximately 96% purified CD3+ T-cells were approximately 95% purified, and monocytes were approximately 96% purified.

RNA was prepared, using a standard method in the art, from all three cell types that were either resting or activated. RNA was isolated from resting cells directly from the column preparations above. The CD19+ and CD3+ cells were activated by culturing at 500,000 cells/ml in RPMI+10% FBS containing PMA 5 ng/ml (Calbiochem, La Jolla, Calif.) and Ionomycin 0.5 ug/ml (Calbiochem) for 4 and 24 hours. The monocytes were activated by culturing in RPMI+10% FBS containing LPS 10 ng/ml (Sigma St. Louis Mo.) and rhIFN-g 10 ng/ml (R&D, Minneapolis, Minn.) for 24 hours. Cells were harvested and washed in PBS. RNA was prepared from the cell pellets using RNeasy Midiprep™ Kit (Qiagen, Valencia, Calif.) as per manufacturer's instructions and first strand cDNA synthesis was generated with Superscript II™ Kit (GIBCO BRL, Grand Island, N.Y.) as per manufacturers protocol.

Oligos ZC19907 (SEQ ID NO:20) and ZC19908 (SEQ ID NO:21) were used in a PCR reaction to screen the above described samples for a 1.2 kb fragment corresponding to zalpha11 message. PCR amplification was performed with Tag Polymerase (BRL Grand Island N.Y.), and conditions as follows: 35 cycles of 95° C. for 1 min., 60° C. for 1 min., 72° C. for 30 sec.; 1 cycle at 72° C. for 10 min.; and 4° C. soak. 10 ul of each 50 μl reaction volume was run on a 2% agarose 1×TAE gel to identify resultant products. PCR products were scored as (−) for no product, (+) for band visible, (++) increased presence of band and (+++) being the most predominant band, with results shown in Table 5 below.

TABLE 5

| cDNA Source | Activation | PCR Product |
|---|---|---|
| CD19+ cells | 0 hr resting | + |
| | 4 hr activated | ++ |
| | 24 hr activated | +++ |
| CD3+ cells | 0 hr resting | − |
| | 4 hr activated | ++ |
| | 24 hr activated | − |
| monocytes | 0 hr resting | − |
| | 24 hr activated | − |

These results indicated that zalpha11 message is present in resting human CD19+ B-cells and increases with mitogenic activation. It also appears to be expressed by human CD3+ T-cells only after 4 hour activation. There was no apparent message in either resting or activated human monocytes.

Example 17

Zalpha11 Immunohistochemistry

A. Cell and Tissue Preparations

Positive control tissues consisted of BaF3 cells transfected with zalpha11 (Example 7) and lymphoid tissues known to express zalpha11 including mouse lymph node, spleen and thymus received from HSD (Harlan Sprague Dawley, Indianapolis, Ind.), monkey lymph node and spleen received from Regional Primate Research Center (University of Washington, Seattle, Wash.), human lymph node and spleen received from CHTN (Cleveland, Ohio). Negative controls performed on each tissue sample included: (1) untransfected BaF3 cells, (2) liver and brain from mouse and human known not to express zalpha11, (3) staining with antibody dilution buffer (Ventann Bioteck Systems, Tucson Ariz.) in the absence of primary antibody, and (4) using zalpha11 soluble protein in competition experiments.

Other cell samples were examined. Both non-stimulated and stimulated HL60 cells were assayed. HL60 cells are a promyelocytic cell line, which can be differentiated into myeloid or granulocyte lineages with different reagents.

Stimulated HL60 samples were prepared as follows: (1) HL60 cells were treated with 10 ng/ml of phorbol-myristate-acetate (PMA) (Sigma, St. Louis, Mo.) for 48 hours to differentiate into monocyte lineage cells; and (2) HL60 cells treated with 1.25% DMSO (Sigma) for 4 days to differentiate into neutrophil-like cells. In addition, human polymorphonuclear (PMN) cells, human granulocytes, human peripheral blood lymphocytes (PBL) and human monocytes from fresh human blood were examined (prepared in house using routine methods in the art). The cells and tissues described above were fixed overnight in 10% NBF (Surgipath, Richmond, Ill.), and embedded in parapalst X-tra (Oxford Scientific, St. Louis, Mo.), and sectioned at 5 μm with a Reichart-Jung 2050 microme (Leica Instruments GmbH, Nussloch, Germany).

B. Immunohistochemistry

Tissue slides were deparaffinized, hydrated to buffer (water), and subjected to steam HIER treatment in Antigen Retrieval Citra buffer (BioGenex, San Roman, Calif.) for 20 minutes. 5% normal goat serum (Vector, Burlingame, Calif.) was used to block non-specific binding for 10 minutes Immunocytochemical screening analyses were performed using polyclonal antibodies to zalpha11 soluble receptor protein (rabbit anti-huzalpha11-MBP-6H and rabbit anti-huzalpha11-CEE-BHK; see, Example 15) as the primary antibodies, at dilutions of 1:200 and 1:400 respectively. Biotin conjugated goat anti-rabbit IgG (Vector; Cat. No. BA-1000, 1.5 mg/ml) was used as the secondary antibody at dilution of 1:200. In separate samples, protein competition was performed by using additional zalpha11CEE soluble receptor protein (in 10× fold excess) (Example 11A) to the primary antibody to pre-block primary antibody immunoreaction. This competition was used as a control for the rabbit polyclonal antibody specificity to zalpha11. Detection was performed on the Ventana ChemMate 500 instrument using a ChemMate DAB Kit (labeled Streptavidin-Biotin Kit with application of a streptavidin-horseradish peroxidase conjugate, and DAB substrate) according to manufacturer's instruction and using the manufacturer's hematoxylin counterstain for 30 seconds (Ventana Biotek Systems, Tucson, Ariz.).

High expression of zalpha11 was observed in the PMA-activated HL60 cells. Low level expression was observed in PBL and HL60 cells without stimulation. A subset of cells in the spleen, thymus and lymph node of mouse showed positive staining. Lymph node and spleen of both human and monkey, and HL60 cells with DMSO stimulation showed minimal or no staining. The signal seen in the cells and tissues was mostly competed out by using the excess zalpha11 soluble receptor protein. The negative control tissues of brain and liver showed no staining.

Example 18

Identifying Peripheral Blood Mononuclear Cells (PBMNC's) that Express Zalpha11 Receptor Using Polyclonal Rabbit Anti-sera to Zalpha11 Soluble Receptor 200 ml fresh heparinized blood was obtained from a normal donor. Blood was diluted 1:1 in PBS, and separated using a Ficoll-Paque PLUS gradient (Pharmacia Biotech, Uppsala, Sweden), and the lymphocyte interface collected. Cells were washed 2× in PBS and resuspended in RPMI+5% FBS media at a concentration of $2\times10^6$ cells/ml.

In order to determine whether expression of zalpha11 receptor is affected by the activation state of the lymphocyte cells, i.e., between resting and activated cells several stimulation conditions were used: 1) un-stimulated, i.e., media alone (RPMI+5% FBS media); 2) stimulated with PMA 10 ng/ml+Ionomycin 0.5 μg/ml (both from Calbiochem); and 3) PHA activation (phytohemagglutinin-P, Difco/VWR). The cells were incubated at 37° C. for 17 hours then collected for staining to detect expression of zalpha11 receptor.

An indirect staining protocol was used. Briefly, the human lymphocyte cells were suspended in staining buffer (PBS+0.02% NaN3+BSA 1% normal human serum 2%) and plated at $2\times10^5$ cells in 50 μl/well in a 96 well plate. Antibodies to the zalpha11CEE soluble receptor (Example 15) were used to determine whether they co-stained with a B-cell (CD-19), T-cell (CD-3) or monocyte marker (CD-14) on the isolated human lymphocytes. A rabbit polyclonal sera to zalpha11 soluble receptor (Rb anti-huzalpha11-CEE-BHK) (Example 15) at 10 μg/ml was used as the antibody to identify zalpha11 on the lymphocytes. A secondary antibody, goat anti-rabbit Ig-FITC (Biosource, Camarillo, Calif.), was used to visualize the Rb anti-huzalpha11-CEE-BHK antibody binding to the zalpha11 receptors. Other antibodies were simultaneously used to stain T cells (CD3-PE; PharMingen, San Diego, Calif.), B cells (CD19-PE) (PharMingen), and monocytes (CD-14-PE) (PharMingen) in order to identify co-staining of the anti-zalpha11 receptor antibody on these cell types. Various controls were used to determine non-specific binding and background levels of staining: (1) an irrelevant rabbit polyclonal sera was used as a non-specific control; and (2) secondary antibody alone was used to determine background binding of that reagent. Purified, zalpha11CEE soluble receptor (Example 11) was used in about a 10-fold excess as a competitive inhibitor to verify the specificity of the rabbit anti-huzalpha11-CEE-BHK antibody to zalpha11 soluble receptor.

After plating the cells and adding the primary and co-staining antibodies, the cells were incubated on ice for 30 minutes, washed 2× with staining buffer, and stained with the secondary antibody, goat anti-rabbit Ig-FITC (Biosource), for 30 minutes on ice. Cells were washed 2× staining buffer, and resuspended at 200 μl per well in staining buffer containing the viability stain 7AAD at about 1 μg/ml final concentration (Sigma, St. Louis, Mo.). Samples were read on the FACS-Caliber (Becton-Dickinson, San Jose, Calif.) and viable cells analyzed.

The rabbit polyclonal to zalpha11 receptor stained resting B cells. The signal on resting B cells was brighter than the signal achieved using the irrelevant rabbit sera, and the signal was diminished to a greater extent on B cells than on T cells with the addition of excess zalpha11-CEE soluble receptor. This experiment was repeated using separated B and T cells, and the results were very similar. Again the staining with the polyclonal rabbit anti-huzalpha11-CEE-BHK antibody to zalpha11 receptor was highest on resting B cells.

Example 19

Zalpha11 Receptor Expression in Various Tissues Using Real-Time Quantitative RT/PCR A. Primers and Probes for Quantitative RT-PCR- Real-time quantitative RT-PCR using the ABI PRISM 7700 Sequence Detection System (PE Applied Biosystems, Inc., Foster City, Calif.) has been previously described (See, Heid, C. A. et al., *Genome Research* 6:986-994, 1996; Gibson, U. E. M. et al., Genome Research 6:995-1001, 1996; Sundaresan, S. et al., *Endocrinology* 139:4756-4764, 1998. This method incorporates use of a gene specific probe containing both reporter and quencher fluorescent dyes. When the probe is intact the reporter dye emission is negated due to the close proximity of the quencher dye. During PCR extension using additional gene-specific forward and reverse primers, the probe is cleaved by 5' nuclease activity of Taq polymerase which releases the reporter dye from the probe resulting in an increase in fluorescent emission.

The primers and probes used for real-time quantitative RT-PCR analyses of zalpha11 expression were designed using the primer design software PRIMER EXPRESS™ (PE Applied Biosystems, Foster City, Calif.). Primers for human zalpha11 were designed spanning an intron-exon junction to eliminate amplification of genomic DNA. The forward primer, ZC22,277 (SEQ ID NO:59) and the reverse primer, ZC22,276 (SEQ ID NO:60) were used in a PCR reaction (below) at about 300 nM concentration to synthesize a 143 bp product. The corresponding zalpha11 TAQMAN® probe, designated ZG31 (SEQ ID NO:61) was synthesized and labeled by PE Applied Biosystems. The ZG31 probe was labeled at the 5' end with a reporter fluorescent dye (6-carboxy-fluorescein) (FAM) (PE Applied Biosystems) and at the 3' end with a quencher fluorescent dye (6-carboxy-tetramethyl-rhodamine) (TAMRA™) (PE Applied Biosystems).

As a control to test the integrity and quality of RNA samples tested, all RNA samples (below) were screened for rRNA using a primer and probe set ordered from PE Applied Biosystems (cat No. 4304483). The kit contains an rRNA forward primer (SEQ ID NO:66) and the rRNA reverse primer (SEQ ID NO:67), rRNA TAQMAN® probe (SEQ ID NO:68) The rRNA probe was labeled at the 5' end with a reporter fluorescent dye VIC (PE Applied Biosystems) and at the 3' end with the quencher fluorescent dye TAMRA™ (PE Applied Biosystems). The rRNA results also serve as an endogenous control and allow for the normalization of the zalpha11 mRNA expression results seen in the test samples.

RNA samples from human CD3, CD19 and monocyte cell types were prepared and described as per Example 16 above. Control RNA was prepared, using RNeasy Miniprep™ Kit (Qiagen, Valencia, Calif.) as per manufacturer's instructions, from approximately 10 million BaF3 cells expressing human zalpha11 receptor (Example 7).

B. Real-time Quantitative RT-PCR-

Relative levels of zalpha11 mRNA were determined by analyzing total RNA samples using the one-step RT-PCR method (PE Applied Biosystems). Total RNA from BaF3 cells expressing human zalpha11 receptor was isolated by standard methods and used to generate a standard curve used for quantitation. The curve consisted of 10-fold serial dilutions ranging from $2.5\text{-}2.5\times10^{-4}$ ng/μl for the rRNA screen and 250-0.025 ng/μl for the zalpha11 screen with each standard curve point analyzed in triplicate. The total RNA samples from the human CD3, CD19 and monocyte cells were also analyzed in triplicate for human zalpha11 transcript levels and for levels of rRNA as an endogenous control. In a total volume of 25 μl, each RNA sample was subjected to a One-Step RT-PCR reaction containing: approximately 25 ng of total RNA in buffer A (50 mM KCL, 10 mM Tris-HCL); the internal standard dye, carboxy-x-rhodamine (ROX)); appropriate primers (approximately 50 nM rRNA primers (SEQ ID NO:66 and SEQ ID NO:67) for the rRNA samples; and approximately 300 nM ZC22,277 (SEQ ID NO:59) and ZC22,276 (SEQ ID NO:60) primers for zalpha11 samples); the appropriate probe (approximately 50 nM rRNA TAQMAN® probe (SEQ ID NO:68) for rRNA samples, approximately 100 nM ZG31 (SEQ ID NO:61) probe for zalpha11 samples); 5.5 mM $MgCl_2$; 300 μM each d-CTP, d-ATP, and d-GTP and 600 μM of d-UTP; MuLV reverse transcriptase (0.25 UV); AMPLITAQ GOLD™ DNA polymerase (0.025 U/μl) (PE Applied Biosystems); and RNase Inhibitor (0.4 U/μl) (PE Applied Biosystems). PCR thermal cycling conditions were as follows: an initial reverse transcription (RT) step of one cycle at 48° C. for 30 minutes; followed by an AMPLITAQ GOLD™ DNA polymerase (PE Applied Biosystems) activation step of one cycle at 95° C. for 10 minutes; followed by 40 cycles of amplification at 95° C. for 15 seconds and 60° C. for 1 minute.

Relative zalpha11 RNA levels were determined by using the Standard Curve Method as described by the manufacturer, PE Biosystems (User Bulletin No. 2: ABI Prism 7700 Sequence Detection System, Relative Quantitation of Gene Expression, Dec. 11, 1997). The rRNA measurements were used to normalize the zalpha11 levels and the resting CD3+ RNA sample was used as a calibrator. Resting CD3 was arbitrarily chosen as the calibrator and given a value of 1.00. The rest of the samples were compared relative to the calibrator. Data are shown in Table 6 below.

TABLE 6

| Sample | Resting | 4 hr Stimulation | 24 hr Stimulation |
|---|---|---|---|
| CD3 | 1.00 | 15.27 | 16.70 |
| CD19 | 20.14 | 65.08 | 25.42 |
| Monocytes | 0.05 | no data | 0.26 |

There was a 15-fold increase in zalpha11 receptor expression in CD3+ at 4 and 24 hrs. Resting CD19 had 20 fold increase in receptor expression relative to resting CD3+. There was a 3 fold increase with 4 hr stimulation that fell back to resting levels by 24 hrs. Monocytes showed no detectable zalpha11 receptor expression in this assay.

Example 20

Identification of Cells Expressing Zalpha11 Receptor Using In Situ Hybridization Specific human tissues were isolated and screened for zalpha11 expression by in situ hybridization. Various human tissues prepared, sectioned and subjected to in situ hybridization included thymus, spleen, tonsil, lymph node and lung. The tissues were fixed in 10% buffered formalin and blocked in paraffin using standard techniques (Example 17). Tissues were sectioned at 4 to 8 microns. Tissues were prepared using a standard protocol ("Development of non-isotopic in situ hybridization" at http://dir.niehs.nih.gov/dirlep/ish.html). Briefly, tissue sections were deparaffinized with HistoClear (National Diagnostics, Atlanta, Ga.) and then dehydrated with ethanol. Next they were digested with Proteinase K (50 μg/ml) (Boehringer Diagnostics, Indianapolis, Ind.) at 37° C. for 2 to 20 minutes. This step was followed by acetylation and re-hydration of the tissues.

Two in situ probes generated by PCR were designed against the human zalpha11 sequence. Two sets of oligos were designed to generate probes for separate regions of the zalpha11 cDNA: (1) Oligos ZC23,684 (SEQ ID NO:62) and ZC23,656 (SEQ ID NO:63) were used to generate a 413 bp probe for zalpha11; and (2) Oligos ZC23,685 (SEQ ID NO:64) and ZC23,657 (SEQ ID NO:65) were used to generate a 430 bp probe for zalpha11. The second probe is 1500 bp 3' of the first zalpha11 probe. The antisense oligo from each set also contained the working sequence for the T7 RNA polymerase promoter to allow for easy transcription of antisense RNA probes from these PCR products. The PCR reaction conditions were as follows: 30 cycles at 94° C. for 30 sec, 60° C. for 1 min., 72° C. for 1.5 min. The PCR products were purified by Qiagen spin columns followed by phenol/chloroform extraction and ethanol precipitation. Probes were subsequently labeled with digoxigenin (Boehringer) or biotin (Boehringer) using an In Vitro transcription System (Promega, Madison, Wis.) as per manufacturer's instruction.

In situ hybridization was performed with a digoxigenin- or biotin-labeled zalpha11 probe (above). The probe was added to the slides at a concentration of 1 to 5 pmol/ml for 12 to 16 hours at 55-60° C. Slides were subsequently washed in 2×SSC and 0.1×SSC at 50° C. The signals were amplified using tyramide signal amplification (TSA) (TSA, in situ indirect kit; NEN) and visualized with Vector Red substrate kit (Vector Lab) as per manufacturer's instructions. The slides were then counter-stained with hematoxylin (Vector Laboratories, Burlingame, Calif.).

A signal was seen in the thymus, tonsil, lung, and lymph node. The positive-staining cells appeared to be lymphocytes and related cells.

Example 21

Isolation of the Mouse Zalpha11 Receptor

A. Mouse Genomic Library Screen

An initial partial mouse zalpha11 sequence was obtained by probing a mouse genomic library with a human zalpha11 receptor polynucleotide probe containing the entire cDNA. The human zalpha11 cDNA was generated by PCR with ZC19,905 (SEQ ID NO:36) and ZC19,906 (SEQ ID NO:37) primers and a plasmid containing full length human zalpha11 (e.g., Example 1) was used for the template. The PCR reaction conditions were as follows: 35 cycles at 98° C. for 1 min., 68° C. for 1 min., and 72° C. for 2 min.; followed by one cycle at 72° C. for 10 min. The PCR product was run on a 1% low melting point agarose (Boerhinger Mannheim) and the approximately 1.5 kb human zalpha11 cDNA isolated using QIAQUICK™ gel extraction kit (Qiagen) as per manufacturer's instructions. This human zalpha11 cDNA was used to screen a mouse genomic DNA library (below).

The mouse genomic DNA library used was embl3 SP6/T7 lambda BamHI cloned library (Clontech, Palo Alto, Calif.). This library representing $7.2\times10^5$ pfu was plated onto an *E. coli* K802 host lawn on 24 NZY plates. Plaque lifts were performed using HYBOND™-N filters (Amersham Pharmacia, Buckinghamshire, England, UK) as per manufacturer's instructions. The filters were denatured in 1.5 M NaCl and 0.5 M NaOH for 10 min. and then neutralized in 1.5 M NaCl and 0.5 M Tris-HCL (pH 7.2) for 10 min. The DNA was affixed to the filter using a STRATALINKER® UV crosslinker (Stratagene) at 1200 joules. The filters were pre-washed to remove cell debris at 65° C. in pre-wash buffer (0.25×SSC, 0.25% SDS and 1 mM EDTA), changing solution three times for a total of 45 min. The filters were prehybridized overnight at 50° C. in EXPRESSHYB™ solution (Clontech) containing 0.1 mg/ml denatured salmon sperm DNA. Approximately 50 ng of the purified human zalpha11 cDNA (above) was labeled with $^{32}P$ using the REDIPRIME™ II Random Prime Labeling System (Amersham Pharmacia) as per manufacturers instructions. Unincorporated radioactivity was removed from the zaplha11 cDNA probe using a NUCTRAP™ push column (Stratagene, La Jolla, Calif.). Filters were hybridized in EXPRESSHYB™ solution (Clontech) containing about 0.5 to about $1\times10^6$ cpm/ml zalpha11 cDNA probe, about 0.1 mg/ml denatured salmon sperm DNA and denatured 0.5 μg/ml cot-1 DNA. Hybridization took place overnight at 50° C. Filters were washed in 2×SSC, 0.1% SDS at room temperature for 2 hours (changing wash several times) then the temperature was raised to 60° C. for one hour (changing buffer once). Overnight exposure at −80° C. showed 6 plaques representing primary isolates.

To obtain secondary plaque isolates, the 6 plaques representing primary isolates were picked with a Pasteur pipette and eluted overnight at 4° C. in 1 ml SM (0.1 M NaCl, 50 mM Tris pH 7.5, 10 mM $MgSO_4$, 0.02% gelatin) containing a few drops of chloroform. After determining phage titers, about 12.5× the estimated amount of phage in the original plug (12.5× coverage) of 6 primary isolates was plated on a lawn of *E. coli* K802 cells embedded in 10 mM $MgSO_4$/NZY top agarose on NZY maxi plates, and grown overnight at 37° C. Plaque lifts were done using HYBOND™-N filters (Amersham Pharmacia) as per manufacturer's instructions. Filters were fixed as per above. The second round filters were prewashed to remove cell debris at 65° C. in pre-wash buffer (2×SSC, 0.1% SDS and 1 mM EDTA), changing solution three times for a total of 45 min. The second round filter lifts were then prehybridized, and the zalpha11 cDNA probe prepared as described above.

The second round filters were hybridized as above in EXPRESSHYB™ solution (Clontech) containing about $10^6$ cpm/ml zalpha11 cDNA probe containing about 0.1 mg/ml denatured salmon sperm DNA. Hybridization took place overnight at 50° C. Wash conditions described above for the primary screen were repeated for this secondary screen. After an overnight exposure at −80° C., two of the 6 original primary plaques isolates were verified as positive in the secondary screen. Positive plaques hybridizing to human zalpha11 cDNA in the secondary screen were picked with a Pasteur pipette and designated 7b1 and 20b1.

The isolated plaques No. 7b1 and 20b1 were eluted in 200 μl SM overnight at 4° C. Serial 10-fold serial dilutions ranging from $10^{-2}$ to $10^{-6}$ of each isolate were plated on host *E. coli* K802 cells to determine the titer. Isolate 20b1 had a titer of $4\times10^3$ pfu/μl and was further pursued. 4 plates were prepared by plating $10^5$ pfu/plate on confluent host *E. coli* K802 cells in order to make a phage DNA prep. Plates were grown at 37° C. for about 6.5 hours until phage lysis was starting to get confluent. The phage was then eluted overnight at 4° C. in 12 ml of SM per plate. Plates were then shaken at room temperature one hour, the supernatant was removed; 1% chloroform was added and supernatant was shaken again for 15 min. The 20b1 phage DNA was prepped using the WIZARD™ Lambda Preps DNA Purification System (Promega, Madison, Wis.; sections IV and VI).

Samples of 20b1 phage DNA were cut with several restriction enzymes to generate DNA fragments for Southern blotting. The digests were run on a 1% TBE agarose gel. The gel was soaked in 0.25 M HCl for 30 min.; rinsed in distilled H2O; soaked in 0.5M NaOH and 1.5 M NaCl for 40 min. with one solution change and neutralized in 1.5 NaCl and 0.5 Tris-HCL (pH 7.2) for 40 min. with one solution change. A TURBOBLOTTER™ Rapid Downward Transfer System (Schleicher & Schuell, Keene, N.H.) was set up to transfer the DNA onto a NYTRAN®/BA-S membrane (Schleicher & Schuell) overnight. The DNA was affixed to the NYTRAN® membrane using a STRATALINKER® UV crosslinker (Stratagene, La Jolla, Calif.) at 1200 joules. The blot was prehybridized as described above. About 50 ng of the human zalpha11 cDNA was labeled and purified for a probe, as described above. Filters were hybridized as above in EXPRESSHYB™ solution (Clontech) containing about $10^6$ cpm/ml zalpha11 cDNA probe and about 0.1 mg/ml denatured salmon sperm DNA. Hybridization took place overnight at 50° C. The blot was washed as described above and exposed to film overnight at −80° C.

The Southern showed a DNA fragment generated from a BamHI/StuI digest which hybridized to the human zalpha11 cDNA probe in the expected size range of 1.3 to 1.6 kb. This fragment was pursued. Approximately 3 μg of 20b1 lambda DNA was cut with 20 units of BamHI (Boehringer Mannheim, Indianapolis, Ind.) and 20 Units StuI (NEB, Beverly, Mass.) for 2 hours at 37° C. The digest was run on a 1% TBE gel and a 1.3 kb doublet and 1.6 kb doublet bands were excised from the gel and the DNA was extracted from the agarose using the QIAQUICK™ Gel Extraction Kit (Qiagen, Valencia, Calif.). Due to the low yield of DNA from the prep, it was not possible to determine by additional restriction digest analysis whether fragments which hybridized to the human zalpha11 cDNA probe were BamHI/StuI or StuI/StuI fragments. Thus, blunt ligations using 5 μl of the 1.3 kb doublet fragment and 5 μl of the 1.6 kb doublet fragment were done using the ZERO BLUNT® PCR Cloning Kit (Invitrogen, Carlsbad, Calif.). The blunt ligation yielded positive clones with both of the 1.6 kb fragments and one of the 1.3 kb fragments. These clones were digested with EcoRI (Life Technologies) which flanks the T-overhang site where the 1.6 and 1.3 kb fragments were inserted. Another Southern blot was performed to determine which was the original fragment hybridizing to the human zalpha11 cDNA probe. The 1% TBE gel was treated and the DNA was transferred to the NYTRAN® blot as described above.

The blot was prehybridized as above in 10 ml of hybridization solution. A different human zalpha11 polynucleotide probe was prepared. Another full length zalpha11 cDNA human zalpha11 fragment was generated for use as a probe by PCR with the oligos ZC19,905 (SEQ ID NO: 36) and ZC20,097 (SEQ ID NO: 27). The PCR reaction conditions were as follows: 95° C. for 1 min.; 35 cycles of 95° C. for 1 min., 55° C. for 1 min., and 72° C. for 2 min.; followed by one cycle at 72° C. for 10 min. The PCR product was run on a 1% low melting point agarose (Boerhinger Mannheim) and the approximately 1.5 kb human zalpha11 cDNA isolated using QIAQUICK™ gel extraction kit (Qiagen) as per manufacturer's instructions. About 50 ng of this isolated human zalpha11 cDNA fragment was labeled with $^{32}P$ and purified as described above. Filters were hybridized as above in EXPRESSHYB™ solution (Clontech) containing about $10^6$ cpm/ml zalpha11 cDNA probe, about 0.1 mg/ml denatured salmon sperm, and denatured 0.5 μg/ml cot-1 DNA. Hybridization and washing was as described above. The blot was exposed to film 1.5 hours at −80° C. and the 1.3 kb insert was strongly hybridizing to the human zalpha11 probe.

This clone was sequenced and found to contain a mouse zalpha11 3' coding exon with a termination codon and upstream intron sequence. Sequencing primers used were: ZC3,424 (SEQ ID NO:86), ZC694 (SEQ ID NO:87), ZC24,399 (SEQ ID NO:88), and ZC24,400 (SEQ ID NO:89). The genomic sequence of mouse zalpha11 including the 3' exon is shown in SEQ ID NO:69. The 3' exon coding sequence starts at nucleotide 543 and ends at nucleotide 1262 in SEQ ID NO:69, encoding a 240 amino acid exon (SEQ ID NO:70).

B. PCR Screen of Mouse cDNA Panel

A panel of available in-house and commercial mouse cDNAs (Clontech; Life technologies, Gaithersburg, Md.) was screened by PCR using ZC24,432 (SEQ ID NO:71) and ZC24,433 (SEQ ID NO:72) as primers (about 20 pmol each). The PCR reaction conditions were as follows: 94° C., 2 min.; 32 cycles of 94° C. for 20 sec., 64° C. for 30 sec., and 72° C. for 30 sec.; followed by one cycle at 72° C. for 5 min. Mouse spleen, dendritic cells, neonatal skin, bone marrow, wild type BaF3 cells, EL4 cells, and lung showed strong PCR products of the predicted 450 bp size.

C. 5' Nested RACE

5' RACE reactions were performed using 20 pmol each of primers ZC9,739 (SEQ ID NO:73) and ZC24,434 (SEQ ID NO:74) and CD90+ selected mouse spleen marathon cDNA as a template. The marathon cDNA was prepared using a Marathon cDNA Amplification Kit (Clontech) according to the manufacturer's instructions. The PCR reaction conditions were as follows: 94° C. for 1 min.; 5 cycles of 94° C. for 20 sec., and 70° C. for 1.5 min.; followed by 25 cycles of 94° C. for 20 sec., 64° C. for 20 sec., and 70° C. for 1.5 min.; followed by one cycle at 72° C. for 5 min.

To enrich for mouse zalpha11 5' RACE product, a nested 5' RACE reaction was performed using PCR reaction conditions as described above for the initial 5'RACE, except using nested primers ZC24,431 (SEQ ID, NO:75) and ZC9,719 (SEQ ID NO:76), and one μl of a 1/20 dilution of the initial 5' RACE reaction (above) as a template. The products were purified by gel electrophoresis, the DNA was eluted using the QIAEXII™ Agarose Gel Extraction Kit (QIAGEN®)) and subcloned using the TOPO TA Cloning Kit (Invitrogen). Positive clones were identified by colony PCR using 10 pmol each of ZC24,431 (SEQ ID NO:75) and ZC24,511 (SEQ ID NO:77). The PCR reaction conditions were as follows: 94° C., 2 min.; 35 cycles of 94° C. for 20 sec., 64° C. for 20 sec., and 72° C. for 30 sec.; followed by one cycle at 72° C. for 5 min. Two subclones from each of the nested 5'RACE reactions were sequenced. All the clones contained some zalpha 11 sequence but none were complete. A compiled sequence was generated from the incomplete 5'RACE clones and the 3' exon sequence (SEQ ID NO:70) representing a preliminary partial sequence of the mouse zalpha11 polynucleotide and corresponding polypeptide. The preliminary sequence of the partial mouse zalpha11 cDNA is show in SEQ ID NO:78 (5'end) and SEQ ID NO:80 (3'end); there was approximately 330 nucleotides of yet unknown sequence between SEQ ID NO:78 (5'end) and SEQ ID NO:80 (3'end) to comprise the entire mouse zalpha11 cDNA (see below). The corresponding amino acid sequences for SEQ ID NO:78 and SEQ ID NO:80 are shown in SEQ ID NO:79 (N-terminus) and SEQ ID NO:81 (C-terminus) respectively.

D. Full Length PCR

Primers were designed from the mouse upstream UTR of the initiation Met and downstream of the termination codon for full length PCR. 20 pmol each of primers ZC24,616 (SEQ ID NO:82) and ZC24,615 (SEQ ID NO:83) were used in PCR reactions using a mouse dendritic cell marathon cDNA or a neonatal mouse skin in-house cDNA library as a template. PCR reaction conditions were as follows: 94° C., 1 min.; 30 cycles of 94° C. for 20 sec., and 66° C. for 2 min.; followed by one cycle at 72° C. for 5 min. The PCR products were purified by gel electrophoresis, and the cDNA was eluted using the QIAQUICK™ Gel Extraction Kit and subcloned using the TA CLONING® Kit (Invitrogen). 2 subclones from each PCR reaction were sequenced. Sequencing primers used were: ZC694 (SEQ ID NO:87), ZC3,424 (SEQ ID NO:86), ZC24,431 (SEQ ID NO:75), ZC24,511 (SEQ ID NO:77), ZC24,806 (SEQ ID NO:90), and ZC24,807 (SEQ ID NO:91). The sequence of the full length mouse zalpha11 cDNA is show in SEQ ID NO:84. The corresponding amino acid sequence is shown in SEQ ID NO:85.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of producing a polypeptide comprising:

culturing a cell comprising an expression vector, wherein the expression vector comprises the following operably linked elements:

a transcription promoter; a DNA construct encoding a polypeptide, wherein the polypeptide comprises:

a DNA segment encoding a polypeptide consisting of an amino acid sequence as shown in SEQ ID NO:2 from amino acid number 20 (Cys) to amino acid number 538 (Ser), wherein the polypeptide further comprises a WSXWS motif as shown in SEQ ID NO:3, and wherein a Trp residue in the WSXWS motif (SEQ ID NO:3) is mannosylated;

a transcription terminator, and wherein the promoter is operably linked to the DNA construct, and the DNA construct is operably linked to the transcription terminator, wherein the cell expresses a polypeptide encoded by the DNA construct; and isolating the polypeptide produced by the cell.

2. The method according to claim 1, wherein the expression vector further comprising a secretory signal sequence operably linked to the DNA segment.

3. A method of producing a soluble receptor polypeptide comprising:

culturing a cell comprising an expression vector, wherein the expression vector comprises the following operably linked elements:

a transcription promoter;

a DNA construct encoding a polypeptide, wherein the polypeptide comprises:

a DNA segment encoding a polypeptide consisting of an amino acid sequence as shown in SEQ ID NO:2 from amino acid number 20 (Cys) to amino acid number 237 (His), wherein the polypeptide further comprises a WSXWS motif as shown in SEQ ID NO:3, and wherein a Trp residue in the WSXWS motif (SEQ ID NO:3) is mannosylated;

a transcription terminator, and wherein the promoter is operably linked to the DNA construct, and the DNA construct is operably linked to the transcription terminator, wherein the cell expresses a polypeptide encoded by the DNA construct; and isolating the soluble receptor polypeptide produced by the cell.

4. The method according to claim 3, wherein the expression vector further comprising a secretory signal sequence operably linked to the DNA segment.

5. The method according to claim 3, wherein the polypeptide encoded by the DNA segment further comprises a biotin/avidin label, radionuclide, enzyme, substrate, cofactor, inhibitor, fluorescent marker, chemiluminescent marker, toxin, cytotoxic molecule or an immunoglobulin Fc domain.

6. A method of producing a fusion protein comprising:

culturing a cell comprising an expression vector, wherein the expression vector comprises the following operably linked elements:

a transcription promoter;

a DNA construct encoding a fusion protein, wherein the fusion protein comprises:

(i) a first DNA segment encoding a polypeptide consisting of a sequence of amino acid residues selected from the group consisting of:

(a) the amino acid sequence of SEQ ID NO:2 from amino acid number 20 (Cys) to amino acid number 237 (His);

(b) the amino acid sequence of SEQ ID NO:2 from amino acid number 20 (Cys) to amino acid number 255 (Leu);

(c) the amino acid sequence of SEQ ID NO:2 from amino acid number 20 (Cys) to amino acid number 538 (Ser); and wherein the polypeptide further comprises a WSXWS motif as shown in SEQ ID NO:3, and wherein a Trp residue in the WSXWS motif (SEQ ID NO:3) is mannosylated; and (ii) at least one other DNA segment encoding an additional polypeptide, wherein the first and other DNA segments are connected in-frame; and wherein the first and other DNA segments encode the fusion protein;

a transcription terminator, and wherein the promoter is operably linked to the DNA construct, and the DNA construct is operably linked to the transcription terminator, wherein the cell expresses a polypeptide encoded by the DNA construct; and isolating the polypeptide produced by the cell.

7. The method according to claim 6, wherein the expression vector further comprising a secretory signal sequence operably linked to the DNA segment.

* * * * *